US011660212B2

(12) United States Patent
Belcher et al.

(10) Patent No.: US 11,660,212 B2
(45) Date of Patent: May 30, 2023

(54) METHOD AND APPARATUS FOR IMPLANTING A KNEE PROSTHESIS

(71) Applicant: Biomet Manufacturing, LLC, Warsaw, IN (US)

(72) Inventors: Nathan Belcher, Ferguson, MO (US); Bradley T. Durcholz, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 364 days.

(21) Appl. No.: 16/927,434

(22) Filed: Jul. 13, 2020

(65) Prior Publication Data
US 2020/0337867 A1    Oct. 29, 2020

Related U.S. Application Data

(63) Continuation of application No. 15/680,813, filed on Aug. 18, 2017, now Pat. No. 10,744,005, which is a
(Continued)

(51) Int. Cl.
*A61F 2/46*      (2006.01)
*A61B 17/15*    (2006.01)
(Continued)

(52) U.S. Cl.
CPC .......... *A61F 2/4684* (2013.01); *A61B 17/155* (2013.01); *A61B 17/157* (2013.01);
(Continued)

(58) Field of Classification Search
CPC ....... A61F 2/3858; A61F 2/389; A61F 2/4684
See application file for complete search history.

(56) References Cited

U.S. PATENT DOCUMENTS 4,136,405 A    1/1979  Pastrick et al.
4,711,639 A  * 12/1987  Grundei .............. A61F 2/30907
                                                                        623/20.31
(Continued)

FOREIGN PATENT DOCUMENTS

EP          0555003 A1     8/1993
EP          0689796 A1     1/1996

OTHER PUBLICATIONS

U.S. Appl. No. 13/153,983 U.S. Pat. No. 8,979,847, filed Jun. 6, 2011, Method and Apparatus for Implanting a Knee Prosthesis.
(Continued)

*Primary Examiner* — Zade Coley
(74) *Attorney, Agent, or Firm* — Schwegman Lundberg & Woessner, P.A.

(57)   ABSTRACT

A method for preparing a femur for receiving a prosthesis. The method includes the following: fixing a femoral trial component to the femur; coupling a reamer bushing relative to the femoral trial component; reaming a cavity into the femur using the reamer bushing as a guide; coupling at least one of a modular femoral box trial and a stem adapter relative to the femoral trial component; trialing the femoral trial component with the articulating surface of the femoral trial component; and performing the coupling of the reamer bushing, the reaming of the cavity, the coupling of the at least one of the modular femoral box trial and stem adapter, and the trialing of the femoral trial component all while the femoral trial component remains fixed to the distal femur.

5 Claims, 39 Drawing Sheets

Related U.S. Application Data continuation of application No. 14/626,398, filed on Feb. 19, 2015, now Pat. No. 9,770,345, which is a continuation of application No. 13/153,983, filed on Jun. 6, 2011, now Pat. No. 8,979,847.

(51) Int. Cl.
*A61B 17/16* (2006.01)
*A61B 17/17* (2006.01)
*A61F 2/30* (2006.01)
*A61F 2/38* (2006.01)

(52) U.S. Cl.
CPC ...... *A61B 17/1675* (2013.01); *A61B 17/1764* (2013.01); *A61B 17/1767* (2013.01); *A61F 2/30721* (2013.01); *A61F 2/38* (2013.01); *A61F 2/389* (2013.01); *A61F 2/3859* (2013.01)

(56) References Cited

U.S. PATENT DOCUMENTS

| | | | |
|---|---|---|---|
| 4,795,468 A * | 1/1989 | Hodorek | A61F 2/389 623/20.28 |
| 4,969,889 A | 11/1990 | Greig | |
| 4,983,179 A | 1/1991 | Sjostrom | |
| 5,035,699 A | 7/1991 | Coates | |
| 5,098,436 A | 3/1992 | Ferrante et al. | |
| 5,100,409 A | 3/1992 | Coates et al. | |
| 5,108,442 A * | 4/1992 | Smith | A61F 2/389 623/20.33 |
| 5,129,907 A | 7/1992 | Heldreth et al. | |
| 5,156,606 A | 10/1992 | Chin | |
| 5,176,684 A | 1/1993 | Ferrante et al. | |
| 5,258,032 A | 11/1993 | Bertin | |
| 5,275,603 A | 1/1994 | Ferrante et al. | |
| 5,290,313 A | 3/1994 | Heldreth | |
| 5,306,276 A | 4/1994 | Johnson et al. | |
| 5,312,411 A | 5/1994 | Steele et al. | |
| 5,330,534 A * | 7/1994 | Herrington | A61F 2/3886 623/20.27 |
| 5,370,701 A | 12/1994 | Finn | |
| 5,417,694 A | 5/1995 | Marik et al. | |
| 5,417,695 A | 5/1995 | Axelson, Jr. | |
| 5,423,822 A | 6/1995 | Hershberger et al. | |
| 5,445,640 A | 8/1995 | Johnson et al. | |
| D362,503 S | 9/1995 | Cook et al. | |
| 5,451,228 A | 9/1995 | Johnson et al. | |
| 5,458,645 A | 10/1995 | Bertin | |
| 5,472,415 A | 12/1995 | King et al. | |
| 5,474,559 A | 12/1995 | Bertin et al. | |
| 5,476,466 A | 12/1995 | Barrette et al. | |
| 5,484,446 A | 1/1996 | Burke et al. | |
| 5,486,178 A | 1/1996 | Hodge | |
| 5,496,324 A | 3/1996 | Barnes | |
| 5,522,897 A | 6/1996 | King et al. | |
| 5,540,696 A | 7/1996 | Booth, Jr. et al. | |
| 5,569,261 A | 10/1996 | Marik et al. | |
| 5,578,039 A | 11/1996 | Vendrely et al. | |
| 5,601,563 A | 2/1997 | Burke et al. | |
| 5,609,642 A | 3/1997 | Johnson et al. | |
| 5,613,970 A | 3/1997 | Houston et al. | |
| 5,628,749 A | 5/1997 | Vendrely et al. | |
| 5,634,927 A | 6/1997 | Houston et al. | |
| 5,653,714 A | 8/1997 | Dietz et al. | |
| 5,658,292 A | 8/1997 | Axelson, Jr. | |
| 5,662,656 A | 9/1997 | White | |
| 5,667,511 A | 9/1997 | Vendrely et al. | |
| 5,683,396 A | 11/1997 | Tokish et al. | |
| 5,683,397 A | 11/1997 | Vendrely et al. | |
| 5,683,398 A | 11/1997 | Carls et al. | |
| 5,683,469 A | 11/1997 | Johnson et al. | |
| 5,683,470 A | 11/1997 | Johnson et al. | |
| 5,690,636 A | 11/1997 | Wildgoose | |
| 5,693,056 A | 12/1997 | Carls et al. | |
| 5,702,460 A | 12/1997 | Carls et al. | |
| 5,702,463 A * | 12/1997 | Pothier | A61F 2/389 623/20.32 |
| 5,716,361 A | 2/1998 | Masini | |
| 5,720,752 A | 2/1998 | Elliot et al. | |
| 5,733,290 A * | 3/1998 | McCue | A61F 2/4684 606/88 |
| 5,743,915 A | 4/1998 | Bertin et al. | |
| 5,769,855 A | 6/1998 | Bertin et al. | |
| 5,776,200 A | 7/1998 | Johnson et al. | |
| 5,782,920 A | 7/1998 | Colleran | |
| 5,853,415 A | 12/1998 | Bertin et al. | |
| 5,860,981 A | 1/1999 | Bertin et al. | |
| 5,879,393 A | 3/1999 | Whiteside et al. | |
| 5,885,296 A | 3/1999 | Masini | |
| 5,944,722 A | 8/1999 | Masini | |
| 5,957,926 A | 9/1999 | Masini | |
| 5,961,523 A | 10/1999 | Masini | |
| 5,971,989 A | 10/1999 | Masini | |
| 5,976,147 A | 11/1999 | LaSalle et al. | |
| 5,989,261 A | 11/1999 | Walker et al. | |
| 6,013,081 A | 1/2000 | Burkinshaw et al. | |
| 6,063,091 A | 5/2000 | Lombardo et al. | |
| 6,068,633 A | 5/2000 | Masini | |
| 6,077,269 A | 6/2000 | Masini | |
| 6,123,710 A | 9/2000 | Pinczewski et al. | |
| 6,126,692 A * | 10/2000 | Robie | A61F 2/389 623/20.32 |
| 6,159,216 A | 12/2000 | Burkinshaw et al. | |
| 6,187,010 B1 | 2/2001 | Masini | |
| 6,214,011 B1 | 4/2001 | Masini | |
| 6,228,091 B1 | 5/2001 | Lombardo et al. | |
| 6,270,502 B1 | 8/2001 | Stulberg | |
| 6,280,476 B1 * | 8/2001 | Metzger | A61F 2/34 623/18.11 |
| 6,344,043 B1 | 2/2002 | Pappas | |
| 6,355,045 B1 | 3/2002 | Gundlapaili et al. | |
| 6,458,136 B1 | 10/2002 | Allard et al. | |
| 6,500,208 B1 * | 12/2002 | Metzger | A61F 2/389 623/20.15 |
| 6,503,254 B2 | 1/2003 | Masini | |
| 6,575,980 B1 | 6/2003 | Robie et al. | |
| 6,620,168 B1 | 6/2003 | Lombardo et al. | |
| 6,702,821 B2 | 3/2004 | Bonutti | |
| 6,740,092 B2 | 5/2004 | Lombardo et al. | |
| 6,761,723 B2 | 7/2004 | Buttermann et al. | |
| 6,764,492 B2 | 7/2004 | Taft | |
| 6,770,078 B2 | 8/2004 | Bonutti | |
| 6,827,723 B2 | 12/2004 | Carson | |
| 6,875,237 B2 | 4/2005 | Dye et al. | |
| 6,916,324 B2 | 7/2005 | Sanford | |
| 6,916,325 B2 | 7/2005 | Kana et al. | |
| 6,916,340 B2 * | 7/2005 | Metzger | A61F 2/389 623/908 |
| 6,923,817 B2 | 8/2005 | Carson et al. | |
| 6,923,832 B1 | 8/2005 | Sharkey et al. | |
| 6,942,670 B2 | 9/2005 | Heldreth et al. | |
| 6,962,593 B2 | 11/2005 | Sanford et al. | |
| 6,969,393 B2 | 11/2005 | Pinczewski et al. | |
| 6,974,481 B1 | 12/2005 | Carson | |
| 7,001,394 B2 | 2/2006 | Gundlapaili et al. | |
| 7,029,477 B2 | 4/2006 | Grimm | |
| 7,060,074 B2 | 6/2006 | Rosa et al. | |
| 7,094,241 B2 | 8/2006 | Hodorek et al. | |
| RE39,301 E | 9/2006 | Bertin | |
| 7,104,996 B2 | 9/2006 | Bonutti | |
| 7,128,745 B2 | 10/2006 | Masini | |
| 7,141,053 B2 | 11/2006 | Rosa et al. | |
| 7,144,399 B2 | 12/2006 | Hayes et al. | |
| 7,172,597 B2 | 2/2007 | Sanford | |
| 7,172,599 B2 | 2/2007 | Steffensmeier et al. | |
| 7,175,630 B2 | 2/2007 | Fading et al. | |
| 7,182,767 B2 | 2/2007 | Canonaco et al. | |
| 7,237,556 B2 | 7/2007 | Smothers et al. | |
| 7,241,298 B2 | 7/2007 | Nemec et al. | |
| 7,303,565 B2 | 12/2007 | Buttermann et al. | |
| 7,344,541 B2 | 3/2008 | Haines et al. | |
| 7,371,240 B2 | 5/2008 | Pinczewski et al. | |
| 7,374,563 B2 | 5/2008 | Roger et al. | |
| 7,390,327 B2 | 6/2008 | Collazo et al. | |

(56) References Cited

U.S. PATENT DOCUMENTS

| | | | |
|---|---|---|---|
| 7,544,211 B2 | 6/2009 | Rochetin | |
| 7,686,812 B2 | 3/2010 | Axelson, Jr. et al. | |
| 8,012,215 B2* | 9/2011 | Metzger | A61F 2/389 623/20.15 |
| 8,038,681 B2 | 10/2011 | Koenemann | |
| 8,187,280 B2 | 5/2012 | May et al. | |
| 8,979,847 B2 | 3/2015 | Belcher et al. | |
| 9,770,345 B2 | 9/2017 | Belcher | |
| 2002/0082607 A1* | 6/2002 | Heldreth | A61F 2/4684 606/102 |
| 2003/0009232 A1 | 1/2003 | Metzger et al. | |
| 2005/0075638 A1 | 4/2005 | Collazo | |
| 2005/0246027 A1* | 11/2005 | Metzger | A61F 2/4637 623/20.15 |
| 2006/0058803 A1 | 3/2006 | Cuckler et al. | |
| 2007/0233141 A1 | 10/2007 | Park et al. | |
| 2008/0177337 A1 | 7/2008 | Mcgovern et al. | |
| 2008/0306484 A1 | 12/2008 | Coon et al. | |
| 2009/0088762 A1 | 4/2009 | Koenemann | |
| 2009/0125114 A1 | 5/2009 | May et al. | |
| 2009/0149964 A1 | 6/2009 | May et al. | |
| 2009/0222014 A1 | 9/2009 | Bojarski et al. | |
| 2010/0163261 A1 | 7/2010 | Tomayko et al. | |
| 2010/0191339 A1 | 7/2010 | Brooks et al. | |
| 2011/0307067 A1 | 12/2011 | Dees | |
| 2012/0029649 A1* | 2/2012 | Collazo | A61F 2/389 623/20.28 |
| 2015/0157472 A1 | 6/2015 | Belcher et al. | |
| 2017/0340458 A1 | 11/2017 | Belcher et al. | |

OTHER PUBLICATIONS

U.S. Appl. No. 14/626,398 U.S. Pat. No. 9,770,345, filed Feb. 19, 2015, Method and Apparatus for Implanting a Knee Prosthesis.

U.S. Appl. No. 15/680,813, filed Aug. 18, 2017, Method and Apparatus for Implanting a Knee Prosthesis.

"U.S. Appl. No. 13/153,983, Examiner Interview Summary dated Mar. 18, 2014", 3 pgs.

"U.S. Appl. No. 13/153,983, Examiner Interview Summary dated Dec. 26, 2013", 3 pgs.

"U.S. Appl. No. 13/153,983, Final Office Action dated Sep. 9, 2014", 6 pgs.

"U.S. Appl. No. 13/153,983, Non Final Office Action dated Feb. 19, 2014", 6 pgs.

"U.S. Appl. No. 13/153,983, Non Final Office Action dated Oct. 7, 2013", 6 pgs.

"U.S. Appl. No. 13/153,983, Notice of Allowance dated Nov. 7, 2014", 5 pgs.

"U.S. Appl. No. 13/153,983, Response filed Jan. 2, 2014 to Non Final Office Action dated Oct. 7, 2013", 12 pgs.

"U.S. Appl. No. 13/153,983, Response filed May 19, 2014 to Non Final Office Action dated Feb. 19, 2014", 14 pgs.

"U.S. Appl. No. 13/153,983, Response filed Oct. 17, 2014 to Final Office Action dated Sep. 9, 2014", 10 pgs.

"U.S. Appl. No. 14/626,398, Advisory Action dated Oct. 31, 2016", 2 pgs.

"U.S. Appl. No. 14/626,398, Final Office Action dated Aug. 19, 2016", 8 pgs.

"U.S. Appl. No. 14/626,398, Non Final Office Action dated Jan. 25, 2017", 5 pgs.

"U.S. Appl. No. 14/626,398, Non Final Office Action dated Apr. 22, 2016", 8 pgs.

"U.S. Appl. No. 14/626,398, Notice of Allowance dated May 18, 2017", 5 pgs.

"U.S. Appl. No. 14/626,398, Response filed Apr. 20, 2017 to Non Final Office Action dated Jan. 25, 2017", 6 pgs.

"U.S. Appl. No. 14/626,398, Response filed Jul. 21, 2016 to Non Final Office Action dated Apr. 22, 2016", 9 pgs.

"U.S. Appl. No. 14/626,398, Response filed Oct. 19, 2016 to Final Office Action dated Aug. 19, 2016", 8 pgs.

"U.S. Appl. No. 15/680,813, Advisory Action dated Mar. 4, 2020", 3 pgs.

"U.S. Appl. No. 15/680,813, Final Office Action dated Dec. 23, 2019", 8 pgs.

"U.S. Appl. No. 15/680,813, Non Final Office Action dated Sep. 10, 2019", 8 pgs.

"U.S. Appl. No. 15/680,813, Notice of Allowance dated Apr. 14, 2020", 5 pgs.

"U.S. Appl. No. 15/680,813, Preliminary Amendment filed Dec. 12, 2018", 4 pgs.

"U.S. Appl. No. 15/680,813, Response filed Feb. 24, 2020 to Final Office Action dated Dec. 23, 2019", 6 pgs.

"U.S. Appl. No. 15/680,813, Response filed Dec. 6, 2019 to Non Final Office Action dated Sep. 10, 2019", 7 pgs.

"Vanguard™ Complete Knee System", SSK Revision System, Biomet® Orthopedics, Inc.,, (2007), 6 pgs.

"Vanguard™ SSK Revision System", Surgical Technique, Biomet® Orthopedics, (2008), 64 pgs.

"Vanguard™ SSK Revision System", (2009), 1 pg.

* cited by examiner

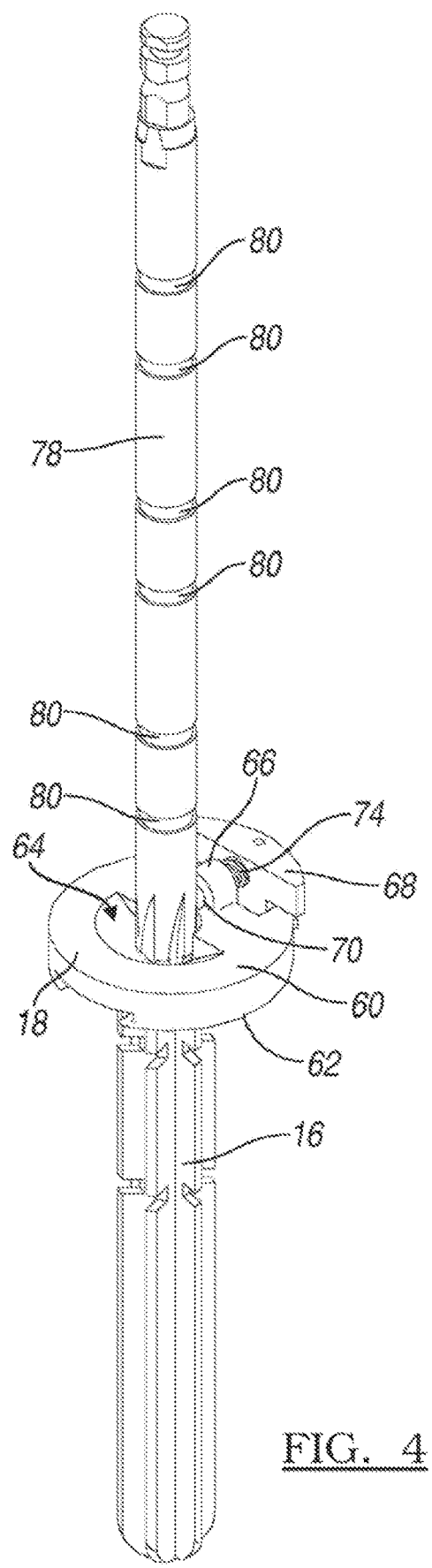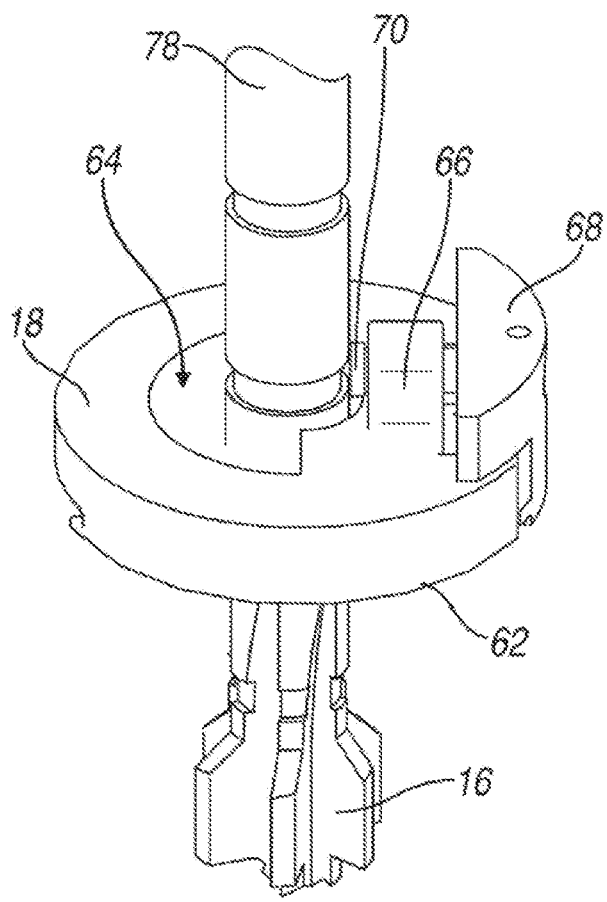
FIG. 4
FIG. 5

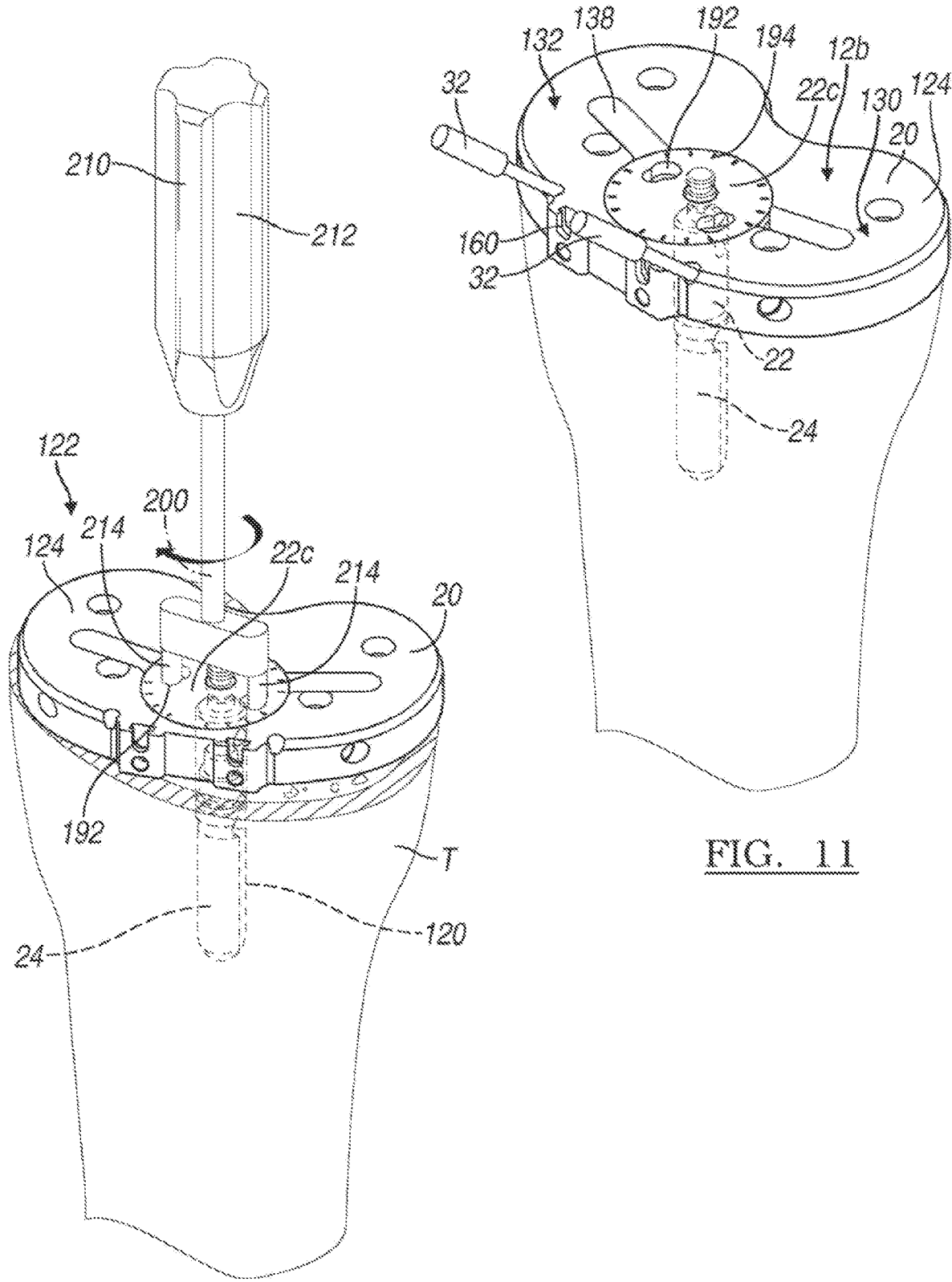

METHOD AND APPARATUS FOR IMPLANTING A KNEE PROSTHESIS

CROSS-REFERENCE TO RELATED APPLICATION

This application is a continuation of U.S. patent application Ser. No. 13/153,983 filed on Jun. 6, 2011, the entire disclosure of which is incorporated herein by reference

FIELD

The present disclosure relates generally to instruments for preparing a tibia and femur for knee joint prostheses and more particularly to instruments and related methods for using the instruments to prepare a tibia and femur for receipt of a revision knee joint prosthesis.

BACKGROUND

This section provides background information related to the present disclosure which is not necessarily prior art.

A knee joint prosthesis typically comprises a femoral component and a tibial component. The femoral component and the tibial component can be designed to be surgically attached to the distal end of the femur and the proximal end of a tibia, respectively. The femoral component can further be designed to cooperate with the tibial component in simulating the articulating motion of an anatomical knee joint. Such knee joint prostheses are generally referred to as primary knee prostheses.

Knee joint prostheses, in combination with ligaments and muscles, attempt to duplicate natural knee motion, as well as absorb and control forces generated during the range of flexion. In some instances, however, it may be necessary to replace an existing prosthesis. Such replacement prostheses are generally referred to as revision knee prostheses. Depending on the degree of damage or wear of the primary knee prosthesis, knee tendons and ligaments, however, it may be necessary for a revision knee joint prosthesis to eliminate one or more of these motions in order to provide adequate stability. In this regard, it may be desirable to provide a cruciate retaining (CR) revision knee, a fully constrained revision knee, a posterior stabilized (PS) revision knee or a hinged revision knee for example. Furthermore, in some instances, it may be necessary to account for bone loss in areas adjacent to such knee joint prostheses.

SUMMARY

This section provides a general summary of the disclosure, and is not a comprehensive disclosure of its full scope or all of its features.

A method for preparing a femur for receiving a prosthesis can include positioning an intramedullary (IM) member in the femur. A femoral trial component can be positioned onto a distal end of the femur. The femoral trial component can have an attachment portion, an articulating surace and at least two cut surfaces thereon. A modular boss assembly can be attached to the attachment portion of the femoral trial component. The modular boss assembly can have a boss stem that is configured to operably connect to the IM member. A desired contact between the femoral trial component and the distal femur can be confirmed based on the attaching. The femoral trial component can be fixed to the distal femur based on the confirming. The modular boss assembly can be removed from the femoral trial component. A reamer bushing can be coupled relative to the femoral trial component. A cavity can be reamed into the femur using the reamer bushing as a guide. At least one of a modular femoral box trial and a stem adapter can be coupled relative to the femoral trial component. All of the steps including removing the modular boss assembly, coupling the reamer bushing, reaming the cavity and coupling the modular femoral box trial and stem adapter are performed while the femoral trial component remains fixed to the distal femur.

According to additional features, attaching the modular boss assembly can include selecting the modular boss assembly from a plurality of modular boss assemblies each having a boss stem that extends along a distinct offset axis. Coupling the reamer bushing can comprise selecting a reamer bushing from a plurality of reamer bushings each having a throughbore that is offset a distance that corresponds to the offset axes of the boss stems. The reamer bushing can be selected based on the selected modular boss assembly. Attaching the modular boss assembly can comprise locating a distal connection plate of the modular boss assembly onto a recessed portion of the femoral trial component. Fasteners can be advanced through passages defined through the distal connection plate and into threadable engagement with the femoral trial component and the attachment portion. According to other features, attaching the modular boss assembly can further comprise rotating the boss stem around a long axis defined through the distal connection plate until a desired orientation is attained relative to the IM member. Posterior stabilized (PS) box cuts can be prepared on the femur using the cut guide surfaces of the femoral trial component. Medial and/or lateral cuts can be prepared through a corresponding one of medial and lateral cut slots defined in the femoral trial component for receipt of a distal femoral augment. According to one example, coupling the reamer bushing can include attaching a positioning ring to the attachment portion, inserting a reduced diameter portion of the reamer bushing into the positioning ring, rotating the reamer bushing about its longitudinal axis until the throughbore is aligned at a desired location, and fixing the reamer bushing from further rotating.

According to still other features, attaching the positioning ring can include advancing fasteners through passages defined through the positioning ring into threadable engagement with the femoral trial component at the attachment portion. Fixing the reamer bushing from further rotating can include advancing a peg associated with the positioning ring into a corresponding locating bore defined in the reduced diameter portion of the reamer bushing. The modular femoral box trial can be coupled to the first attachment portion of the femoral trial component. A stem adapter can be coupled to the modular femoral box trial. The stem adapter can have an offset that corresponds to an offset of the modular boss stem.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

The present disclosure will become more fully understood from the detailed description and the accompanying drawings, wherein:

FIG. 4 is a perspective view of an intramedullary (IM) reamer stop slidably coupled to a reamer;

FIG. 5 is a detailed perspective view of the reamer stop of FIG. 4;

FIG. 10 is an anterior perspective view of the tibial template and offset coin of the instruments illustrated in FIG. 1 shown with the tibial template resting atop the tibial plateau while the offset coin is rotated relative to a locating stem with a positioning tool to determine the tibial offset;

FIG. 11 is an anterior perspective view of the tibial template and offset coin subsequent to determining the preferred offset and removing of the positioning tool and with pins located through apertures of the tibial template to secure the tibial template to the proximal tibia;

Corresponding reference numerals indicate corresponding parts throughout the several views of the drawings.

DETAILED DESCRIPTION

Example embodiments will now be described more fully with reference to the accompanying drawings. While the following discussion is directed toward instruments and related methods for performing revision surgery, the same may be used as part of a primary knee replacement procedure.

Figure 1:
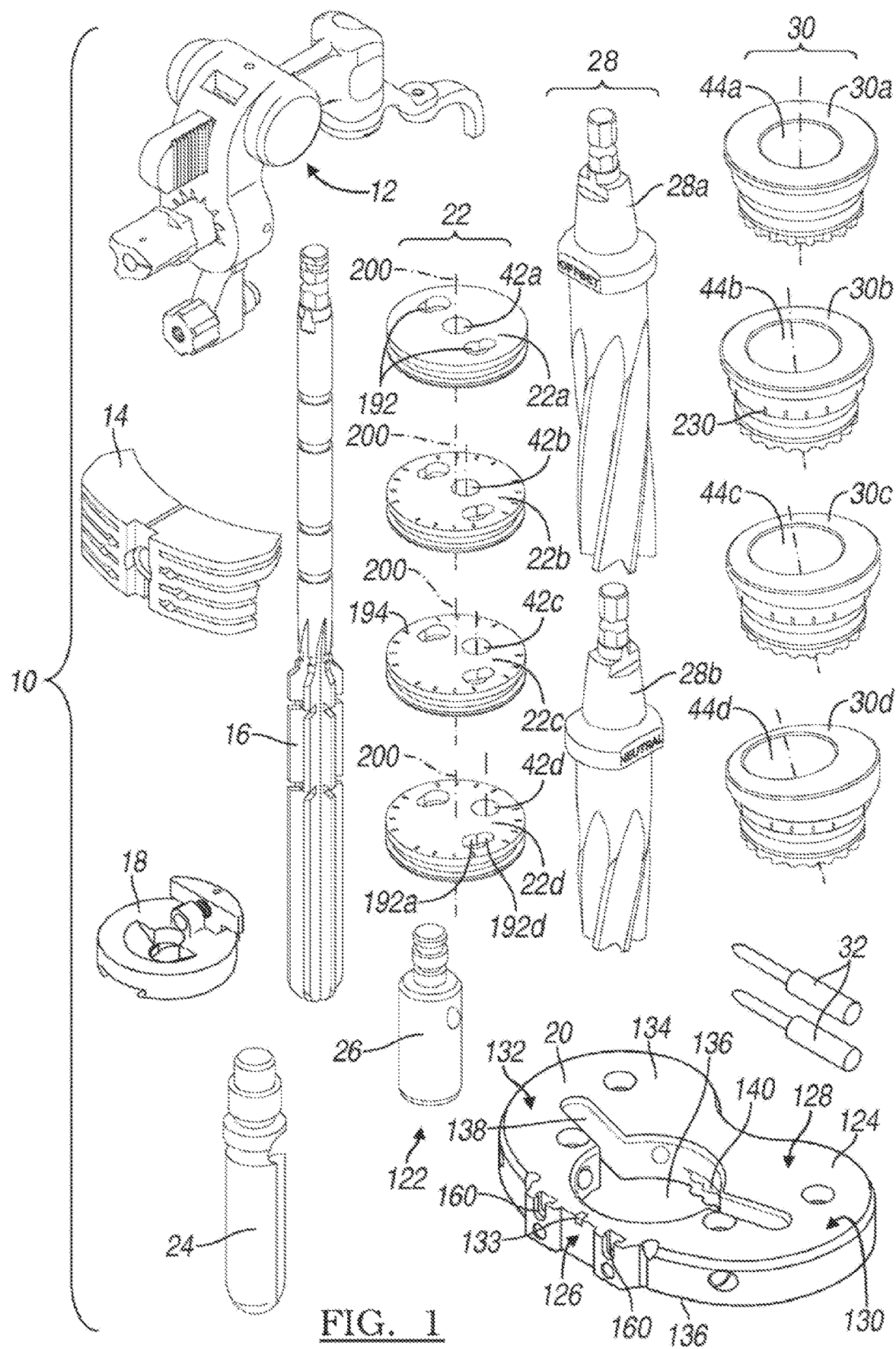
FIG. 1 is a perspective view of various instruments used for preparing a tibia for receipt of a tibial prosthesis according to various examples of the present teachings.

With initial reference to FIG. 1, a system or kit of tools or instruments for tibial preparation are shown and generally identified at reference numeral 10. In general, the kit of tools 10 can comprise a tibial resection guide 12, a resection block 14, a reamer 16, and an intramedullary (IM) reamer stop 18. The kit of tools 10 can further comprise a tibial template 20, a series of positioning coins or offset adaptors collectively referred to at reference numeral 22, a locating stem 24, a stem adapter 26, a pair of reamers collectively referred to at reference numeral 28, a series of reamer sleeves collectively referred to at reference numeral 30 and a pair of pins collectively referred to at reference numeral 32. In general, the tibial resection guide 12 and resection block 14 can be located relative to the reamer 16 for preparing various horizontal cuts, such as medial and lateral cuts on the proximal tibia as will be described herein. The positioning coins 22, individually identified at reference numerals 22a, 22b, 22c and 22d, each have bores 42a, 42b, 42c and 42d, respectively. The positioning coins 22a, 22b, 22c and 22d can be selectively and intraoperatively coupled to the stem adapter 26 and locating stem 24 and rotated within a locating bore 36 of the tibial template 20 to determine a desired tibial offset as will be described.

The reamer sleeves 30, individually identified at reference numerals 30a, 30b, 30c and 30d, can each have throughbores 44a, 44b, 44c and 44d that have centers that correspond to, or are concentric with, the respective bores 42a, 42b, 42c and 42d of the positioning coins 22. The reamer sleeves 30 can also be positioned into the locating bore 36 of the tibial template 20 at a rotational orientation that matches the orientation determined with the positioning coins 22. The reamer sleeves 30 can then be used to guide the appropriate reamers 28 when preparing a cavity in the proximal tibia for receipt of a tibial implant.

Figure 2:
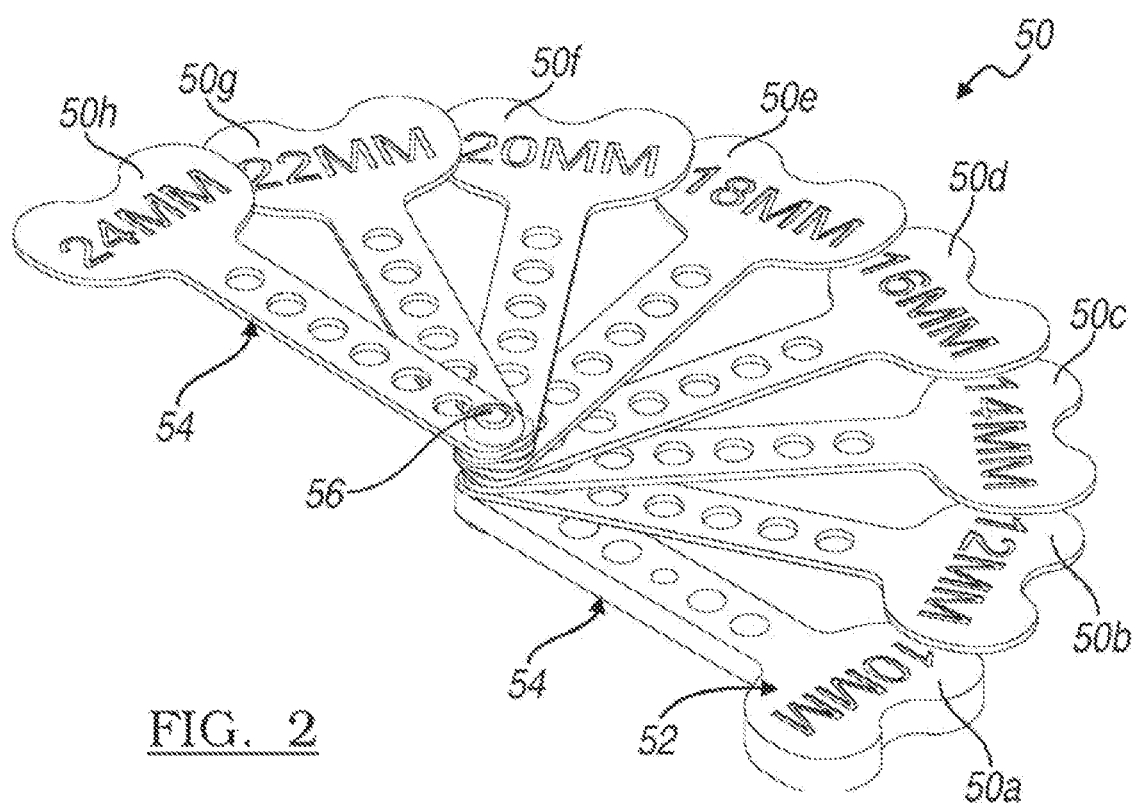
FIG. 2 is a perspective view of a tibial spacer assembly according to the present teachings.
Figure 3:
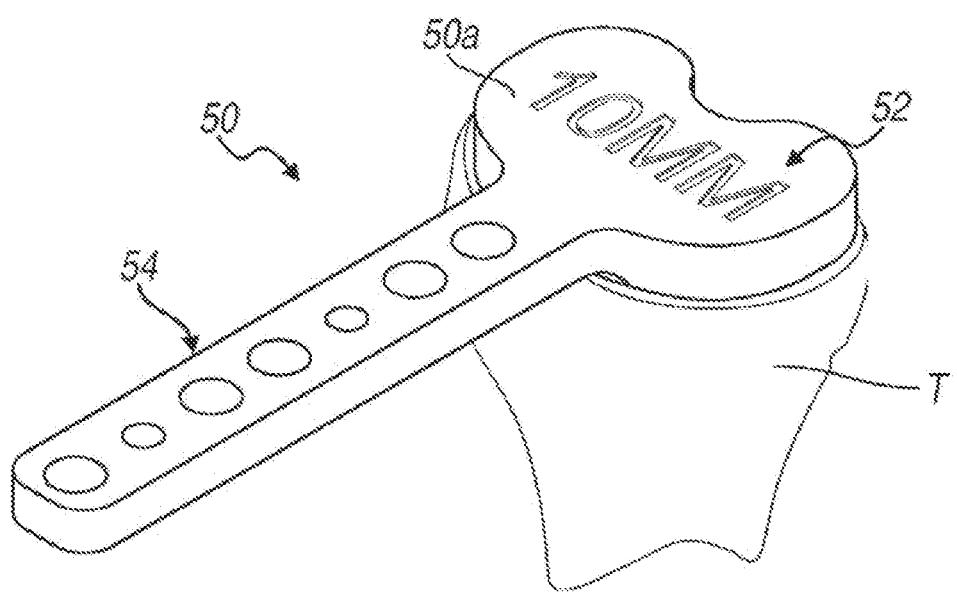
FIG. 3 is a perspective view of one of the tibial spacers of the tibial spacer assembly in FIG. 2 located atop a resected proximal end of a tibia to assist in determining a joint line.

Turning now to FIGS. 2 and 3, a tibial spacer assembly 50 is shown. In the depicted example, tibial spacers 50a, 50b, 50c, 50d, 50e, 50f, 50g and 50h are provided. The tibial spacer 50a has a thickness of 10 mm. According to the example shown, the tibial template 20 can also have a thickness of 10 mm such that the tibial spacer 50a or the tibial template 20 can alternatively be used when determining a desired thickness of a tibial bearing. The remaining tibial spacers 50b-50h each have a thickness of 2 mm. The tibial spacer assembly 50 can be stacked, as needed, to achieve a desired height. The thickness of a given stack of tibial spacers 50a-50h (or just the tibial spacer 50a used alone) represents a desired thickness of a tibial bearing that will be implanted at the proximal tibia. In the examples shown, the tibial spacer 50b can be stacked onto the tibial spacer 50a to collectively define a thickness of 12 mm.

As can be appreciated, the tibial spacers 50a-50h can be sequentially stacked to achieve additional increments of 2 mm. The tibial spacer 50c represents (e.g., the cumulative thickness of the tibial spacer 50c, the tibial spacer 50b and the tibial spacer 50a) a thickness of 14 mm. The tibial spacer 50d represents a thickness of 18 mm. The tibial spacer 50f represents a thickness of 20 mm. The spacer 50g represents a thickness of 22 mm. The spacer 50h represents a thickness of 24 mm. In other embodiments, other thicknesses of the tibial spacer assembly 50 and the individual spacers 50a-50h are contemplated. As shown, the respective spacers 50a-50h can each include a tibial plateau portion, collectively referred to by reference numeral 52, and a handle portion, collectively referred to by reference numeral 54. Each of the tibial spacers 50a-50h can be rotatably connected at terminal ends by way of a fastener 56. The respective tibial spacers 50a-50h can each pivotally rotate about the fastener 56 in order to isolate a desired tibial spacer 50a-50h from the remainder of the spacers 50a-50h. It can be appreciated that while the respective tibial spacers 50a-50h are shown attached to each other through a fastener 56, they may alternatively be unattached, separate pieces.

The tibial spacer assembly 50 can be used to find the joint line of a tibia T using anatomical landmarks. More specifically, the tibial plateau portion 52 of a given tibial spacer 50a-50h can be placed atop the tibial plateau of the tibia T or atop the resected proximal end of the tibia. In other words, the primary tibia is removed and the selected spacer 50a-50h can be positioned on the previously resected proximal tibia. In the depicted embodiment, the spacers 50a-50h are universal and can accommodate a left or a right tibia. The appropriate joint line will be confirmed when the proper thickness spacer 50a-50h is placed on the tibial plateau and presents a desired height (i.e., superiorly from the tibial plateau) relative to anatomical landmarks. At this time, a thickness of optional, supplemental augments, such as those disclosed in currently pending and commonly owned U.S. patent application Ser. No. 12/248,517, filed Oct. 9, 2008, incorporated by reference herein in its entirety, can be determined. It can be appreciated that it may be necessary to provide supplemental augments on any combination of the medial and lateral sides of the tibia T. The joint line, or where the tibia T and femur F (FIG. 34) meet, is known once the desired thickness of the identified spacer 50a-50h and the augmentation need is confirmed and noted. In some examples, the host femur or femoral trial may be located relative to the selected spacer 50a, etc., to confirm the thickness. The spacer assembly 50 is then removed from the tibia T.

Figure 6:
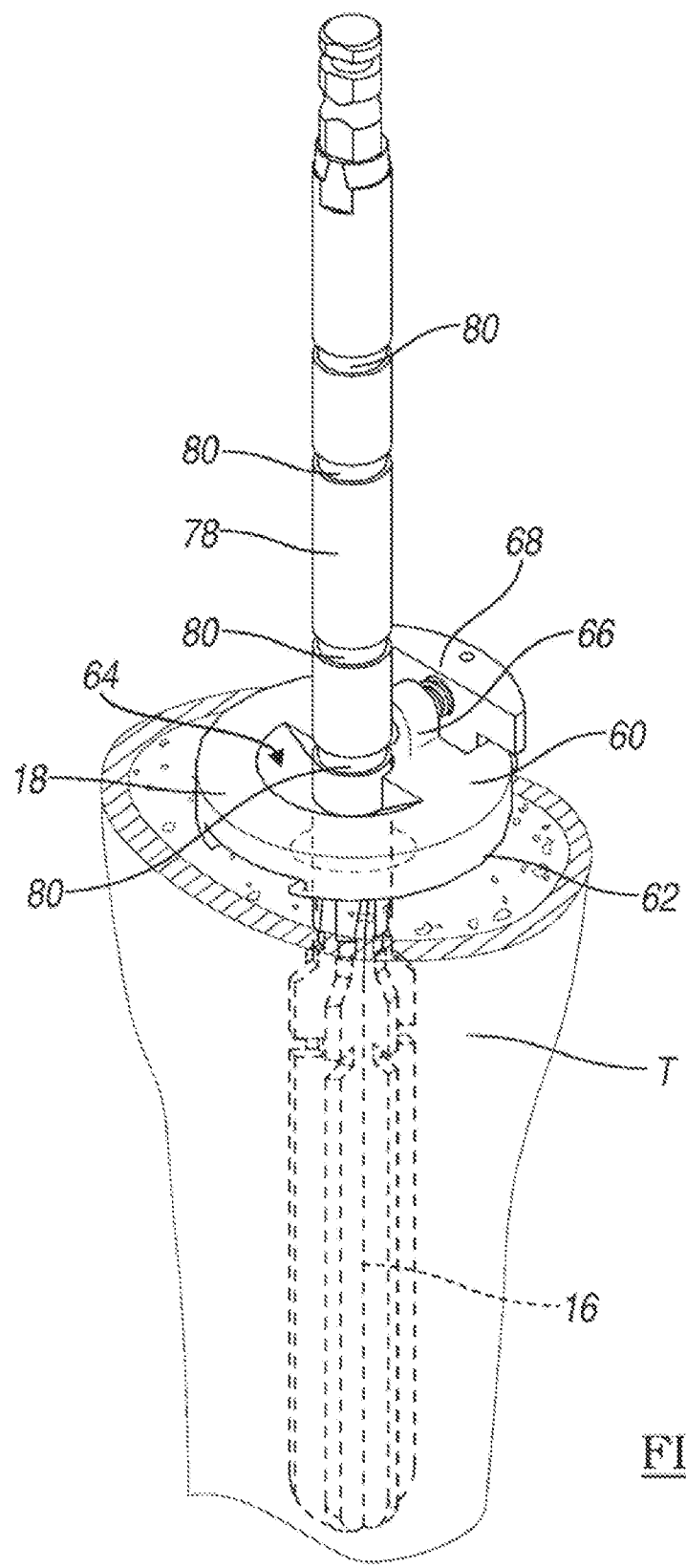
FIG. 6 is a perspective view of the IM reamer stop engaging a proximal tibia while the reamer is preparing the IM canal of the tibia.

With further reference now to FIGS. 4-6, additional features will be described. Once the joint line has been determined relative to the tibia T, the IM reamer stop 18 can be coupled to the reamer 16. The reamer 16 can cooperate with the IM reamer stop 18 to prepare the IM canal of the tibia T. During use, the reamer 16 is able to ream a distance into the IM canal until the reamer stop 18 comes into contact with the proximal tibia.

The IM reamer stop 18 and the reamer 16 will now be described in greater detail. The IM reamer stop 18 can have a superior surface 60 and an inferior surface 62. The IM reamer stop 18 can define an opening 64 that extends through the IM reamer stop 18 from the superior surface 60 to the inferior surface 62. A finger support 66 can be supported on the superior surface 60 of the IM reamer stop 18. A button 68 can be coupled to a locating finger 70. The locating finger 70 can be movably fixed to the finger support 66. In one example, the locating finger 70 can move (e.g., such as by depression of the button 68) along an axis that is substantially transverse to an axis defined by the reamer 16. In one example, a biasing member 74, such as a spring in the depicted embodiment can bias the locating finger 70 into engagement with the reamer 16.

The reamer 16 can have a reamer shaft 78 that includes a plurality of annular grooves, collectively referred to a reference numeral 80 formed thereon. As can be appreciated, the grooves 80 can provide a nesting location for the locating finger 70 to control the depth of reaming for the reamer 16. According to one example, the groove 80 can be marked with indicia (not specifically shown) that identify various depths of reaming for the tibia T (as will become appreciated from the following discussion, the reamer 16 and the IM reamer stop 18 can also be used for preparation of the IM canal in the femur). In this regard, the grooves 80 can also correspond to various depths of reaming in the femur as well.

For exemplary purposes, the grooves 80 can correspond to 40 mm, 80 mm, 200 mm and other depths of reaming to correspond to a desired stem length. As can be appreciated, the various depths of cut can correspond to various lengths of tibial stems, such as a tibia stem 82 illustrated in FIG. 22. It can also be appreciated in some instances it may also be necessary to implant an offset adapter, such as the offset adapter 83 illustrated in FIG. 22 for example. In those instances where an offset adapter is needed in conjunction with a stem, the grooves 80 will correspond to different lengths of stem. For example, if a 40 mm offset adapter will be used, the groove that corresponds to an 80 mm tibial stem will also correspond to a 40 mm tibial stem with a 40 mm tibial offset adapter. Those skilled in the art can appreciate that the dimensions described herein are merely exemplary. In this regard, grooves can be provided in any combination of configurations along the reamer 16 for identifying a depth of reaming that can accommodate any combination of stems and/or offset adapters as necessary.

With specific reference now to FIG. 6, use of the reamer 16 and reamer stop 18 relative to a tibia T will be described. In some examples, various reamers 16 having distinct diameters can be used until adequate cortical contact is achieved in the tibia T. Multiple IM reamer stops 18 can be provided, each being operatively connected to a reamer 16 having a distinct diameter. In this way, a surgeon, when switching to a reamer having a larger diameter, can simply remove the combination of reamer 16 and IM reamer stop 18 and utilize another collective set of reamer and IM reamer stop. As can be appreciated, this can minimize the amount of time that may be required to remove a reamer 16 from the opening 64 in an IM reamer stop 18 and replace it with a reamer having another diameter.

Figure 7:
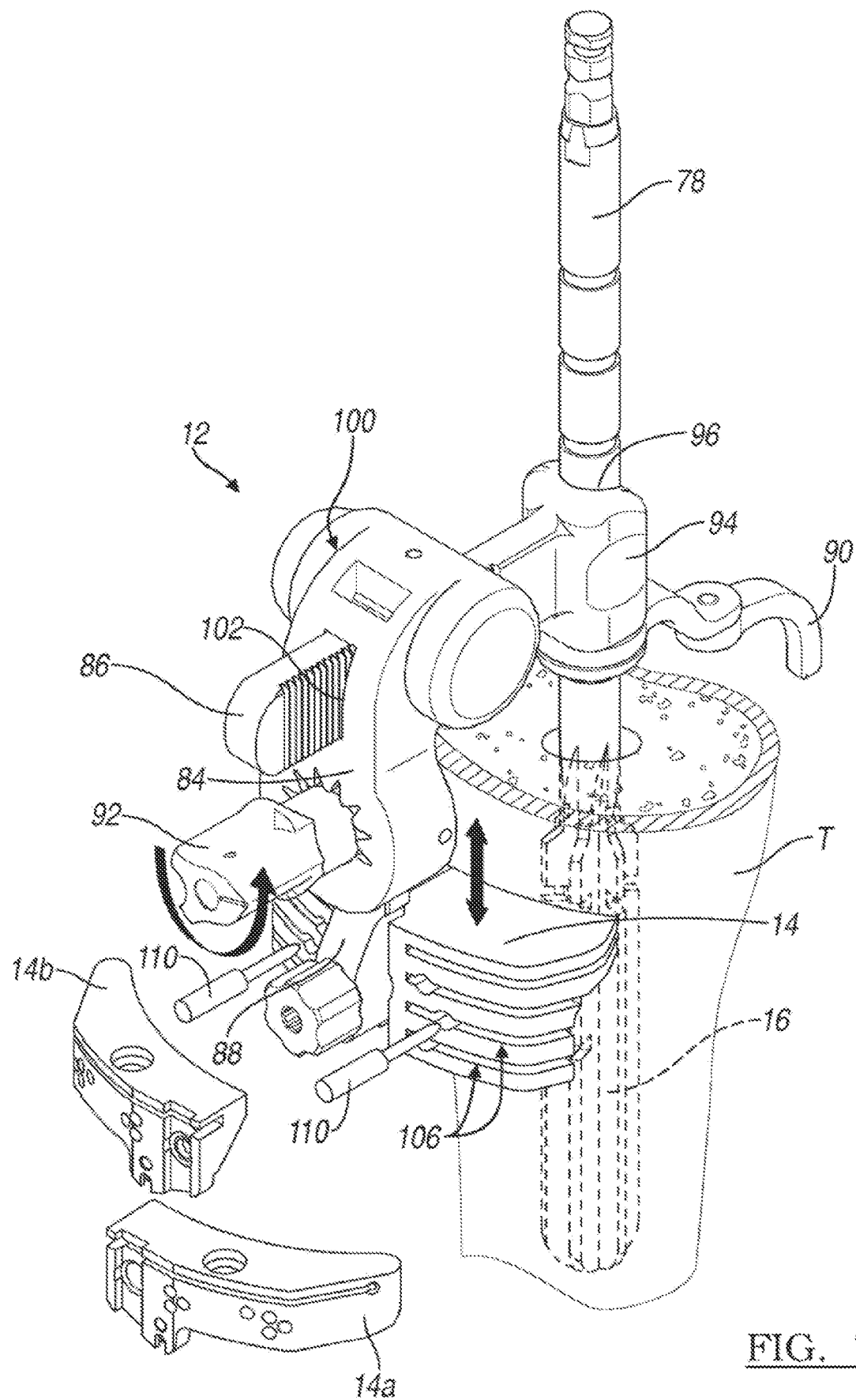
FIG. 7 is a perspective view of an IM tibial resection guide cooperating with the reamer shaft.

Once the IM canal of the tibia has been sufficiently prepared, as shown in FIG. 6, the IM reamer stop 18 can be removed from the reamer 16. The reamer 16 can remain in the IM canal. At this point, the reamer 16 can be securely retained in a fixed position by the cortical bone of the tibia T and act as an IM guide. Next, as illustrated in FIG. 7, the tibial resection guide 12 can be slid over the reamer 16. The tibial resection guide 12 can generally comprise a body 84, an adjustment arm 86, a block arm 88 and a stylus or finger 90. The body 84 can include a resection level adjustment knob 92. The adjustment arm 86 can include a hub 94 that has a passage 96 formed therethrough. The passage 96, as shown, can slidably receive the reamer shaft 78 of the reamer 16. The finger 90 can be used to engage the posterior tibia T. A coupler 100 can adjustably secure the adjustment arm 86 through a slot 102 formed through the body 84. The resection block 14 can then be secured to the block arm 88. The resection block 14 can define a series of slots 106 on a medial and lateral side. In various embodiments, a trial stem (not shown) may be inserted into the IM canal in order to act as a positioning reference in place of the reamer 16.

The body 84 can be adjusted along the adjustment arm 86 to position the resection block 14 against the tibia T. The resection level adjustment knob 92 can be rotated to place the resection block 14 at a desired level (i.e., relative to a proximal surface of the tibia T). In other words, the resection block 14 can be moved inferiorly/superiorly on the anterior side of the tibia T until the desired location is attained. Once the desired location of the resection block 14 has been achieved, the resection block 14 can be fixed to the tibia T (such as by pins 110). The remainder of the IM tibial resection guide 12 along with the reamer 16 can be removed. According to other examples, a medial resection guide 14a and/or a lateral resection guide 14b can be used in place of the resection block 14.

Figure 8:
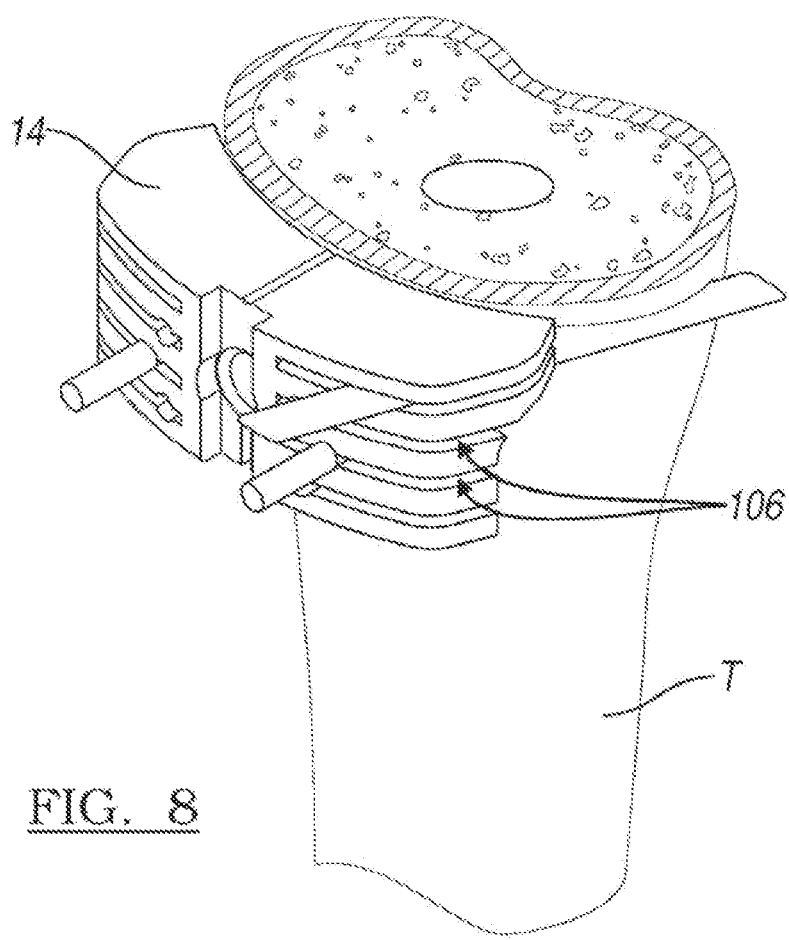
FIG. 8 is a perspective view of a resection block pinned to the tibia while a saw locates through one of the slots in the resection block while a horizontal cut is made in the tibia for receipt of a medial tibial augment.
Figure 9:
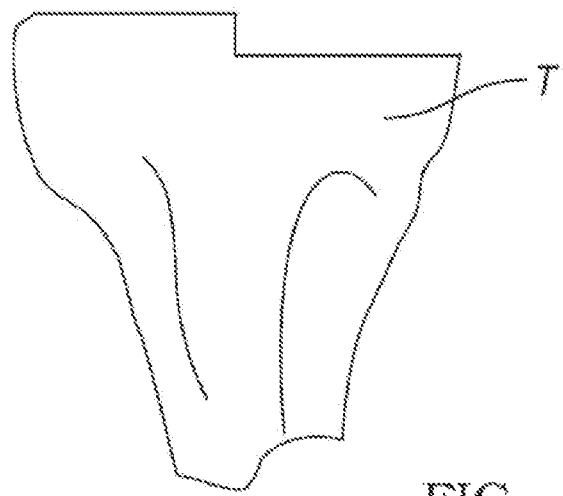
FIG. 9 is an anterior view of the tibia of FIG. 8 subsequent to the horizontal cut and a vertical cut made on the proximal tibia for receipt of the medial tibial augment.
Figure 34:
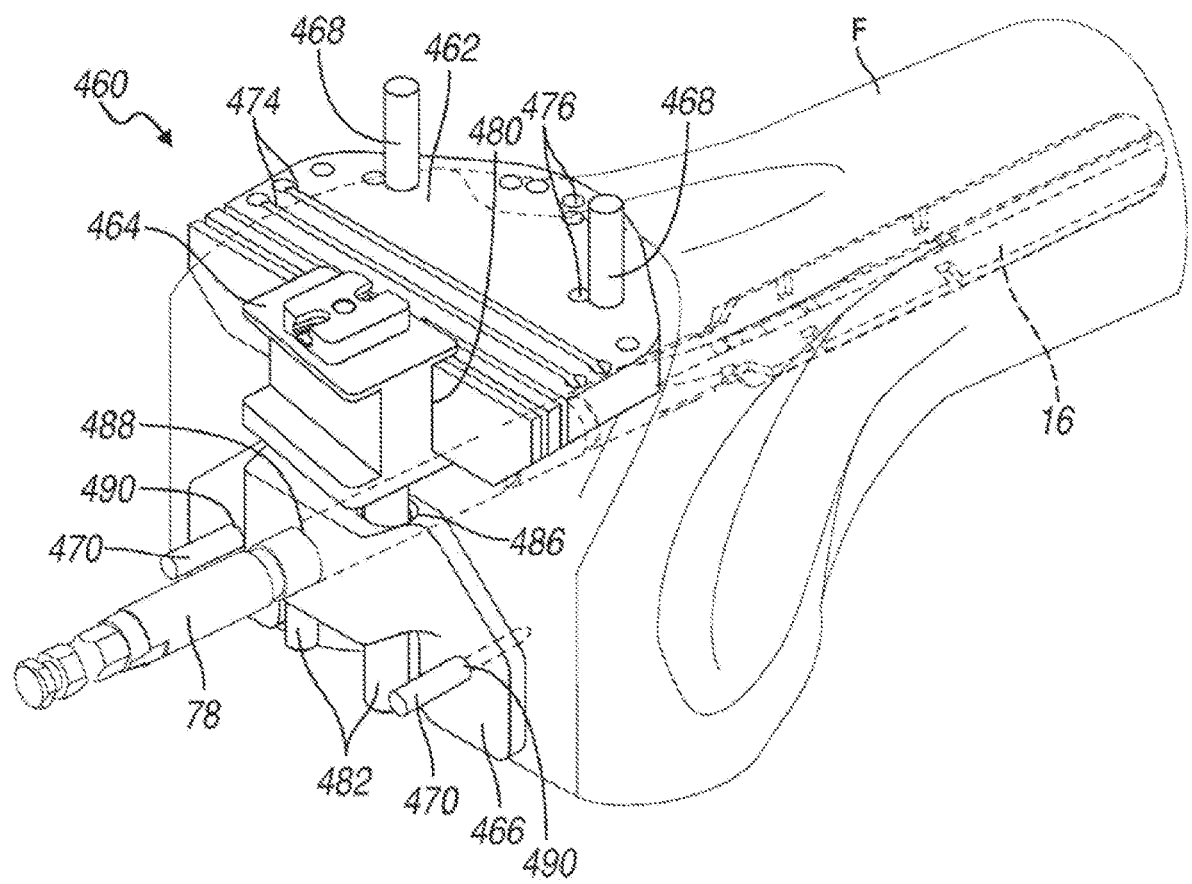
FIG. 34 is an anterior perspective view of the femoral cut guide positioning assembly located onto a distal femur and positioned relative to the reamer shaft.
Figure 35:
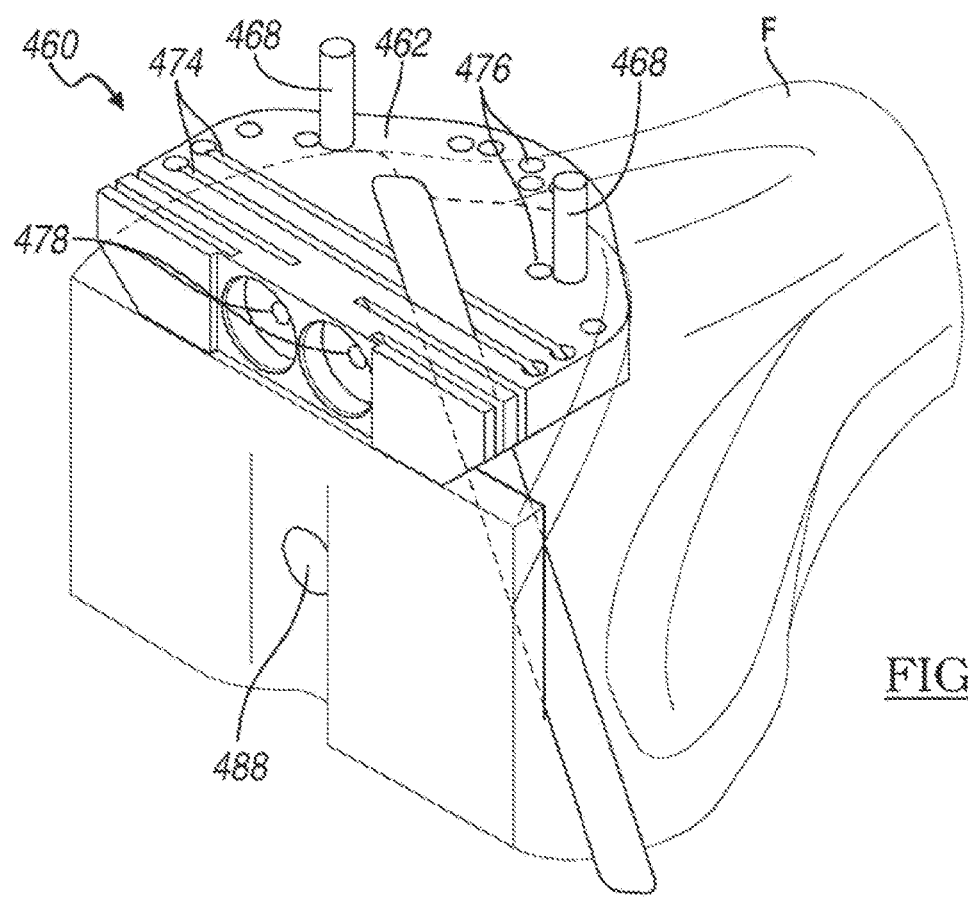
FIG. 35 is an anterior perspective view of a distal cut block of the femoral cut guide positioning assembly pinned to a distal femur and shown with a saw preparing a horizontal cut for accommodating a medial augment.

With reference now to FIGS. 7-9, an exemplary sequence for preparing the proximal tibia for receipt of a 5 mm medial augment and a 10 mm lateral augment will now be described. It can be appreciated that the medial/lateral cuts can be made to accommodate any tibial augment, such as those disclosed in currently pending and commonly owned U.S. patent application Ser. No. 12/248,517, filed Oct. 9, 2008 which is expressly incorporated herein by reference. The resection level of the tibial resection guide 12 can be set by rotating the resection level adjustment knob 92 to the desired position. In one example, rotation of the resection level adjustment knob 92 can adjust the block arm 88 between a distance of zero and 8 mm along a longitudinal axis of the block arm 88, which moves the cutting slots 106 in the resection block 14 a certain distance from the top of the stylus or finger 90 in the direction of the longitudinal axis of the block arm 88. It can be appreciated that the resection level adjustment knob 92 can be configured to adjust the block arm 88 to other distances. It can further be appreciated that other tibial resection guides may be used. Once the resection level is set, a clean-up cut can be made through the proximal most (or 0 mm) slot of the slots 106 on the medial side of the resection block 14. Similarly, a cut can be made through the second proximal-most (or 5 mm) slot of the slots 106 on the lateral side of the resection block 14. An exemplary tibia is shown in FIG. 9 after cutting, subsequent to using the resection block 14. It will be appreciated that the depths of cut described above are merely exemplary. Those skilled in the art will appreciate that a depth of cut will be made that is consistent with the joint line determined as described above that can accommodate a thickness of a given bearing, such as bearing 114 illustrated in FIG. 22. Once the proximal tibia has been prepared using the resection block 14, the resection block 14 can be removed from the tibia T. Other methods for cutting the tibia for accommodating an augment are discussed herein (FIGS. 34 and 35). In some examples, the tibial spacers 50 (or portions thereof) can be used to fill the void left on the proximal tibia to provide a flat surface for accommodating the tibial template 20. In other examples, shims or trial augments (such as disclosed in currently pending and commonly owned U.S. patent application Ser. No. 12/248,517 identified above) may be used to fill the void.

With reference now to FIGS. 1 and 10-16, the offset position of the prepared IM canal 120 of the tibia T will be determined using a tibial offset positioning assembly 122. The tibial offset positioning assembly 122 can generally comprise the tibial template 20, the positioning coins 22, the locating stem 24 and the stem adapter 26. Prior to describing an exemplary method for using the tibial offset positioning assembly 122, additional features of the tibial template 20, positioning coins 22, locating stem 24 and stem adapter 26 will be described in greater detail. The tibial template 20 can generally include a body 124 having an anterior portion 126, a posterior portion 128, a medial portion 130 and a lateral portion 132. In the particular example shown, the medial and lateral portions 130 and 132 are arbitrarily named as the tibial template 20 can be interchangeably used for either a right or a left knee. The tibial template 20 can further include a mark or notch 133 formed thereon. The locating bore 36 can be formed through the body 124 from a superior surface 134 to an inferior surface 136 (FIG. 1). The body 124 can define a pair of radial slot passages 138.

A ledge 140 can be formed on at least a partial circumference of the body 124 at the locating bore 36. The ledge 140 can further include a first plurality of interface teeth 142. The body 124 can also define a series of lateral bores 144a, 144b and 144c (FIG. 12) radially extending from a center of the bore 36. According to one example, the bores 144a, 144b and 144c can be formed from an exterior surface 148 of the body 124 to the locating bore 36. Each of the bores 144a, 144b and 144c can have a spring biased ball assembly 150a, 150b and 150c, respectively therein. Each of the spring biased ball assemblies 150a, 15b and 150c can include a biasing member 152a, 152b and 152c that bias a ball 154a, 154b and 154c in a direction toward the locating bore 36 for cooperating with the respective positioning coins 22 as will be described. According to one example, each of the bores 144a, 144b and 144c can include stops 158a, 158b and 158c therein that capture the respective springs 152a, 152b and 152c. According to some examples, the bores 144a, 144b and 144c can be stepped, such that the respective stops 158a, 158b and 158c can be advanced to a location where the stepped bores transition to a reduced diameter. It is further appreciated that the bores 144a, 144b and 144c have a diameter less than the balls 154a, 154b and 154c near the locating bore 36 at a retaining wall (identified at reference 159a, FIG. 13) to capture the respective balls 154a, 154b and 154c in the body 124 of the tibial template 20. Other configurations are contemplated. The anterior portion 126 of the body 124 can include a pair of circumferential recesses 160.

Figure 14:
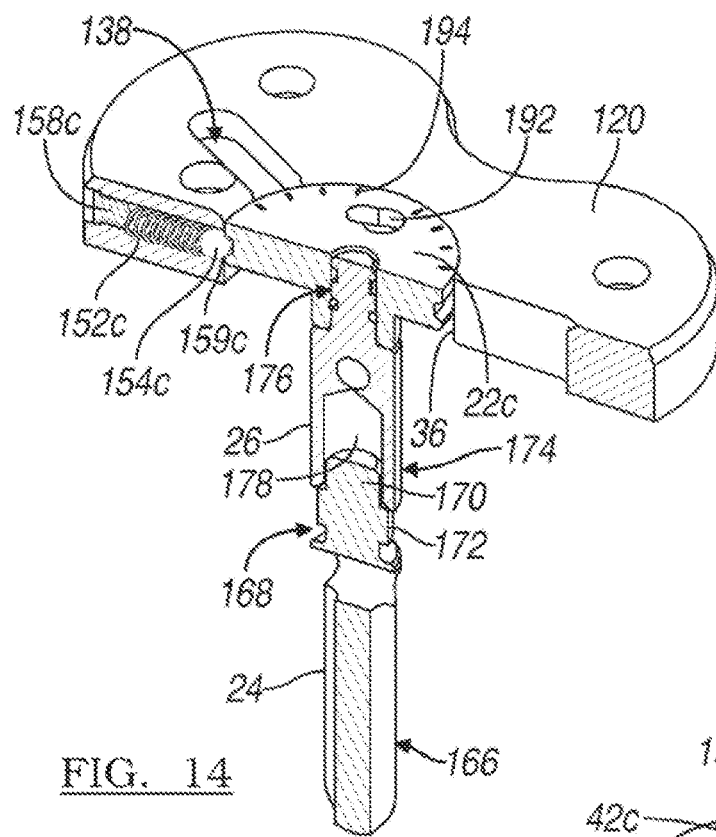
FIG. 14 is a cross-sectional view taken along line 14-14 of FIG. 13 and shown with a stem adapter and locating stem coupled to the offset coin.
Figure 15:
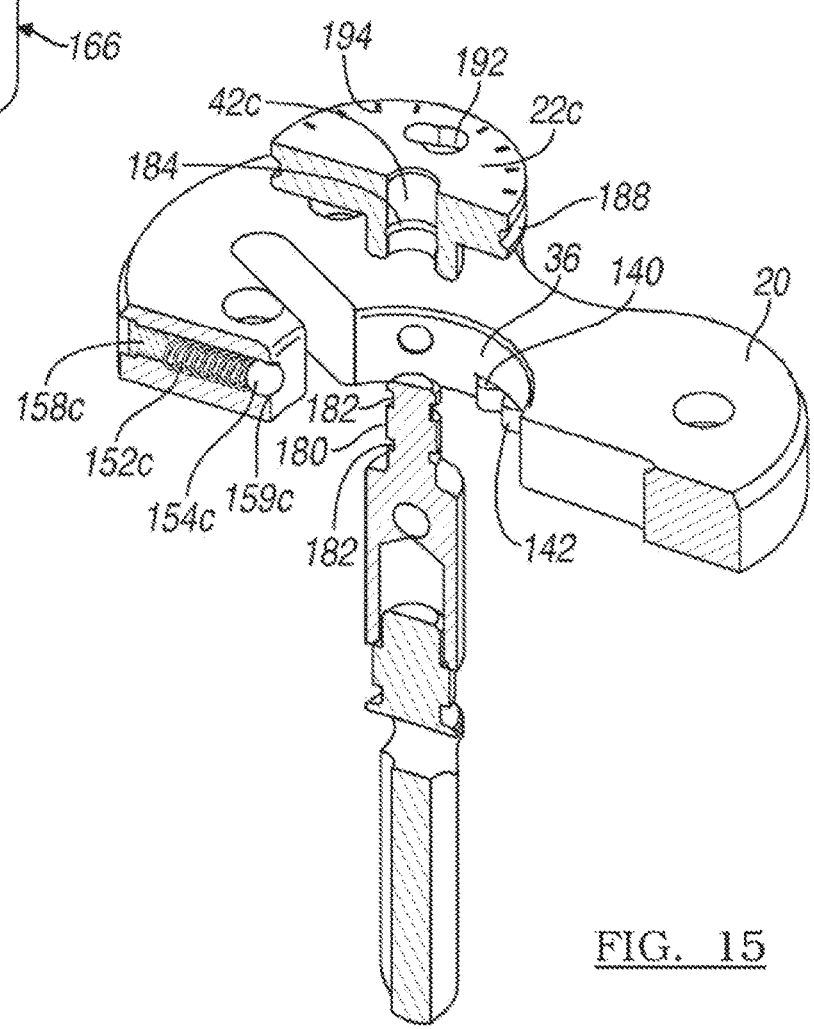
FIG. 15 is a cross-sectional view of the tibial template, stem adapter and locating stem of FIG. 14 and shown with the offset coin exploded.

The locating stem 24 can generally include a distal end 166 and a proximal end 168 (FIG. 14). The proximal end 168 can include a hub 170 and a collar 172 formed thereon. The stem adapter 26 can generally include a distal end 174 and a proximal end 176. The distal end 174 can define a blind bore 178 therein. The proximal end 176 can include a projection portion 180 (FIG. 15). A pair of circumferential grooves 182 can be formed around the projection portion 180. As will be described herein, the hub 170 of the locating stem 24 can be configured to locate into the blind bore 178 of the stem adapter 26. Similarly, the projection portion 180 of the stem adapter 26 can be configured to be received by a bore (such as the bore 42c) of a positioning coin 22 (such as the positioning coin 22c)

Figure 16:
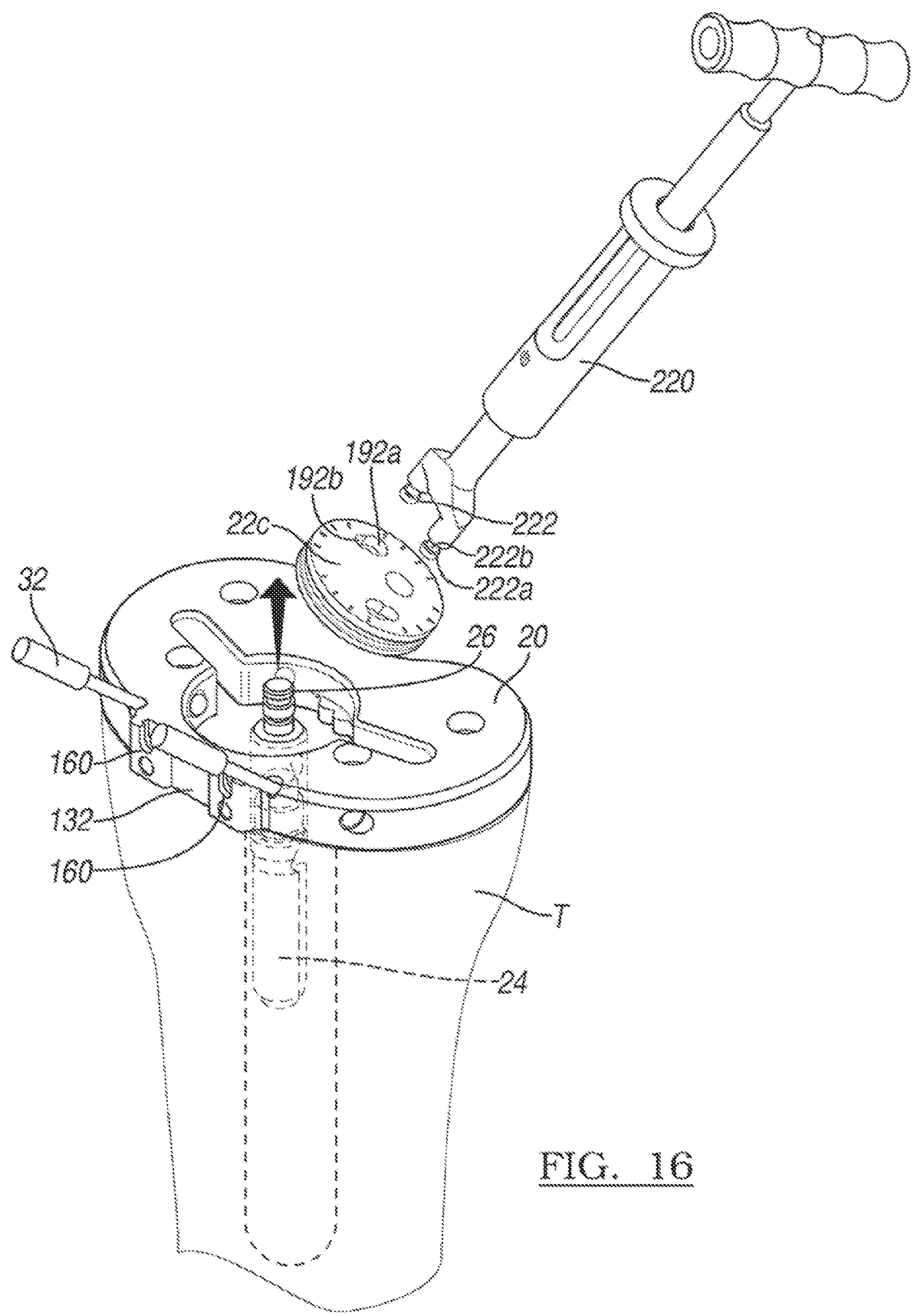
FIG. 16 is an anterior perspective view of the tibial template pinned to the proximal tibia in the desired location and with the offset coin being removed from the stem adapter with a removal tool.

With specific reference now to FIG. 1, the positioning coins 22 will be described in greater detail. In general, the positioning coins 22 can generally provide a disc-like shape and each have a circumferential groove 188 formed therearound. Similarly, each of the positioning coins 22 can include a pair of locating apertures 192. The locating apertures 192 can each have a first diameter portion 192a and a second diameter portion 192b. The second diameter portion 192b can have a diameter less than the first diameter portion 192a for interfacing with a removal tool (FIG. 16). Each of the positioning coins 22b, 22c and 22d can also include indicia 194 thereon. The positioning coins 22 can include a neutral positioning coin 22a (zero offset), an offset positioning coin 22b (2.5 mm offset), an offset positioning coin 22c (5 mm offset) and an offset positioning coin 22d (7.5 mm offset). The positioning coins 22 can each define the throughbores 42a, 42b, 42c and 42d, respectively that are offset a distance from a longitudinal axis of the center of the positioning coins 22, collectively identified at reference numeral 200.

With reference now to FIGS. 14 and 15, according to one example, a surgeon can couple the locating stem 24 to the stem adapter 26 by inserting the hub 170 of the locating stem 24 into the blind bore 178 of the stem adapter 26. At this point, the surgeon can select one of the positioning coins 22 that would appear to have a suitable offset for cooperating with the prepared IM canal 120 (FIG. 10). In the example shown in FIGS. 10-16, the surgeon has selected the positioning coin 22c (having the 5 mm offset). It will be appreciated however that the surgeon may need to intraoperatively switch between the positioning coins 22 until the appropriate offset (recognizing that zero offset may be used with the positioning coin 22a) has been selected. According to one example, the projection portion 180 of the stem adapter 26 can be inserted into the bore 42c of the positioning coin 22c. In some examples, an annular projection 184 provided in the bore 42 can create an interference fit with the groove 182 in the stem adapter 26. An o-ring or other supplemental engaging member may also be positioned between the projection portion 180 and the bore 42c. The positioning coin 22c can then be advanced into the locating bore 36 of the tibial template 20 until the respective balls 154a, 154b and 154c locate into the circumferential groove 188 of the positioning coin 22c. As can be appreciated, the respective balls 154a can initially translate against the bias of the springs 152a, 152b and 152c, respectively until the groove 188 aligns for receipt of the respective balls 154a, 154b and 154c (FIG. 14). As can be appreciated, the respective balls 154a, 154b and 154c can be configured to ride along the groove 188 as the positioning coin 22c is rotated around the locating bore 36.

At this point, it is important to recognize that only the locating stem 24 is fixed (or substantially fixed) relative to the tibia T. The positioning coin 22c is able to rotate around its longitudinal axis 200 causing the tibial template 20 to move around the proximal tibia (FIG. 10). The positioning coin 22c can be rotated (e.g., by the surgeon) around its longitudinal axis 200 with a positioning tool 210. The positioning tool 210 can generally include a handle 212 and a pair of fork members 214. According to one example, the fork members 214 can be inserted into the first diameter portions 192a of the respective locating apertures 192 of the positioning coin 22c. The positioning coin 22c can be rotated (clockwise or counterclockwise) around the axis 200 until a position is attained in which the body 124 achieves optimal coverage over the proximal tibia T centered on cortical bone. Again, in some instances, the surgeon may need to swap out various positioning coins (such as positioning the positioning coins 22a, 22b and 22d) in order to attain the best possible coverage of the proximal tibia. Once the desired position on the proximal tibia is verified, the tibial template 20 can be fixed relative to the tibia T, such as by the pins 32 (FIG. 11). At this point, the surgeon can make a note of the indicia 194 relative to the mark 133 on the superior surface 134 of the tibial template 20. This will correspond to the tibia offset position or degrees offset. In some instances, it will be appreciated that no offset will be necessary (i.e., optimal coverage can be confirmed with the zero offset positioning coin 22a).

Once the tibial template 20 has been secured to the proximal tibia T with the pins 32, the positioning coin 22c can be removed from the stem adapter 26, such as with a removal tool 220. In one example, the removal tool 220 can have two fork portions 222 that have a first diameter portion 222a and a second diameter portion 222b. The second diameter portion 222b can have a diameter less than the first diameter portion 222a. The first diameter portion 222a can be advanced into the first diameter portion 192a of apertures 192. The removal tool 220 can then be rotated around its longitudinal axis, such that the second diameter portions 222b of the fork portions 222 locate into the second diameter portions 192b of the apertures 192. In this position, the first diameter portions 222a of the fork portions 222 can locate under an edge of the second diameter portion 192b or a ledge 226 of the coin 22c to transfer a pulling force on the positioning coin 22c. The stem adapter 26 and locating stem 24 can also be removed at this point.

Figure 12:
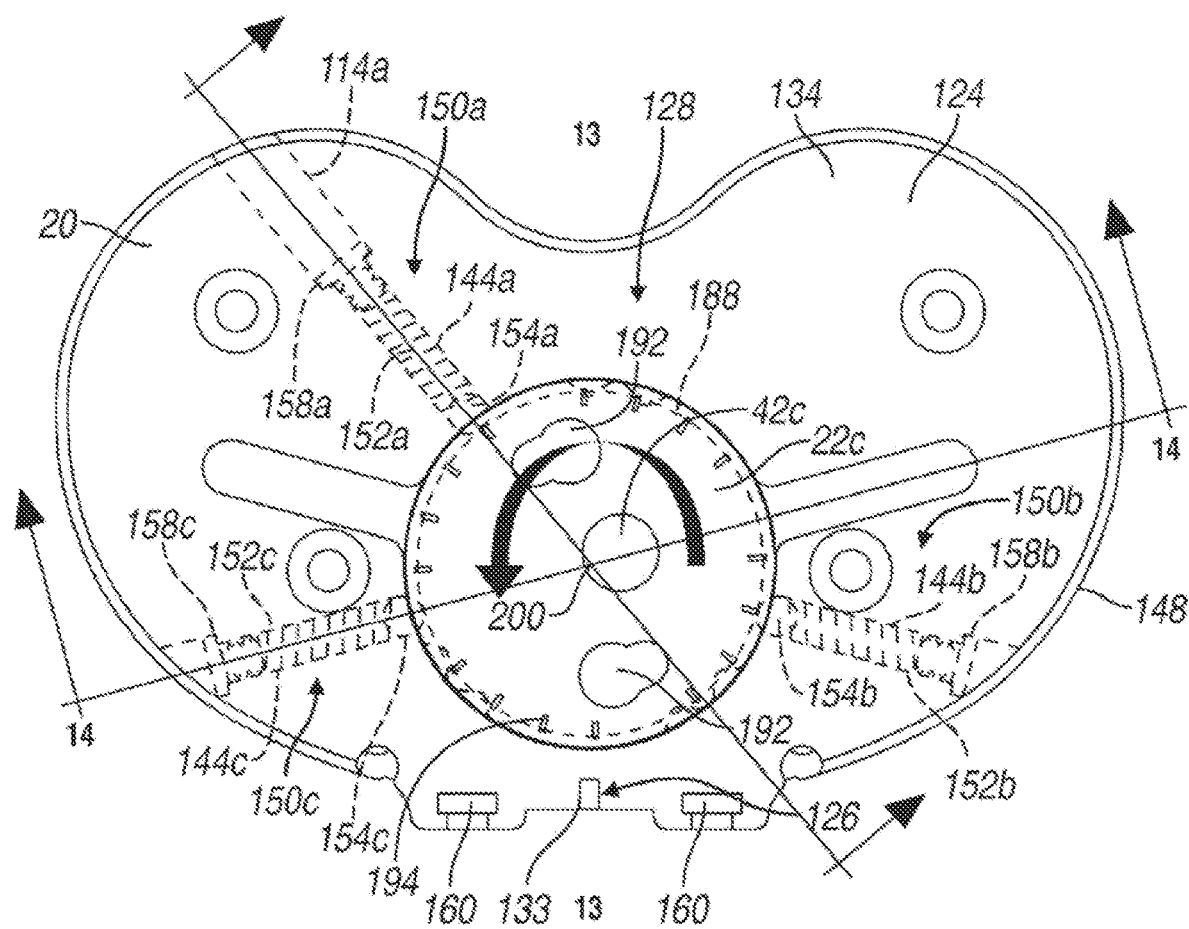
FIG. 12 is a plan view of the tibial template and offset coin of FIG. 10 and shown with a series of spring loaded spherical members locating into a circumferential groove of the offset coin according to one example of the present teachings.
Figure 13:
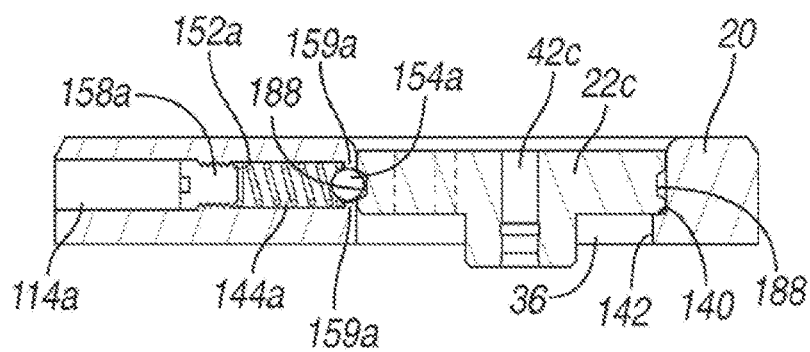
FIG. 13 is a cross-sectional view taken along lines 13-13 of FIG. 12.
Figure 17:
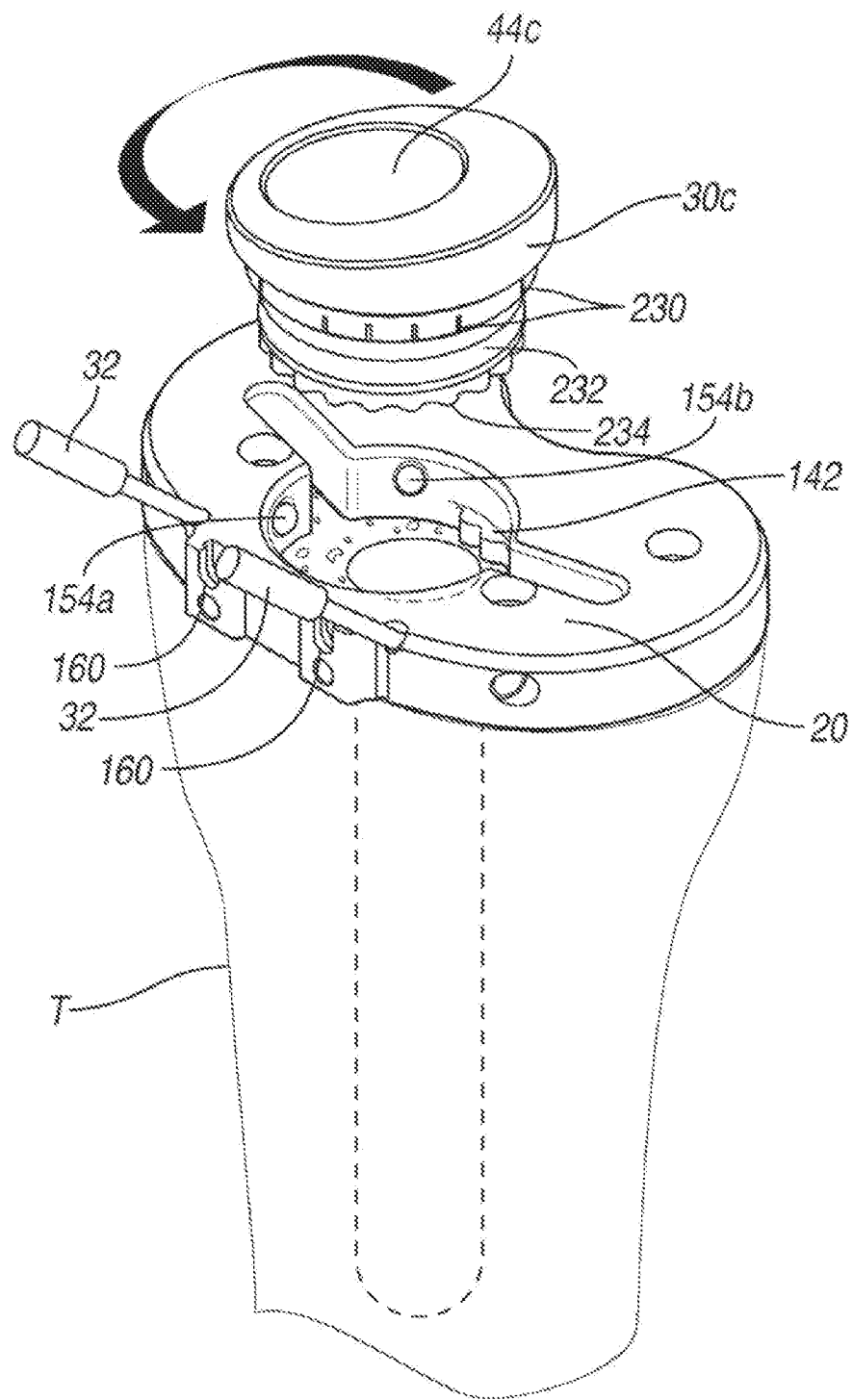
FIG. 17 is an anterior perspective view of the tibial template shown with an offset reamer bushing being aligned for receipt into alocating bore of the tibial template.
Figure 18:
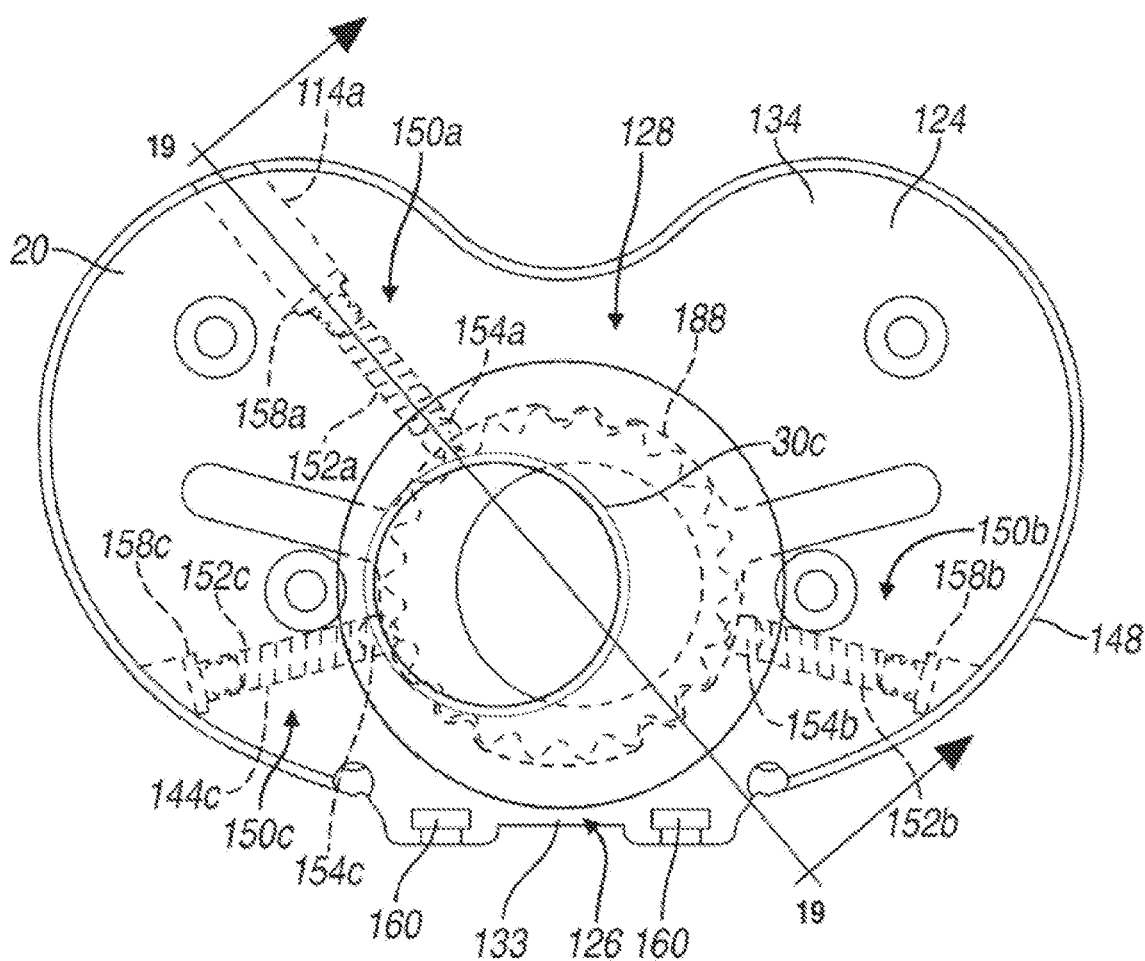
FIG. 18 is a plan view of the offset reamer bushing positioned into the locating bore at an orientation that corresponds with the radial offset of the selected offset coin and rotational orientation that corresponds to the indicia noted on the offset coin.
Figure 19:
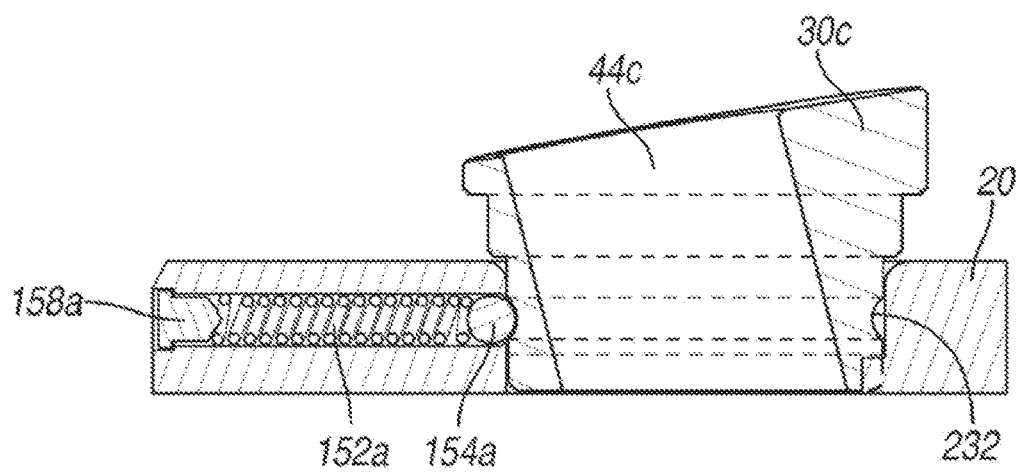
FIG. 19 is a cross-sectional view taken along lines 19-19 of FIG. 18 and illustrating the spring loaded member locating into a circumferential groove of the offset reamer bushing.

With reference now to FIGS. 17-19, additional features will be described. One reamer sleeve selected from the group of reamer sleeves collectively referenced by numeral 30 (FIG. 1) can then be located into the locating bore 36 of the tibial template 20. The collective reamer sleeves 30 can include the neutral reamer sleeve 30a (0 mm offset or neutral offset), the offset reamer sleeve 30b (2.5 mm offset), the offset reamer sleeve 30c (5 mm offset), and the offset reamer sleeve 30d (7.5 mm offset). As identified above, the reamer sleeves 30 can each define a throughbore 44a, 44b, 44c and 44d, respectively. As can be appreciated, each offset corresponds to a radial offset from the center of the sleeve or the longitudinal axis of the tibia T. Each of the reamer sleeves 30 can correspond to a respective positioning coin 22. In this regard, a surgeon can select an offset reamer sleeve 30 having a similar offset as the positioning coin 22 identified above. The reamer sleeves 30 can each define indicia 230 around its circumferential groove 232 (FIG. 19). A second plurality of interference teeth 234 can be formed around a circumference of the reamer sleeves 30. The surgeon can then rotationally align the indicia 230 of the reamer sleeve 30c to the mark 133 on the tibial template 20. It is important to recognize that the surgeon rotates (FIG. 17) the reamer sleeve 30c (prior to locating the reamer sleeve 30c into the locating bore 36 of the tibial template 20) in order to align a common indicia 230 of the reamer sleeve 30c with the same indicia 194 that was determined by the positioning coin 22c (FIG. 12). Once the reamer sleeve 30c has been rotated to the desired orientation, the reamer sleeve 30 can be advanced into the locating bore 36.

More specifically, the second plurality of interference teeth 234 can meshingly align with the first plurality of interference teeth 142. Concurrently, the respective balls 154a, 154b and 154c can locate into the circumferential groove 232 of the reamer sleeve 30c. As can be appreciated, the meshing engagement between the first plurality of interference teeth 142 and a second plurality of interference teeth 234 can inhibit rotational movement of the reamer sleeve 30c around its longitudinal axis. Concurrently, the interaction of the respective balls 154a, 154b and 154c with the circumferential groove 232 of the reamer sleeve 30c can inhibit the reamer sleeve 30c from coming out (axially) of the locating bore 36.

Figure 20:
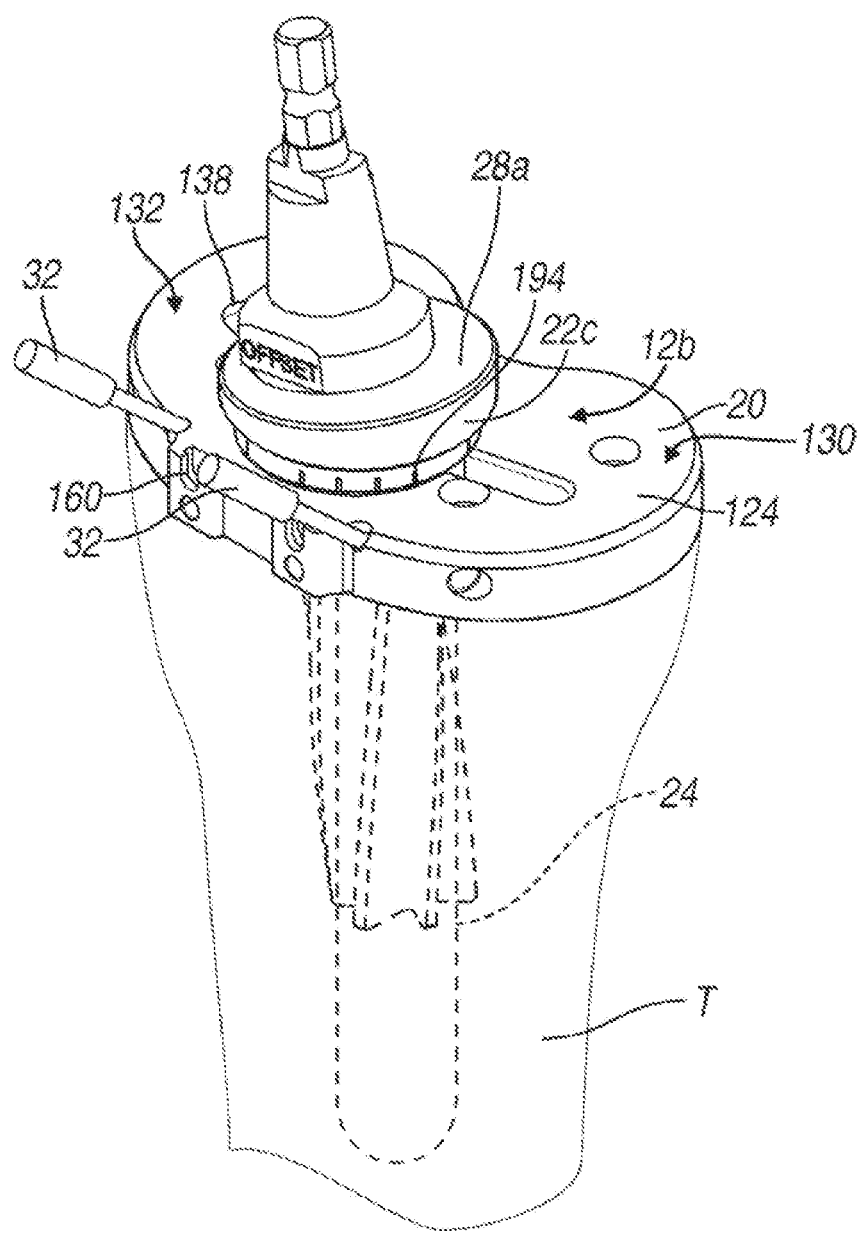
FIG. 20 is an anterior perspective view of the tibial template shown with an offset reamer of the instruments illustrated in FIG. 1 and located through the offset reamer bushing to prepare an offset cavity into the tibia for accommodating an implant boss and an offset adapter.
Figure 21:
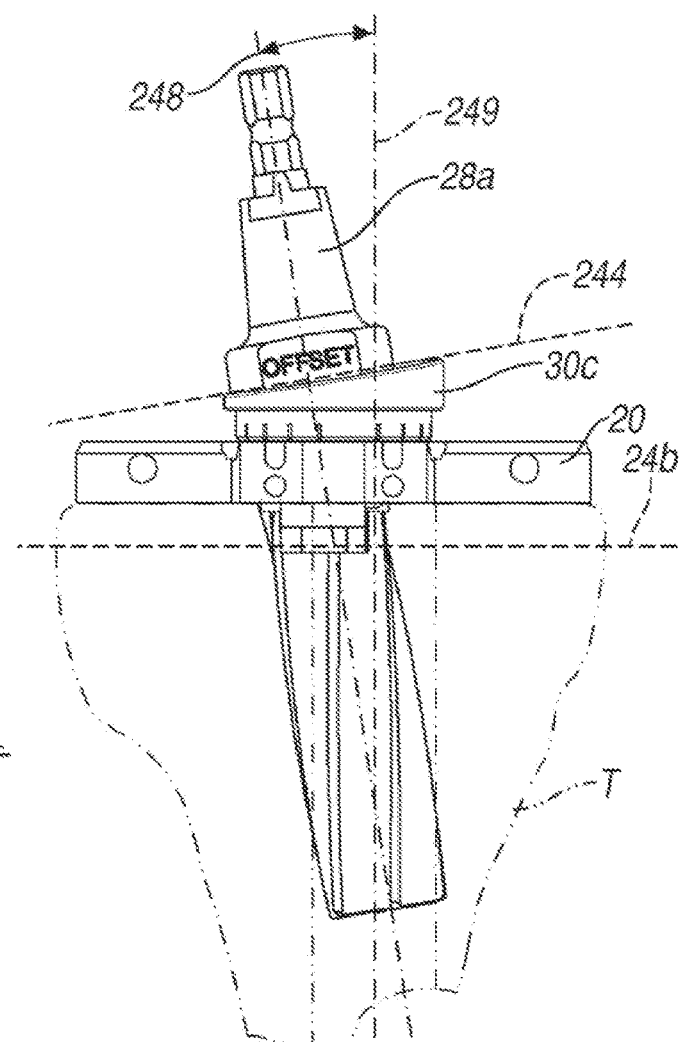
FIG. 21 is an anterior view of the tibial template, offset reamer bushing and offset reamer of FIG. 20.
Figure 22:
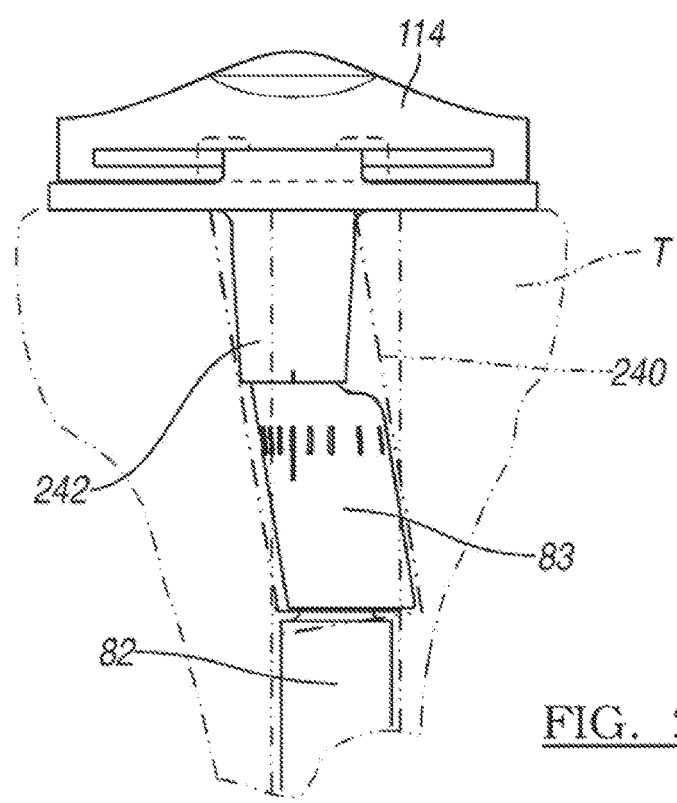
FIG. 22 is an anterior view of the tibia shown in FIG. 1 subsequent to preparation of the offset cavity and removal of the instruments and with an exemplary tibial component, offset adapter and tibial stem implanted with respect to the prepared tibia.

Turning now to FIGS. 20 and 21, once the offset reamer sleeve 30c has been advanced to the desired location, the offset reamer 28a is inserted through the throughbore 44c and an offset cavity 240 is reamed to accommodate an implant boss and an offset adapter (such as the boss 242 and offset adapter 83 shown in FIG. 22). Notably, as illustrated in FIG. 21, the offset reamer sleeve 30c has an upper plane 244 and a lower plane 246 that are non-parallel. As can be appreciated, the series of offset reamer sleeves 30 can be provided having various upper and lower planes that diverge at various distinct angles. As can be appreciated, each offset reamer sleeve 30 can correspond to an angle of reaming identified at reference 248 relative to the longitudinal axis 249 of the tibia T that will accommodate the profile of any offset adapter as needed (such as disclosed in U.S. patent application Ser. No. 12/248,517, filed Oct. 9, 2008 identified above) as illustrated in FIG. 22, the cavity 240 can accommodate the offset adapter 83.

In some examples, the neutral offset reamer sleeve 30a can be used in instances where an offset adapter is unnecessary. In such instances, the reamer 28b (FIG. 1) can be used to ream an opening in the proximal tibia.

Figure 23:
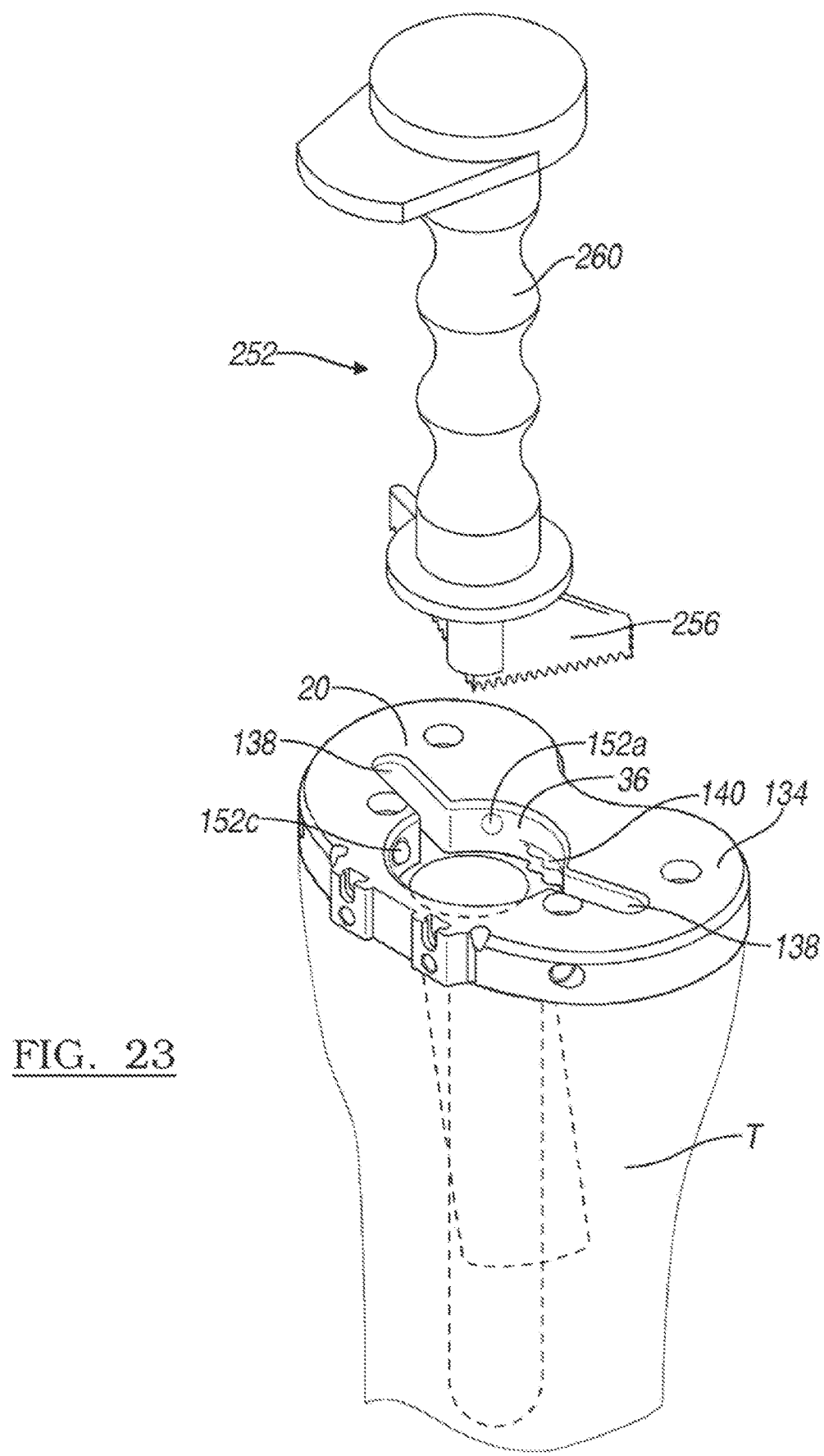
FIG. 23 is an anterior perspective view of the tibial template shown with a cruciate augment punch according to additional features.
Figure 24:
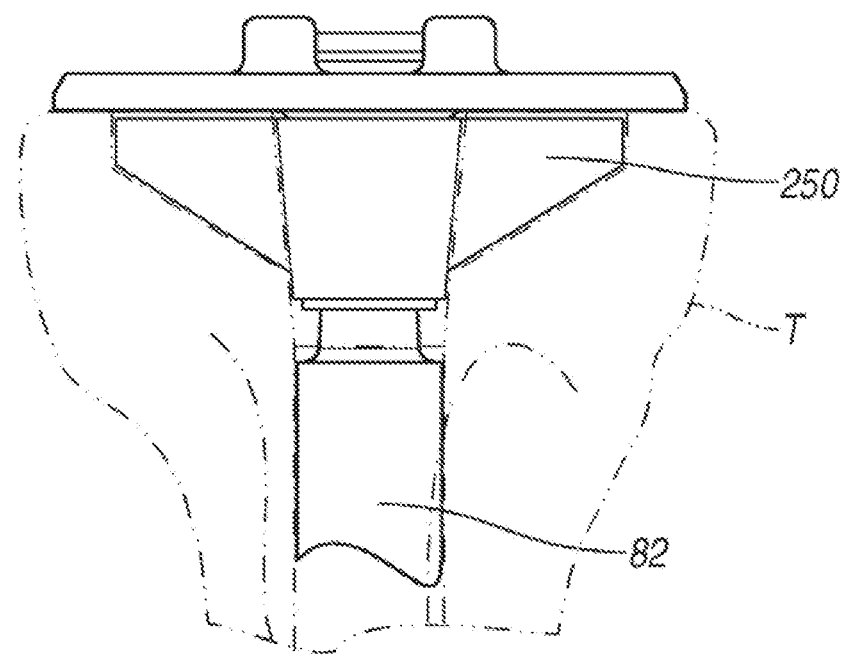
FIG. 24 illustrates a tibia that has been prepared with the cruciate augment punch of FIG. 23 for receipt of a winged augment and shown with the winged augment coupled between a tibial tray and tibial stem in an implanted position.

In examples where the tibia T must be prepared for receipt of a cruciate augment 250 (FIG. 24), a cruciate augment punch 252 (FIG. 23) can be passed through the locating bore 36 of the tibial template 20. More specifically, the punch 252 can have a winged plate with cutting teeth 256 that can pass through the slot passages 138 formed on the tibial template 20 while a surgeon grasps the ribbed handle portion 260. The surgeon can repeatedly axially drive the punch 252 through the locating bore 36 creating the complementary passages in the proximal tibia to receive the winged portions of the augment 250 as shown in FIG. 24.

Figure 25:
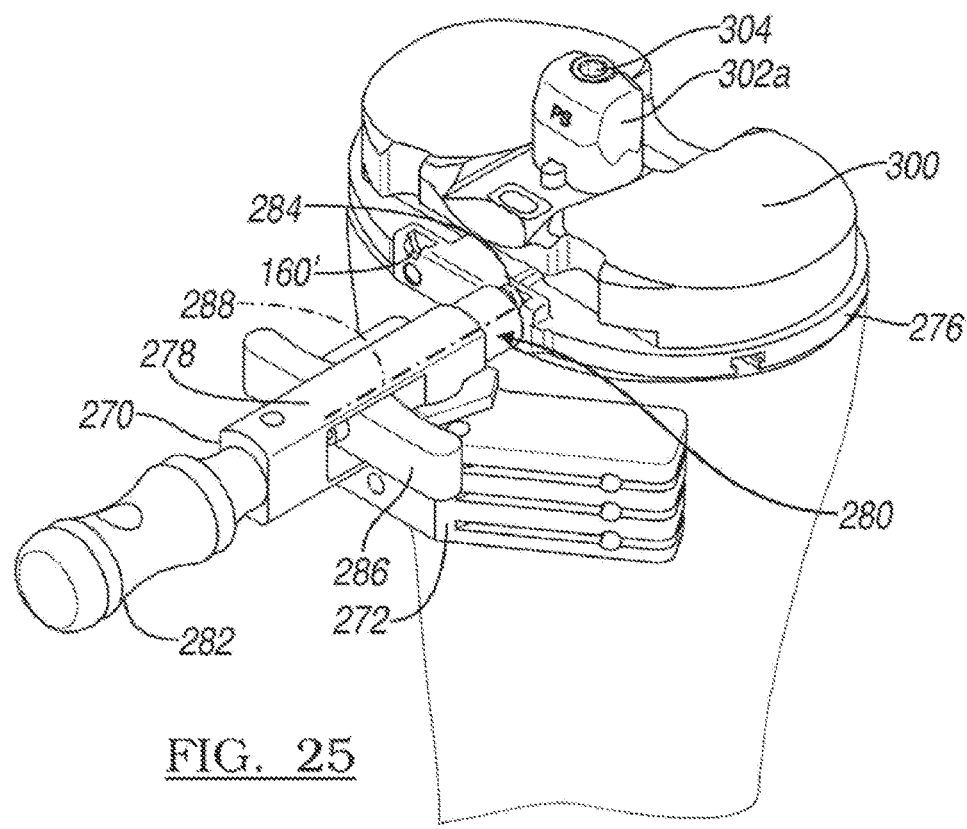
FIG. 25 is an anterior perspective view of a tibial augment resection block coupled to an anterior portion of a trial tibial tray shown with a trial tibial bearing attached to the trial tibial tray.
Figure 26:
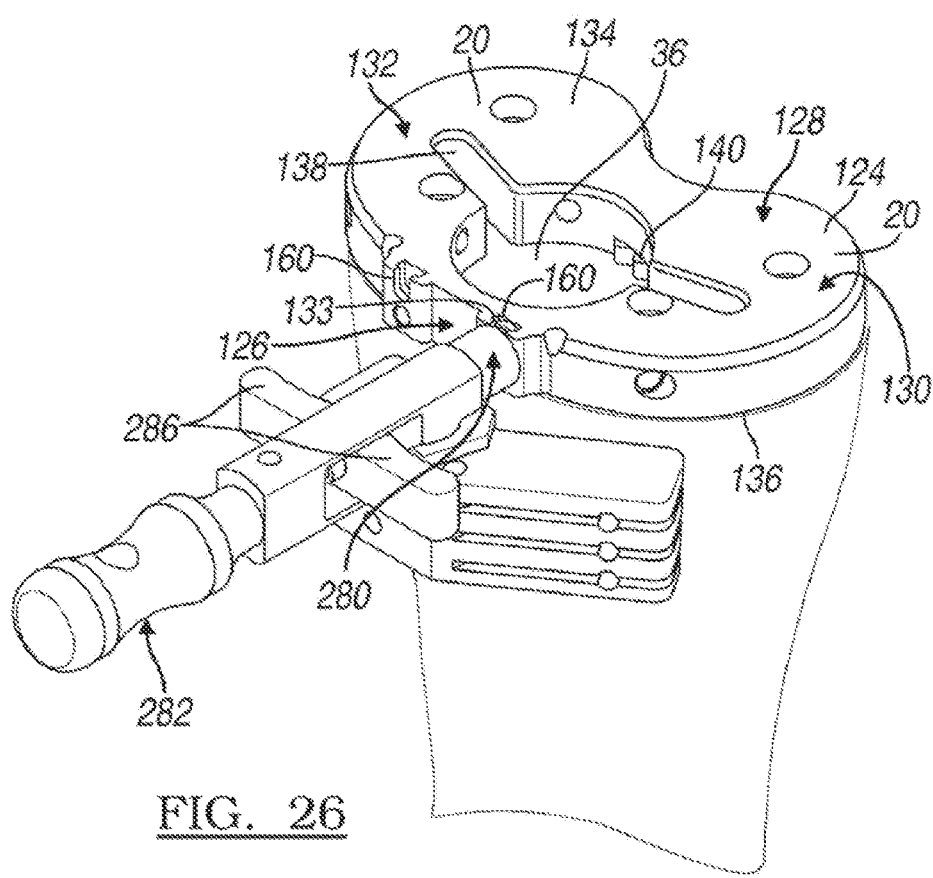
FIG. 26 is an anterior perspective view of the tibial augment resection block alternatively coupled to the tibial template according to other features.

With specific reference now to FIGS. 25-30, additional features of the instant disclosure will be described. Once the tibia T has been reamed for receipt of a tibial implant, trial tibial implants may be used to determine optimal sizes for the replacement tibial component and bearing (such as tibial component 242 and bearing 114, shown in FIG. 22). Additionally, at this point, it may be desirable to prepare horizontal cuts in the tibia, such as on the lateral and/or medial tibia for receipt of a tibial augment. In this regard, a tibial augment resection block locating tool 270 having a tibial augment resection block 272 can be selectively and alternatively coupled to the tibial template 20 (FIG. 26) or a trial tibial tray 276 (FIG. 25). The tibial augment resection block locating tool 270 can generally comprise a body portion 278 having a distal end 280 and a proximal end 282. The distal end 280 can generally comprise a distal engaging disc 284. A handle 286 can be mounted for movement along a longitudinal axis 288 of the body 278 of the tool 270. According to one example, a user can initially locate the distal engaging disc 284 into one of the circumferential recesses 160 provided on the tibial template 20 (FIG. 26) or alternatively one of the circumferential recesses 160' (FIG. 25) provided on the trial tibial tray 276. The tibial augment resection block 272 can then be used to make cuts in the tibia, such as medial cuts as shown in FIGS. 25 and 26 and/or lateral cuts.

Figure 29:
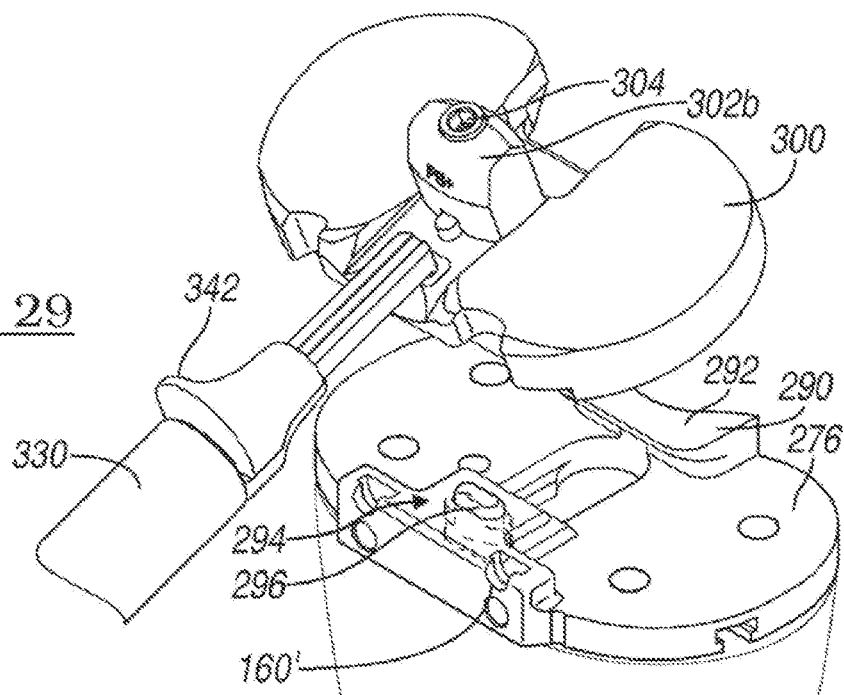
FIG. 29 is an anterior perspective view of the trial tibial bearing being removed from the trial tibial tray with the bearing removal tool.

The trial tibial tray 276 will now be described in greater detail with reference to FIG. 29. The trial tibial tray 276 can generally comprise a posterior catch portion 290 that includes a posterior lip 292 and an anterior engagement portion 294 that includes a locking button 296. The trial tibial tray 276 can be configured to selectively and intraoperatively receive a trial tibial bearing 300. It can be appreciated that while one trial tibial bearing 300 is shown in the drawings, a series of trial tibial bearings having various sizes and thicknesses will be provided. Similarly, a series of superiorly extending members 302a (FIG. 25), 302b (FIGS. 27 and 29) and 302c (FIG. 30) having various geometries according to one application can be configured to selectively couple to the trial tibial bearing 300 by way of a fastener 304.

According to various features, the trial tibial bearing 300 can be selectively coupled to the trial tibial tray 276 by initially locating a posterior catch 310 (FIG. 28) of the trial tibial bearing 300 under the posterior lip 292 of the posterior catch 290 and subsequently advancing an anterior end 312 toward the trial tibial tray 276. A lock 316 can initially and temporarily retract into the trial tibial tray 276 against the bias of a spring 320 that is retained within a bore 322 of the trial tibial tray 276 by a disc 324.

Figure 27:
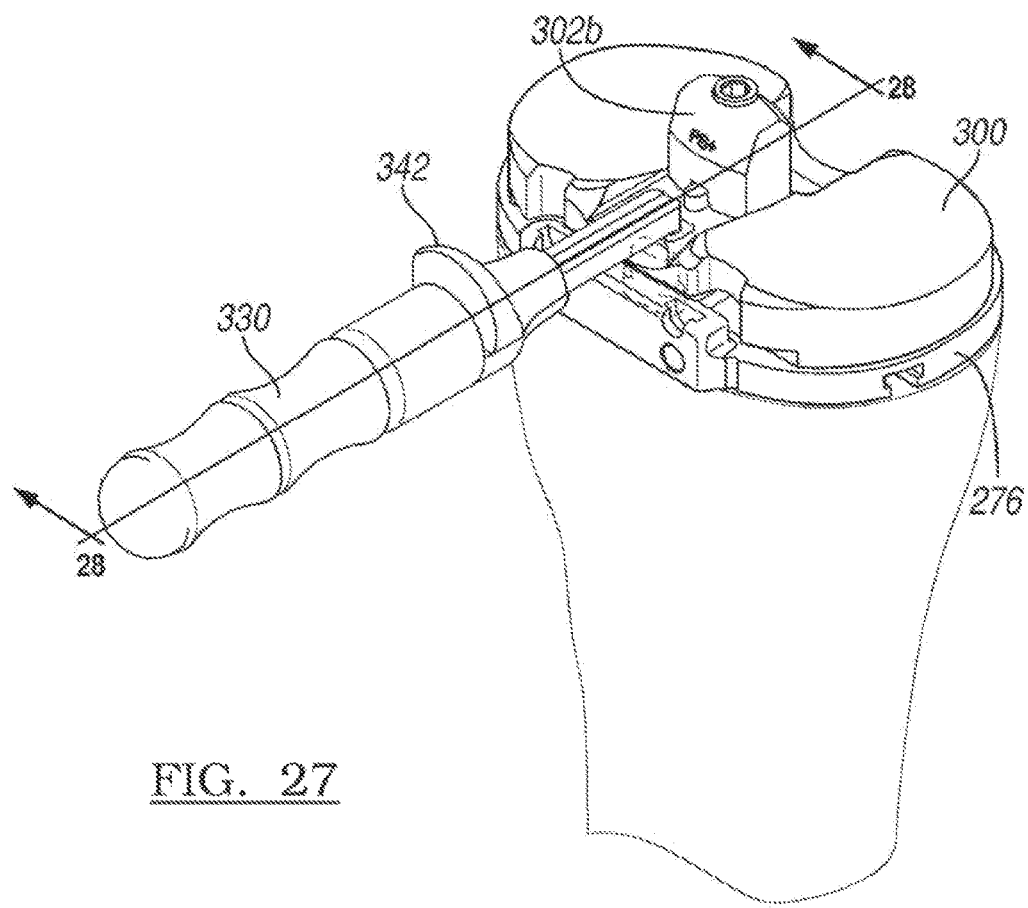
FIG. 27 is an anterior perspective view of the trial tibial tray and trial tibial bearing of FIG. 25 and illustrated with a bearing removal tool located into a passage of the trial tibial bearing during coupling and decoupling of the trial tibial bearing to the trial tibial tray.
Figure 28:
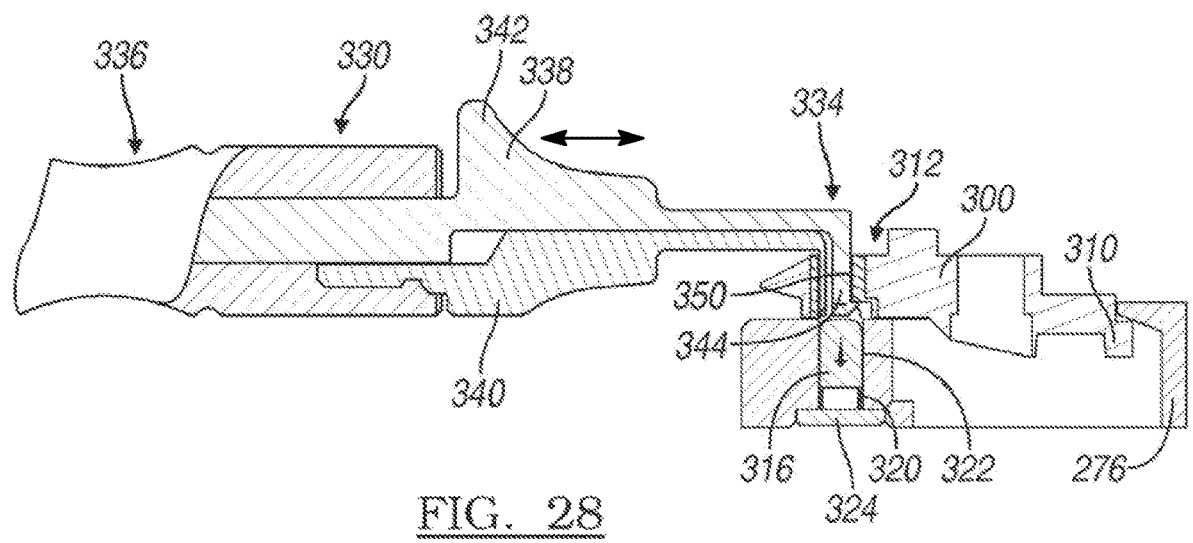
FIG. 28 is a cross-sectional view taken along lines 28-28 of FIG. 27 and shown with an actuator of the bearing removal tool being translated to displace an engagement tab to decouple the trial tibial bearing from the trial tibial tray.
Figure 45:
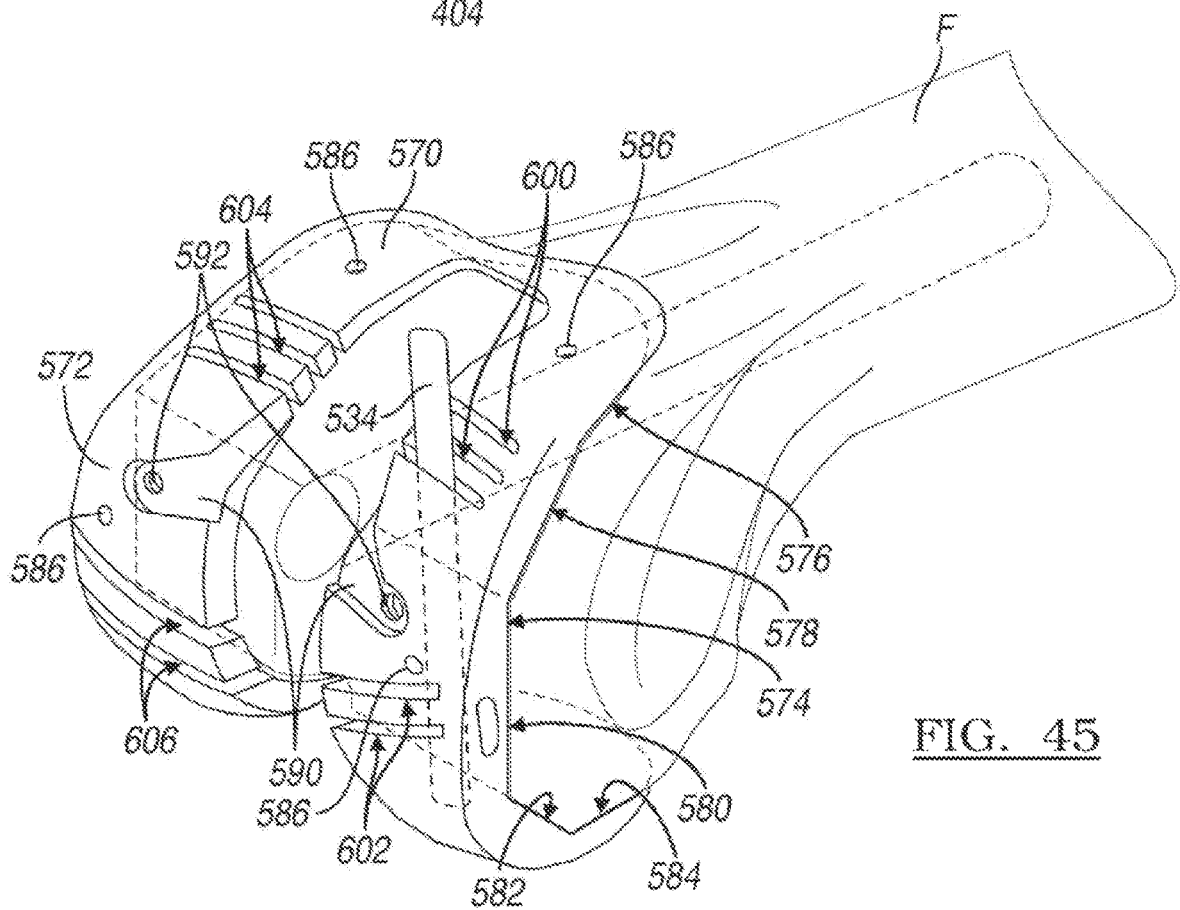
FIG. 45 is an anterior perspective view of a femoral cut-through trial positioned onto the prepared distal femur.

As illustrated in FIGS. 27 and 28, a bearing removal tool 330 can be provided for selectively removing the trial tibial bearing 300 from the trial tibial tray 276. In general, the bearing removal tool 330 can include a distal end 334 and a proximal end 336. An actuator 338 can be slidably mounted on a central body 340 of the bearing removal tool 330. The actuator 338 can have an engaging portion 342 formed thereon. The distal end 334 can generally comprise a distal tip 344 that can extend at an orthogonal angle relative to a longitudinal axis of the central body 340. The bearing removal tool 330 can be used to disconnect the trial tibial bearing 300 from the trial tibial tray 276. In this regard, the distal tip 344 of the bearing removal tool 330 can be initially advanced through a passage 350 (FIGS. 28 and 30) to depress the lock 316 into the bias of the spring 320. Once the lock 316 has been sufficiently depressed with the distal tip 344 (spring 320) of the bearing removal tool 330, a user can slidably advance the actuator 338 to provide a gripping force onto the trial tibial bearing 300 at the passage 350. The central body 340 can be fixed relative to the proximal end 336 while the tip 344 moves relative to the central body 340. Next, the user can lift the trial tibial bearing 300 away from the trial tibial tray 276 (see FIG. 29). At this point, the trial tibial tray and bearing combination having the optimal fit with the tibia can be noted for corresponding with the appropriate tibial implants. The trial tibial tray and bearing can then be trialed with the distal femur F or femoral cut-through-trial 570 (FIG. 45).

Figure 31:
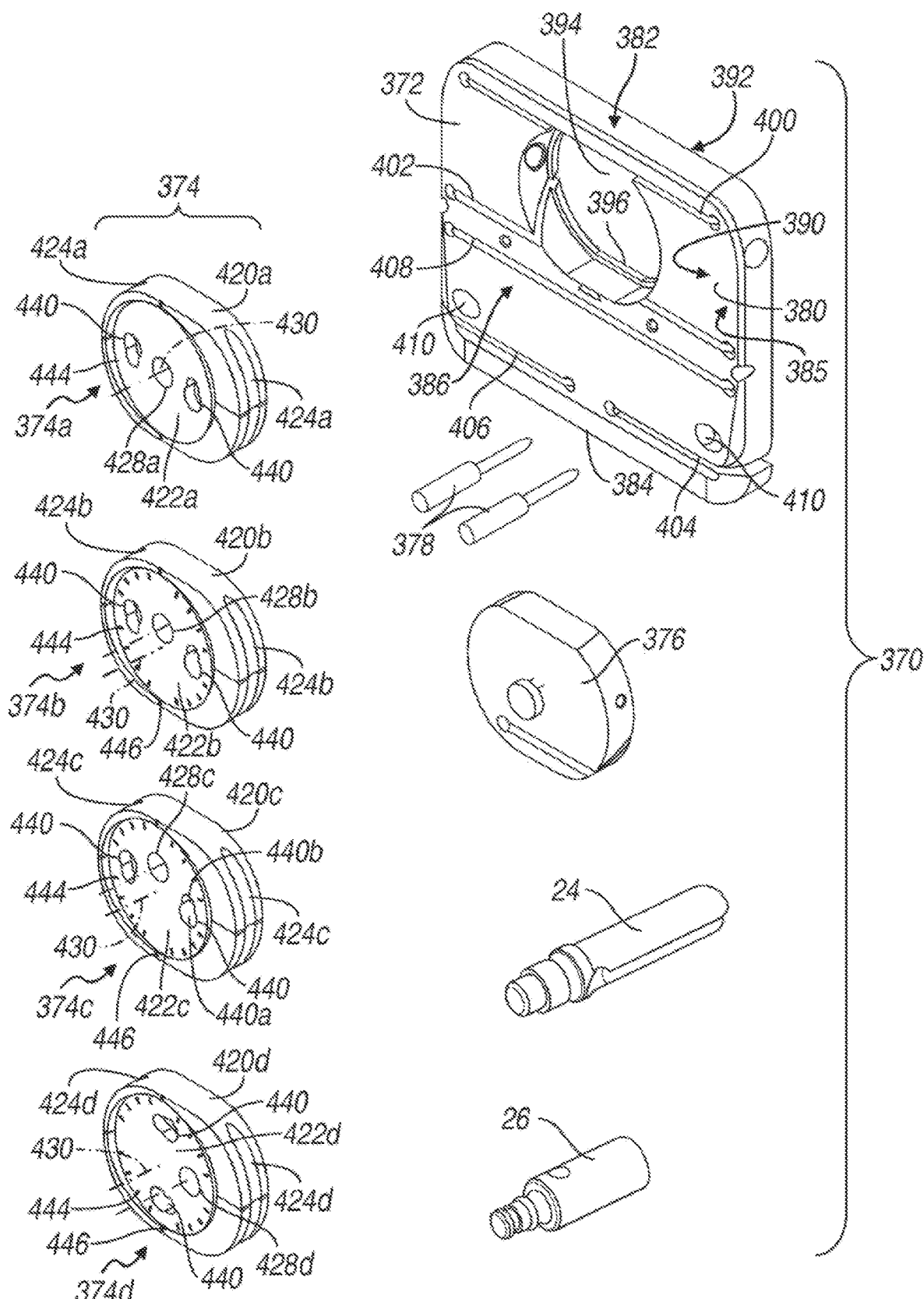
FIG. 31 is a perspective view of various instruments for preparing a distal femur according to the present teachings.

Turning now to FIG. 31, a system or kit of tools for femoral preparation are shown and generally identified at reference numeral 370. In general, the kit of tools 370 can comprise a femoral template 372, a series of femoral offset coin assemblies collectively referred to at reference numeral 374, a femoral cut block insert 376, pins 378, the locating stem 24 and the stem adapter 26. In general, femoral template 372 can be used to determine an optimal position of a femoral component relative to an IM canal of the femur. The femoral template 372 can also act as a cut block for guiding a cutting tool when preparing various cuts on a distal femur once the desired location on the distal femur has been determined. In this regard, the femoral template 372 can generally comprise a body 380 having an anterior portion 382, a posterior portion 384, a medial portion 385 and a lateral portion 386. In the particular example shown, the medial and lateral portions 385 and 386, respectively, are arbitrarily named as the femoral template 372 can be interchangeably used for either a right or a left knee. The body 380 can further include an inferior surface 390 and a superior surface 392. A locating bore 394 can be defined through the body 380 from the inferior surface 390 to the superior surface 392. In general, the locating bore 394 can define an oblong passage through the body 380. A shelf 396 can be formed on the superior surface 392 of the body 380 that generally projects into the locating bore 394. The body 380 can also define an anterior cut slot 400, an anterior chamfer cut slot 402, a first posterior cut slot 404, a second posterior cut slot 406 and a posterior chamfer cut slot 408. A pair of pin passages 410 can be defined through the body 380 generally through the posterior portion 384. As will become appreciated, the pin passages 410 can be configured to receive the pins 378 to fix the femoral template 372 relative to the distal femur once the desired position has been attained.

The femoral offset coin assemblies 374 are individually identified at reference numerals 374a, 374b, 374c and 374d.

Each femoral offset coin assembly 374a, 374b, 374c and 374d can comprise a femoral coin housing 420a, 420b, 420c and 420d and a corresponding positioning coin 422a, 422b, 422c and 422d. As will be described herein, the femoral offset coin assemblies 374 can be selectively and intraoperatively secured within the locating bore 394 of the femoral template 372 to determine a desired femoral offset. More specifically, the stem adapter 26 and locating stem 24 can be selectively coupled relative to each of the positioning coins 422a, 422b, 422c and 422d while the associated femoral coin housing 420a, 420b, 420c or 420d is positioned into the locating bore 374 of the femoral template 372.

The femoral coin housings 420a, 420b, 420c and 420d can each respectively include a locating groove 424a, 424b, 424c and 424d thereon. The positioning coins 422a, 422b, 422c and 422d each have respective bores 428a, 428b, 428c and 428d formed therein. The location of the respective bores 428a, 428b, 428c and 428d can correspond to various offsets. Each of the bores 428a, 428b, 428c and 428d are offset a distance relative to a longitudinal axis or center, collectively identified at reference numeral 430, of the respective positioning coins. In this regard, the femoral offset coin assemblies 374 can include a zero offset (positioning coin 422a), a 2.5 mm offset (positioning coin 422b), a 5 mm offset (positioning coin 422c) and a 7.5 mm offset (positioning coin 422d).

Figure 43:
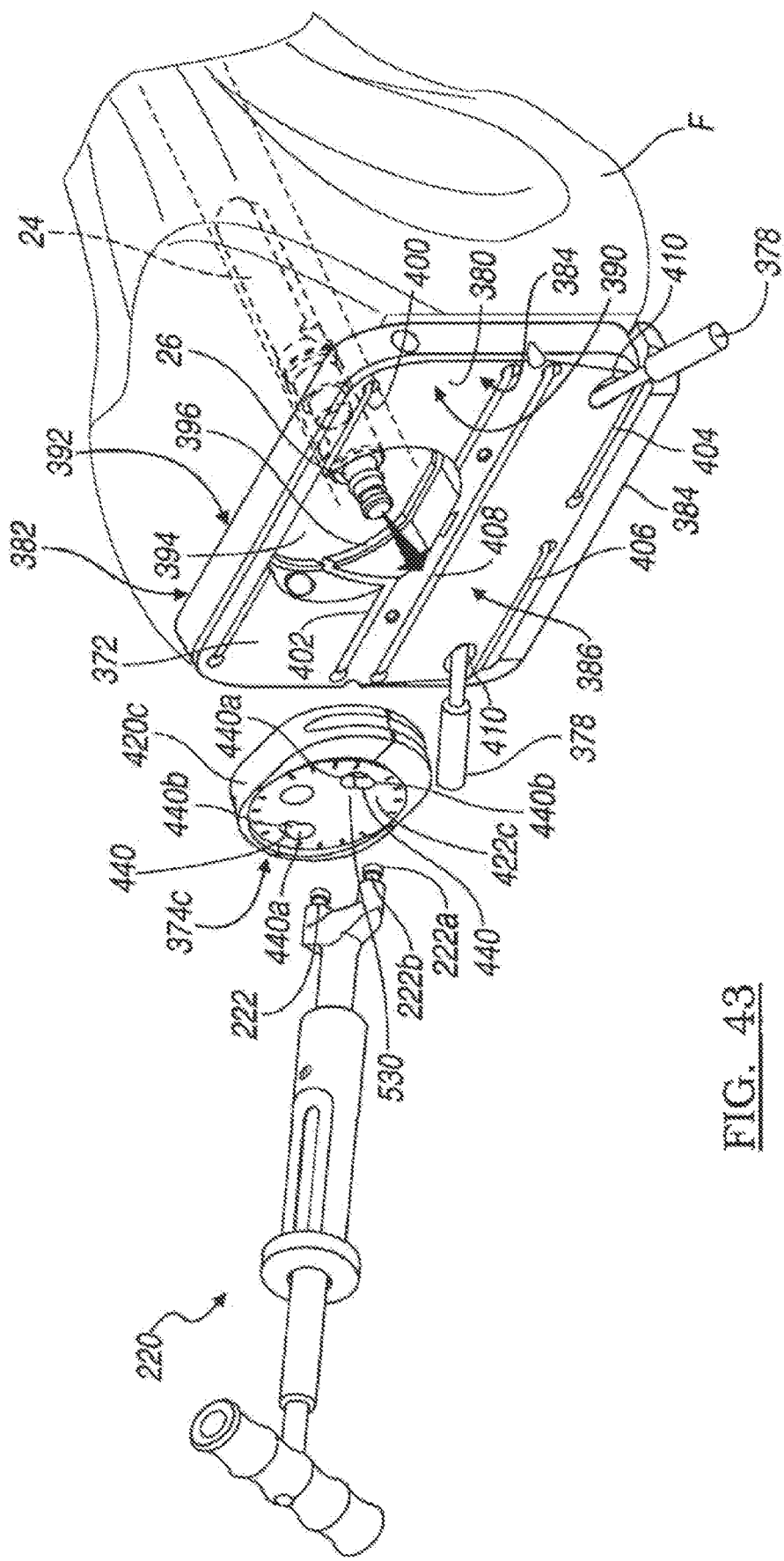
FIG. 43 is an anterior perspective view of the femoral cut block shown with the removal tool removing the offset coin assembly, stem adapter and locating stem subsequent to pinning the femoral cut block at the desired location.

Each of the positioning coins 422a, 422b, 422c and 422d can include a pair of locating apertures 440. The locating apertures 440 can each have a first diameter portion 440a and a second diameter portion 440b. The second diameter portion 440b can have a diameter that is less than the first diameter portion 440a for interfacing with the removal tool 220 (FIG. 43). Each of the positioning coins 422b, 422c and 422d can have an indicia 444 formed thereon. As will be described, the indicia 444 can be referenced relative to a notch collectively identified at reference numeral 446 on the respective femoral coin housings 420b, 420c and 420d.

Figure 32:
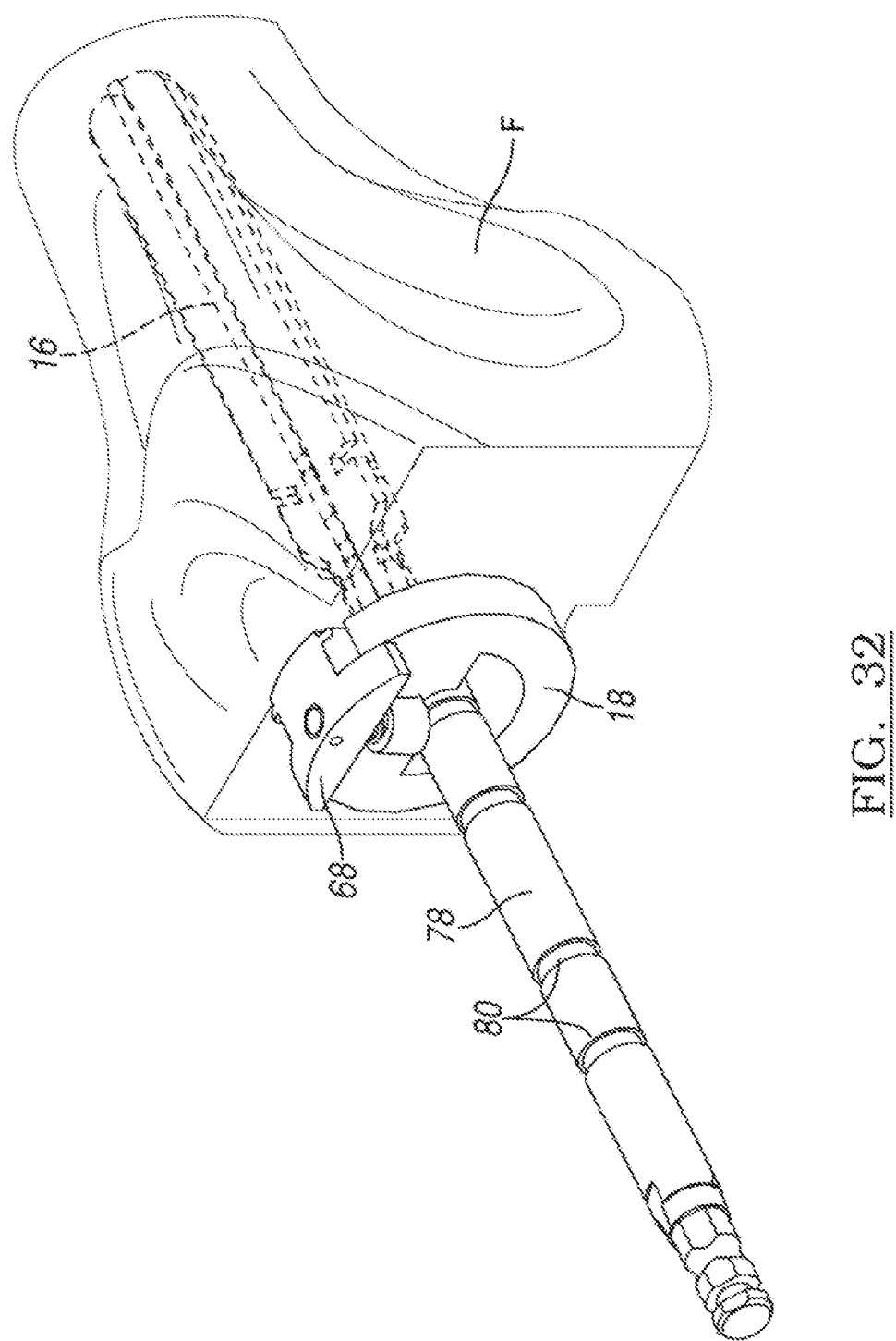
FIG. 32 is an anterior perspective view of a reamer stop positioned on a resected distal femur and shown with a reamer shaft extending into an IM canal of the femur.

With reference now to FIG. 32, an exemplary method for preparing a femur F during revision surgery will be described. Again, it can be appreciated that in a revision surgery, it may be necessary to remove a prior implanted femoral component in any suitable manner. At the outset, the IM reamer stop 18 can be coupled to the reamer shaft 78 at the desired location. The reamer 16 can cooperate with the IM reamer stop 18 to prepare the IM canal of the femur F in a similar manner as described above with respect to preparation of the IM canal of the tibia (see FIGS. 4-6). The reamer shaft 78 can be driven by a drive device (not specifically shown) at a drive end. Also, as discussed above, the grooves 80 can correspond to various depths of reaming into the femur F. As can be appreciated, the various depths of reaming can correspond to various lengths of femoral stems (such as femoral stem 450, FIG. 54).

Figure 54:
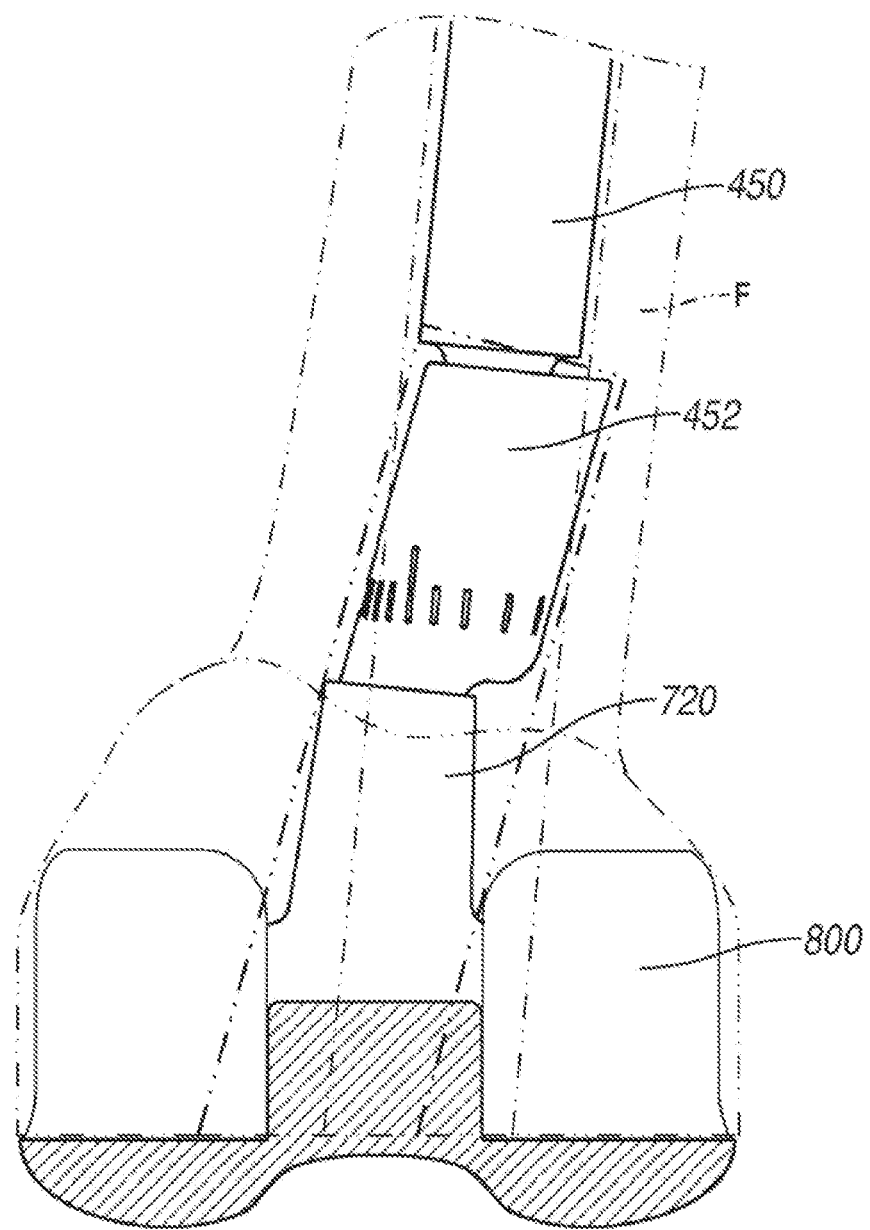
FIG. 54 is an anterior view of the distal femur shown with an exemplary femoral component, offset adapter and femoral stem implanted into the prepared distal femur.

As with the tibia described above, in some examples, it may be necessary to implant an offset adapter (such as offset adapter 452, FIG. 54). In those examples where an offset adapter is needed in conjunction with a stem, the grooves 80 will correspond to different lengths of stems. For example, if a 40 mm offset adapter will be used, the groove that corresponds to an 80 mm femoral stem (used alone) will also correspond to a 40 mm femoral stem that will be used in conjunction with a 40 mm femoral offset adapter. Again, the grooves 80 can be provided in any combination of configurations along the reamer shaft 78 for identifying a depth of reaming that can accommodate any combination of stems and/or offset adapters as needed. Furthermore, various reamers having distinct diameters can be used until adequate cortical contact is achieved in the femur F. Moreover, multiple IM reamer stops 18 can be provided, each being operatively connected to a reamer 16 having a distinct diameter.

Figure 33:
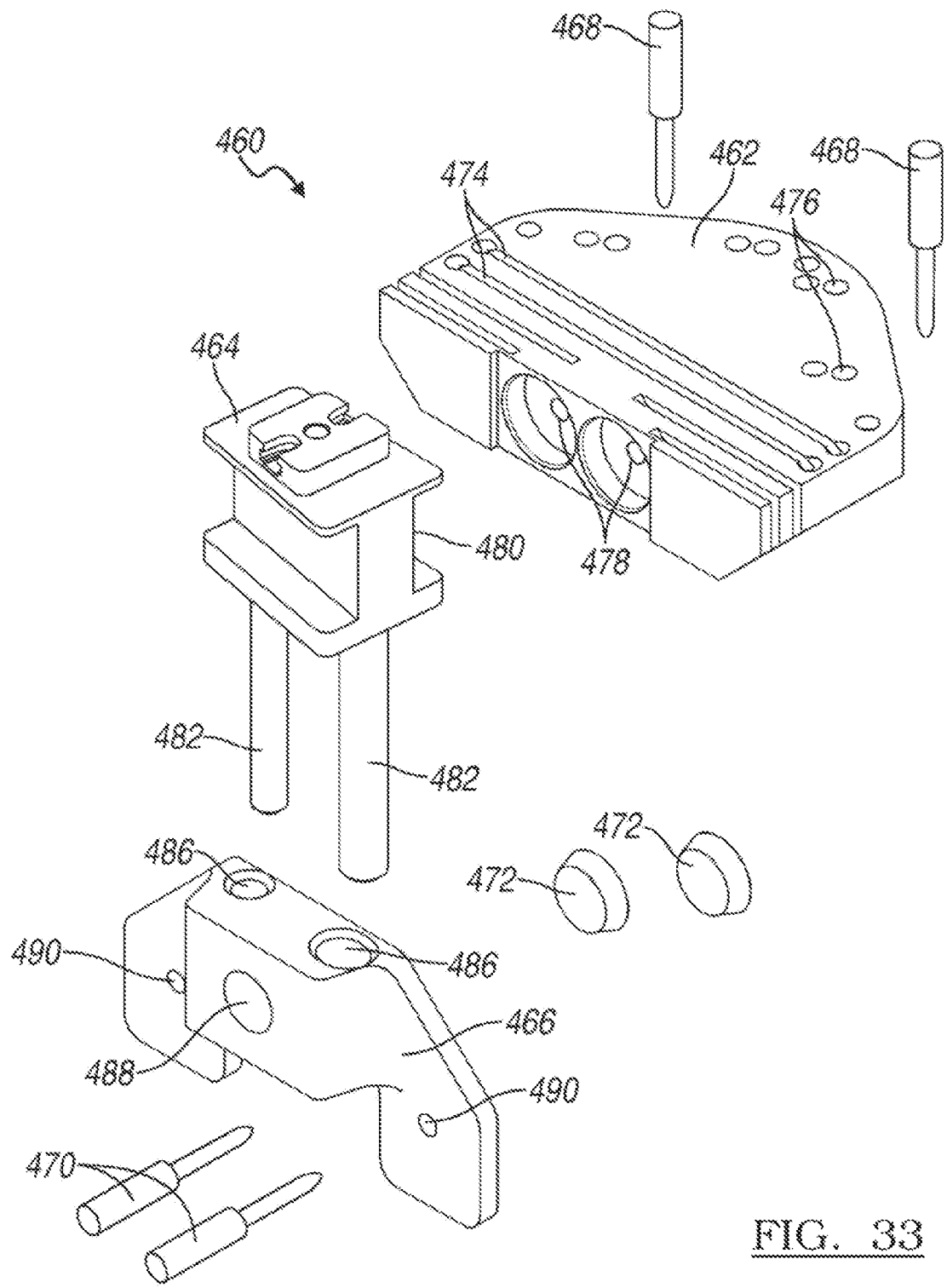
FIG. 33 is a perspective view of a femoral cut guide positioning assembly according to the present teachings.

With reference now to FIG. 33, a distal revision cut assembly 460 will be described. The distal revision cut assembly 460 can generally comprise a distal revision block 462, a tower 464, a distal positioning plate 466, a first pair of pins 468, a second pair of pins 470 and magnets 472. The distal revision block 462 can generally include a series of cut slots 474, a plurality of pin passages 476 and a pair of recesses 478 for receiving the magnets 472. The tower 464 can generally include a locating channel 480 and a pair of posts 482. The distal positioning plate 466 can generally include a pair of bores 486 for selectively receiving the posts 482 of the tower 464. The distal positioning plate 466 can further define a throughbore 488 for operatively receiving the reamer shaft 78, as will be described. A pair of passages 490 can be defined in the distal positioning plate 466 for intraoperatively receiving the pins 470.

With specific reference now to FIG. 34, the distal revision cut assembly 460 will be described according to one exemplary method of use. Initially, the throughbore 488 of the distal positioning plate 466 can be advanced over the reamer shaft 78 until reaching a position against the distal femur. Next, the distal revision block 462 can be coupled to the tower 464. In one example, the channel 480 of the tower 464 can locate along the distal revision block 462, such that the magnets 472 magnetically connect the tower 464 along the distal revision block 462. At this point, the posts 482 can locate through the bores 486 in the distal positioning plate 466. It can be appreciated that the sequence of assembly described with respect to FIG. 34 for the distal revision cut assembly 460 can be altered while still reaching the same result. Once the desired location has been attained, the distal positioning plate 466 can be pinned to the distal femur using the second set of pins 470. Next, the first set of pins 468 can be located through the passages 476 in a distal revision block 462 to pin the distal revision block 462 to the distal femur. At this point, the reamer 16, distal positioning plate 466 and tower 464 can be removed leaving only the distal revision block 462 (see FIG. 35). Next, distal cuts can be made on the femur F using any of the cut slots 474 defined through the distal revision block 462 in order to make a distal resection or prepare for distal augments, if necessary (see FIG. 36A).

Figure 36A:
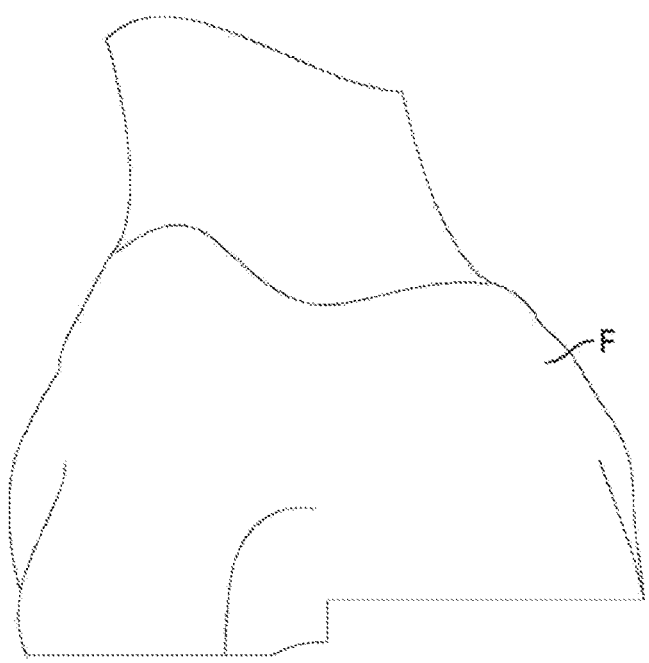
FIG. 36A is an anterior view of the femur of FIG. 35 and shown subsequent to a vertical cut being made for receipt of a medial augment.
Figure 36B:
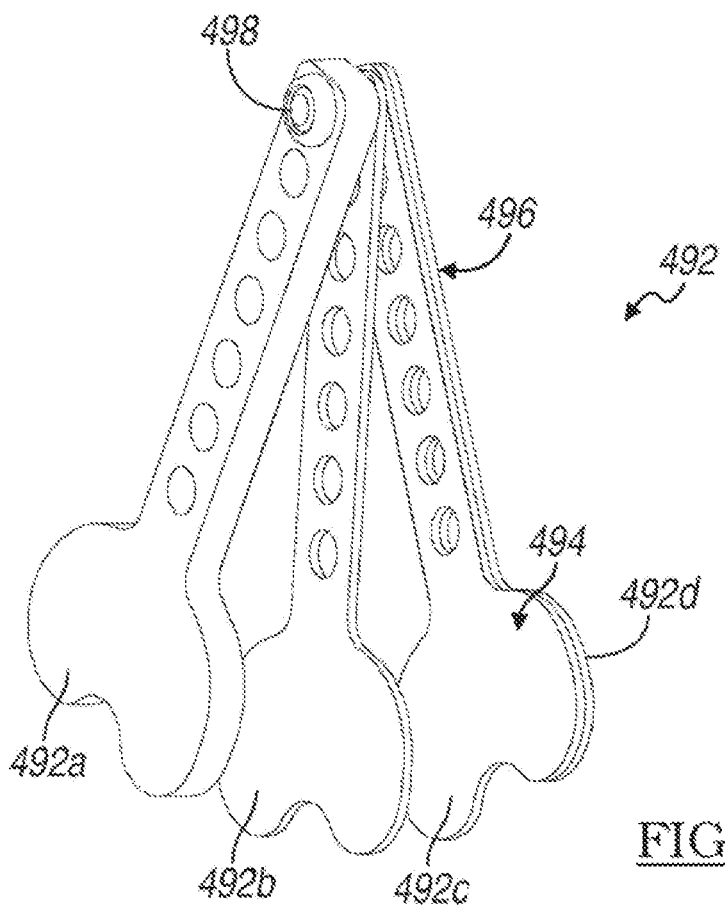
FIG. 36B is a perspective view of a set of femoral spacers according to the present teachings.
Figure 36C:
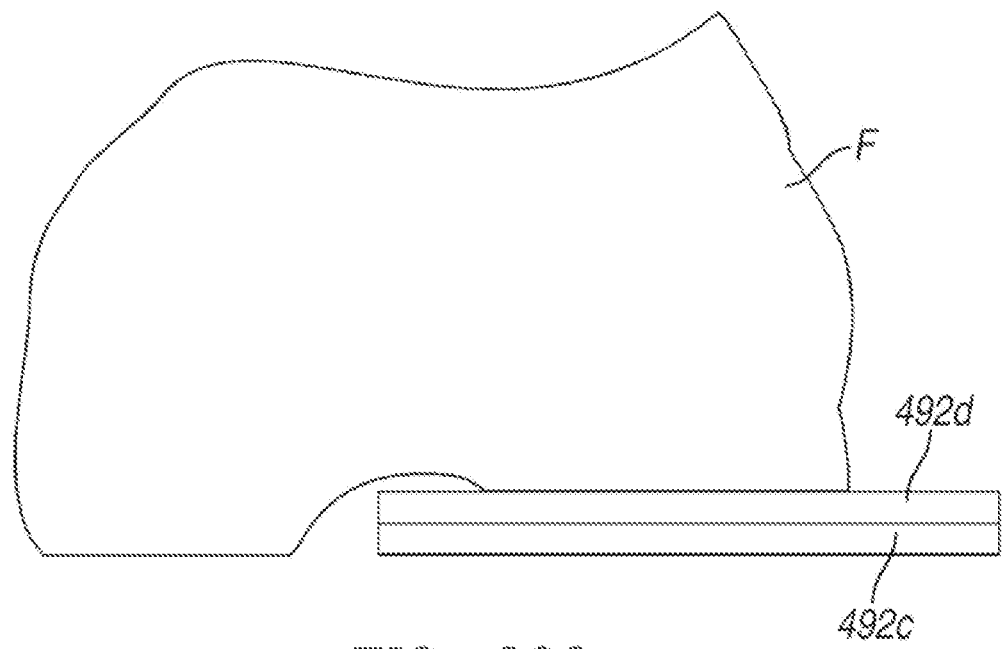
FIG. 36C is an anterior view of the femur of FIG. 36A showing two of the femoral spacers used to determine an augment thickness.

FIG. 36B illustrates exemplary femoral spacers 492. In the depicted example, femoral spacers 492a, 492b, 492c and 492d are provided. The femoral spacer 492a has a thickness of 10 mm. The remaining femoral spacers 492b-492d each have a thickness of 5 mm. The femoral spacer assembly 492 can be stacked, as needed, to achieve a desired height. The thickness of a given stack of femoral spacers represents a desired thickness of a femoral prosthetic component. For example, as shown on FIG. 36C, the femoral spacers 492c and 492d are stacked on a distal femur F to determine a thickness of a medial femoral augment. The spacers 492 can also be used to determine a thickness of a lateral femoral augment.

The respective spacers 492a-492d can each include a distal femoral portion, collectively referred to by reference numeral 494, and a handle portion, collectively referred to by reference numeral 496. Each of the femoral spacers 492a-492d can be rotatably connected at terminal ends by way of a fastener 498. The respective femoral spacers 492a-492d can each pivotally rotate about a fastener 498 in order to isolate a desired femoral spacer 492a-492d from the remainder of spacers 492a-492d. Furthermore, the spacers 492 can be used to determine a joint line of the femur F using anatomical landmarks. Specifically, the distal femoral portion 494 of a given femoral spacer 492a-492d can be placed against the distal femur F. In one example, the primary femur can be removed and the selected spacers 492a-492d can be positioned on the previously resected femur F. The spacers 492a-492d can be universal and can accommodate a left of a right femur. The appropriate joint line can be confirmed when the proper thickness spacer 492a-492d is placed on the distal femur and presents a desired height (i.e. inferiorly from the distal femur) relative to anatomical landmarks.

Figure 36D:
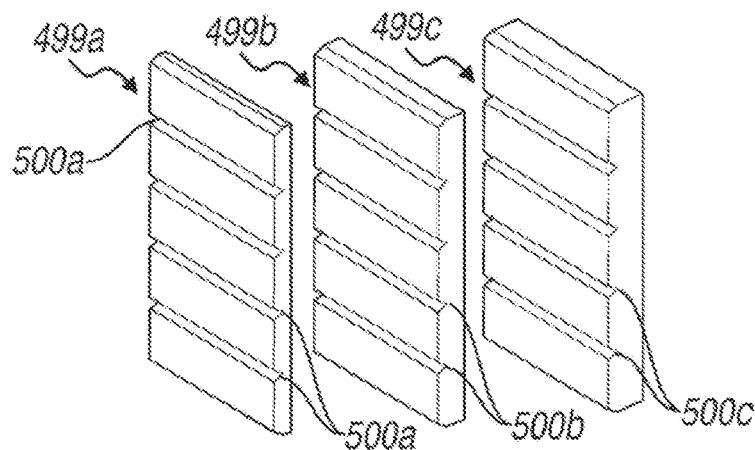
FIG. 36D is a perspective view of a series of resorbable augment trial spacers according to additional features.

With reference to FIG. 36D, a series of augment trial spacers 499a, 499b and 499c are illustrated. In the example shown, the augment trial spacer 499a can have a thickness of 5 mm, the augment trial spacer 499b can have a thickness of 10 mm and the augment trial spacer 499c can have a thickness of 15 mm. The thickness is identified as a dimension in the superior/inferior direction as these augment trial spacers 499a, 499b and 499c can be configured to be located at a location on the distal femur to fill the space of a removed femoral defect (i.e., such as shown in FIG. 36A). The augment trial spacers are made of bioresorbable material, such as Lactosorb®. Because the augment trial spacers 499a, 499b and 499c are formed of bioresorbable material, if needed, a surgeon can simply cut or pierce through the augment trial spacers 499a, 499b or 499c while preparing the bone. It can be appreciated that the augment trial spacers 499a, 499b and 499c can be used in areas that are not only possible for engaging a saw blade but also any of the pins, reamers or other cutting devices discussed herein. In this regard, a surgeon can make cuts, place pins and prepare the bone without worry for dulling the tools or creating debris, which the body cannot easily handle. For example, if a saw blade or pin, such as any disclosed herein, passes through the augment trial spacer and carries some particles or small pieces of the augment trial spacer into the bone, the particles or small pieces will simply be absorbed into the body without causing infection.

Figure 38:
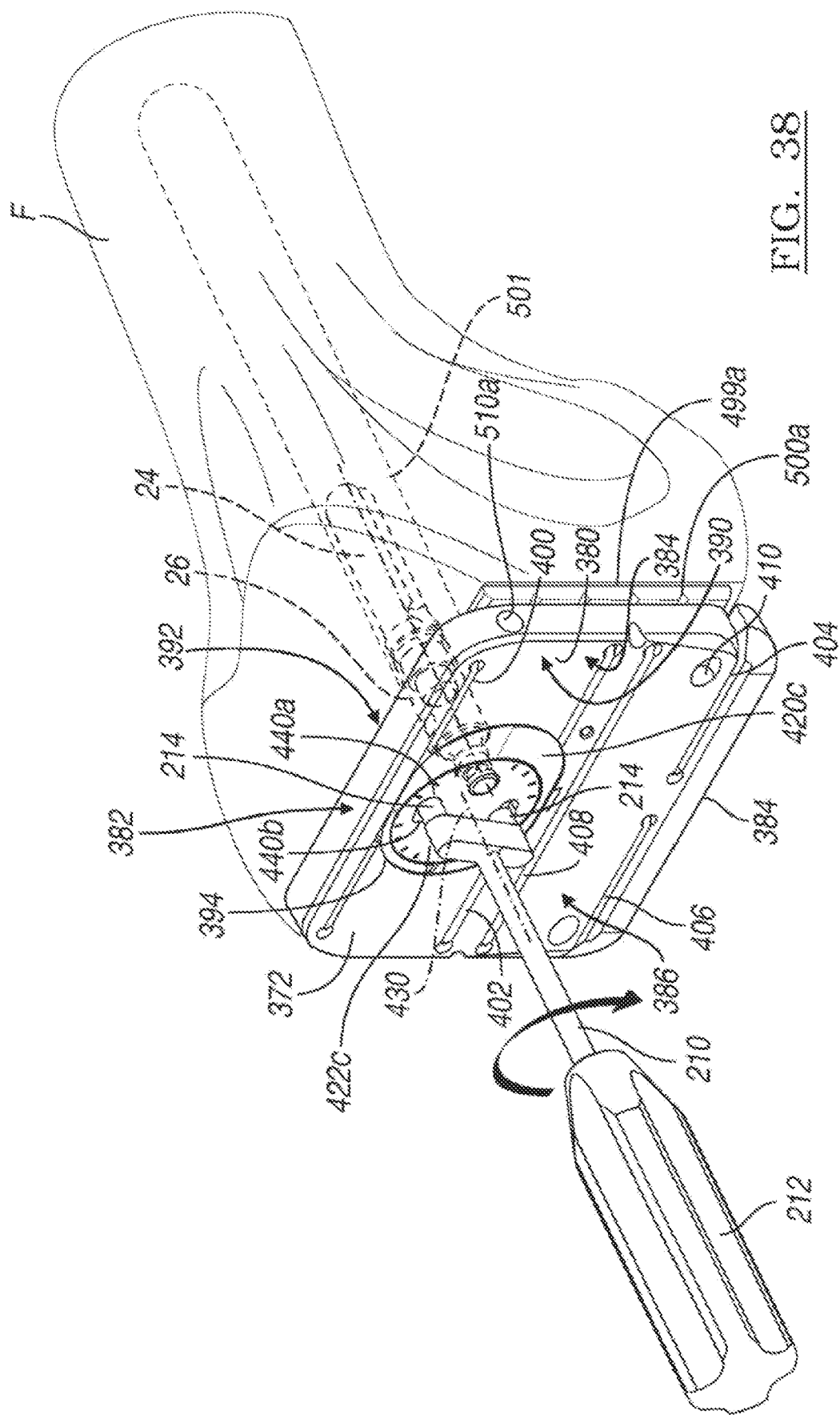
FIG. 38 is an anterior perspective view of the femoral cut block shown with the positioning tool rotating an offset coin of the femoral offset coin assembly while the locating stem and stem adapter are positioned in the IM canal of the femur.
Figure 39:
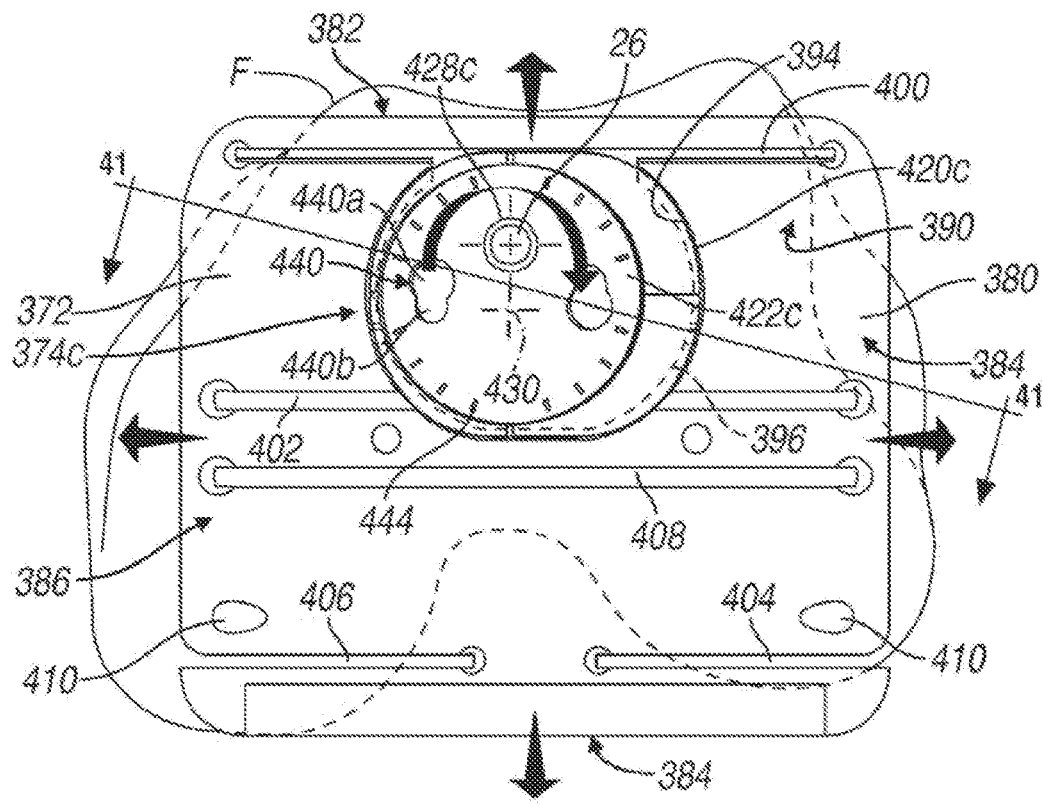
FIG. 39 is an inferior view of the femoral cut block positioned on the distal femur while the offset coin is rotated until the femoral cut block slidably locates along the distal femur until a desired location is attained.
Figure 40:
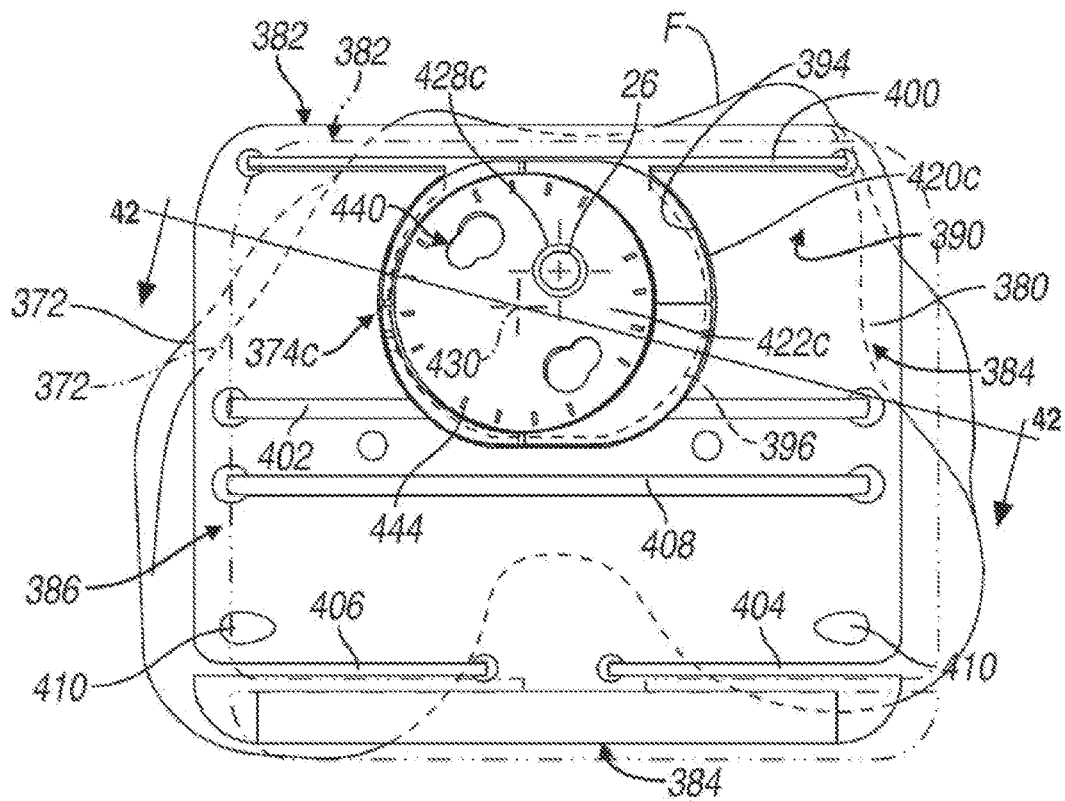
FIG. 40 is an inferior view of the femoral cut block and offset coin assembly of FIG. 39 and shown with the femoral cut block positioned in the desired location.
Figure 41:
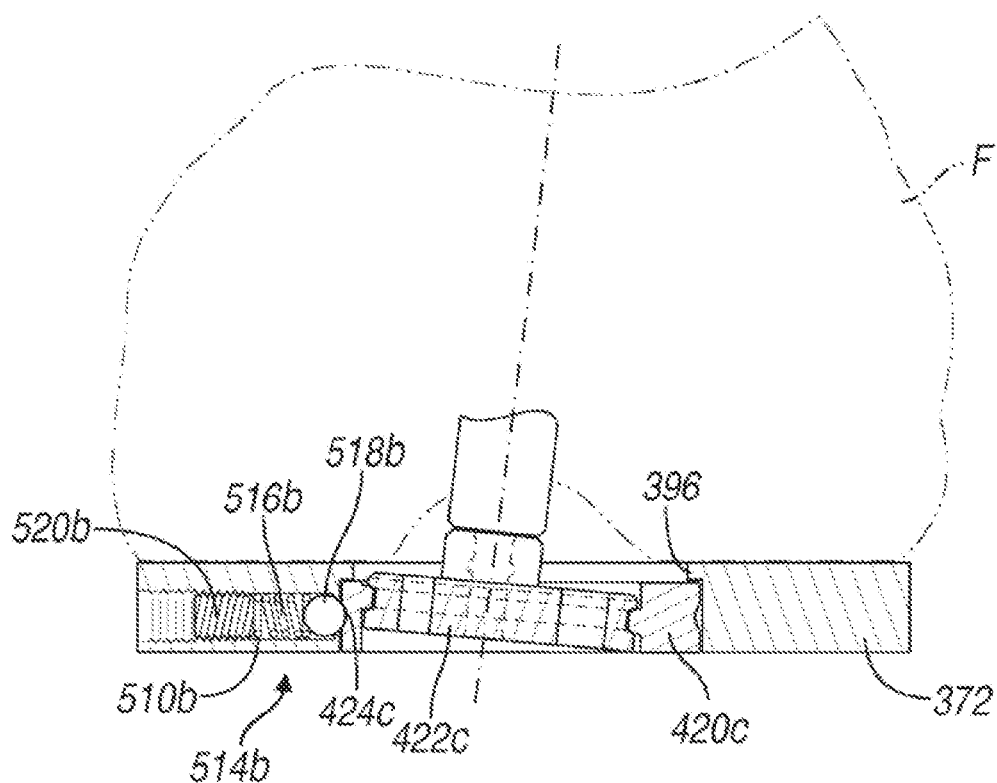
FIG. 41 is a cross-sectional view of the femoral cut block and offset coin assembly taken along lines 41-41 of FIG. 39.
Figure 42:
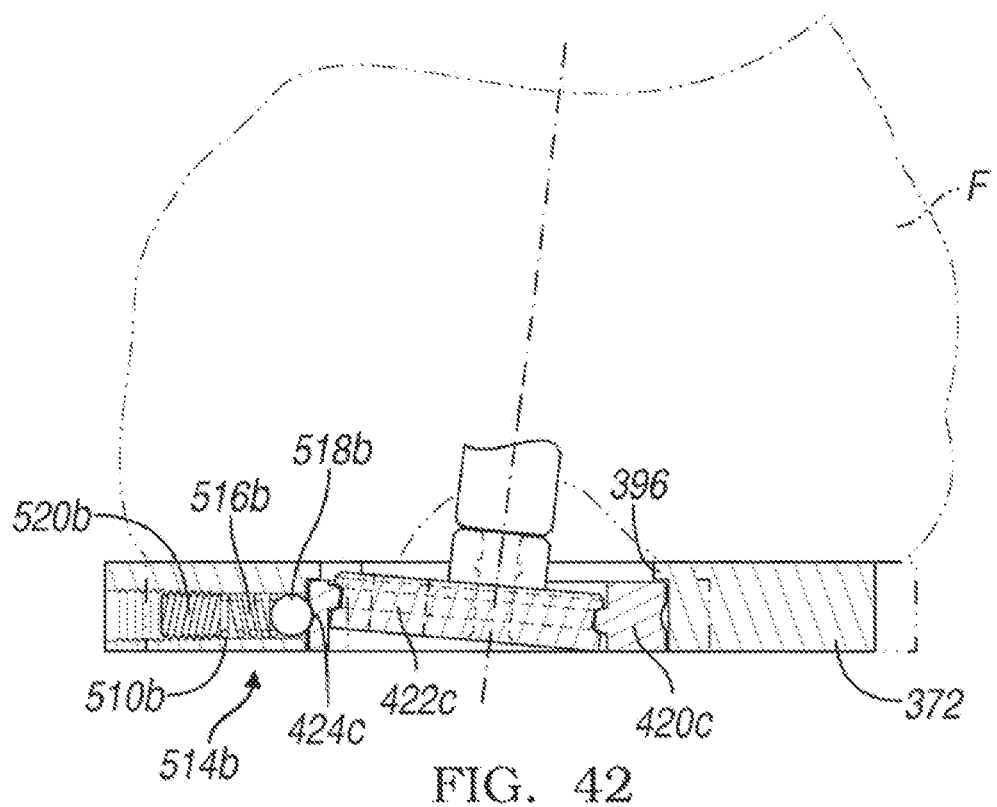
FIG. 42 is a cross-sectional view of the femoral cut block and offset coin assembly taken along lines 42-42 of FIG. 40.

In some examples, some or all of the outside surfaces of the augment trial spacers 499a, 499b and 499c can have a tacky or sticky surface that can facilitate gripping of the bone or adjacent instrument. The augment trial spacers 499a, 499b and 499c can additionally include score marks 500a, 500b and 500c, respectively. The score marks can assist the surgeon in snapping or cutting off unneeded depth (in the anterior/posterior direction) of the augment trial spacers 499a, 499b and 499c. As shown in FIG. 38, the augment trial spacer 499a is shown positioned between the distal femur and femoral template 372. It can be appreciated that the augment trial spacers 499a, 499b and 499c can additionally or alternatively be used during preparation of the proximal tibia.

Figure 37:
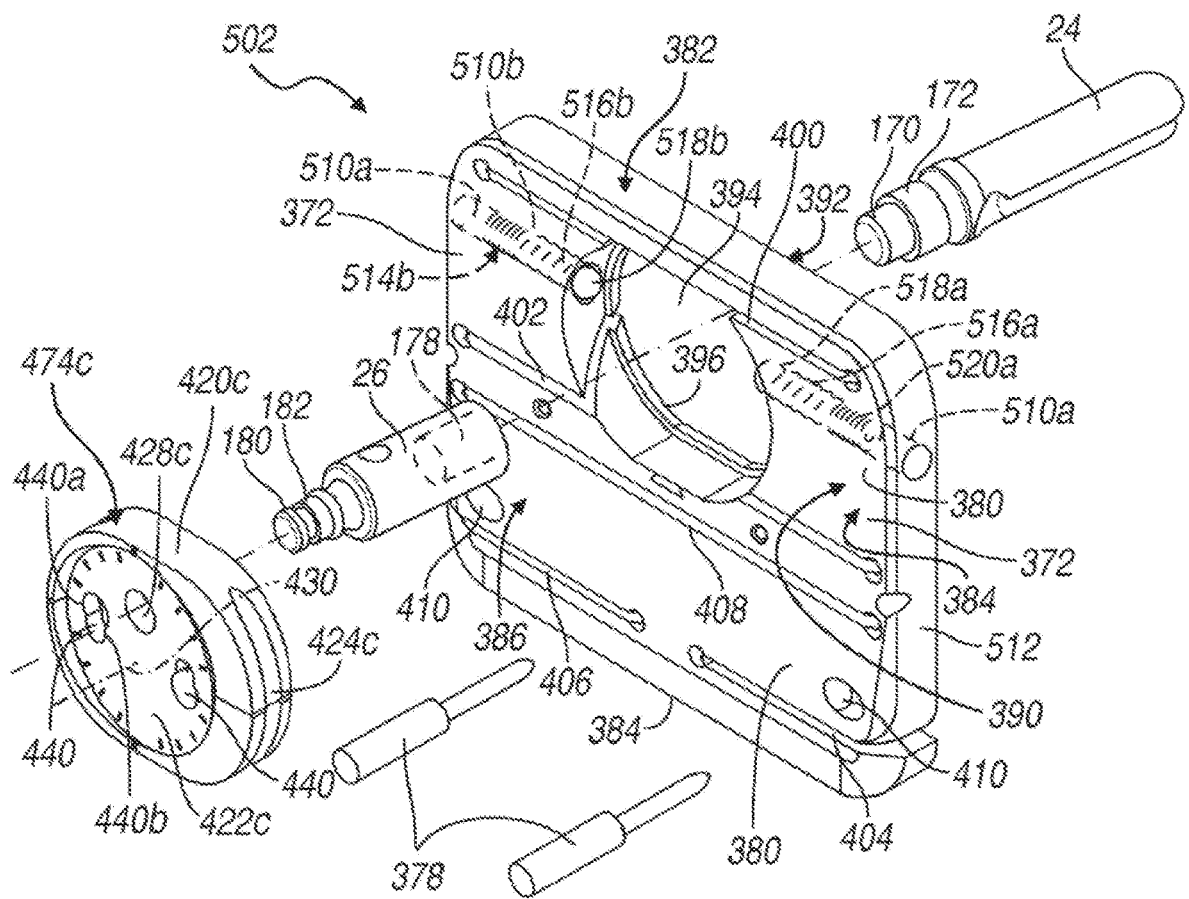
FIG. 37 is a perspective view of a femoral cut block shown with a femoral offset coin assembly, stem adapter and locating stem according to the present teachings.

With reference now to FIGS. 31 and 37-42, the offset position of a prepared IM canal 501 of the femur F will be determined using a femoral offset positioning assembly 502 (FIG. 37). The femoral offset positioning assembly 502 can generally comprise the femoral template 372, the femoral offset coin assemblies 374 (FIG. 31), the locating stem 24, the stem adapter 26 and the pair of pins 378. Prior to describing an exemplary method for using the femoral offset positioning assembly 502, additional features of the femoral template 372 will be described with reference to FIGS. 37, 41 and 42. The body 380 of the femoral template 372 can have a pair of bores 510a and 510b, respectively formed therein. According to one example, the bores 510a and 510b can be formed from an exterior surface 512 of the body 380 to the locating bore 394. Both of the bores 510a and 510b can have a spring biased ball assembly 514a and 514b, respectively therein. Both of the spring biased ball assemblies 514a and 514b can include biasing members 516a and 516b that bias balls 518a and 518b, respectively in a direction toward the locating bore 394 for selectively engaging the locating grooves (424a, 424b, 424c and 424d) of the respectively femoral coin housings 420a, 420b, 420c and 420d as will be described. According to one example, both of the bores 510a and 510b can include stops or set screws 520a and 520b therein that capture the respective biasing members 516a and 516b. According to some examples, the bores 510a and 510b can be stepped, such that the respective stops 520a and 520b can be advanced to a location where the stepped bores transition to a reduced diameter. It can be further appreciated that the bores 510a and 510b can have a diameter that is less than the balls 518a and 518b near the locating bore 394 to capture the respective balls 518a and 518b in the body 380 of the femoral template 372.

As described above, the locating stem 24 can be selectively coupled to the stem adapter 26. In this regard, the hub 170 of the locating stem 24 can be configured to locate into the blind bore 178 of the stem adapter 26. Similarly, the projection portion 180 of the stem adapter 26 can be configured to be received by a bore (such as the bore 428c) of a positioning coin, such as the positioning coin 422c. In this regard, the surgeon can select one of the femoral offset coin assemblies 374 that would appear to have a suitable offset for cooperating with the prepared IM canal 501 (FIG. 38). In the examples shown in FIGS. 37-43, the surgeon has selected the femoral offset coin assembly 474c having the positioning coin 422c that includes the 5 mm offset. It can be appreciated however that the surgeon may need to intraoperatively switch between the femoral offset coin assemblies 374 until the appropriate offset (recognizing that zero offset may be used with the femoral offset coin assembly 374a) has been selected. While not specifically shown, in some examples an annular projection (such as the annular projection 184 identified in FIG. 15 of the positioning coin 22c) can create an interference fit with the groove 182 in the stem adapter 26. Again, an o-ring or other supplemental engaging member may also be positioned between the projection portion 180 and the bore 428c. The femoral offset coin assembly 474c can then be advanced into the locating bore 394 of the femoral template 372 until the respective balls 518a and 518b locate into the groove 424c of the femoral coin housing 420c of the femoral offset coin assembly 374c. As can be appreciated, the respective balls 518a and 518b can initially translate against the bias of the springs 516a and 516b, respectively, until the groove 424c aligns for receipt of the respective balls 518a and 518b (see FIGS. 41 and 42). It can also be appreciated that concurrently, the femoral coin housing 420c can rest atop the shelf 396 provided on the body 380 at the locating bore 394.

At this point, it is important to recognize that only the locating stem 24 is fixed (or substantially fixed) relative to the femur F. The positioning coin 422c is able to rotate around its longitudinal center axis 430 within the femoral coin housing 420c, causing the femoral template 372 to move around the distal femur (see FIGS. 38-40). The positioning coin 422c can be rotated (e.g., by the surgeon) around its longitudinal axis 430 with the positioning tool 210. Similarly, as described above with respect to the tibial offset positioning assembly 122 described above, the fork members 214 can be inserted into the first diameter portions 440a of the respective locating apertures 440 of the positioning coin 422c. The positioning coin 422c can be rotated around the axis 430 until a position (degree and/or offset) is attained in which the body 380 achieves optimal coverage or placed over cortical bone of the distal femur F. Again, in some instances, the surgeon may need to swap out various femoral offset coin assemblies 374 in order to attain the best possible coverage of the distal femur.

The femoral template 372 can also be used to verify joint space of the knee prior to making the distal cuts. In one example, the femoral template 372 can have a thickness of 9 mm. The femoral template 372 can be positioned on the distal femur while the tibial template 20 is positioned on the proximal tibia. The joint space can be observed with the knee in flexion to determine the optimal position of the femoral template 372. The tibial spacers 50 (FIGS. 2 and 3) may also be used to account for additional space. Additionally, the femoral spacers 492 may be used. In some examples, the tibial and/or femoral spacers 50, 492 can be placed directly against the respective bones (i.e., without either of the tibial template 20 or femoral template 372). Because the system of the present teachings allows the surgeon to adjust the offset position of the femoral template 372, a surgeon can open and close the flexion space by moving the femoral template 372 around the distal femur using the tibial and/or femoral spacers as needed and observing the flexion space in real time.

Once the desired position on the distal femur is verified, the femoral template 372 can be fixed relative to the femur F, such as by the pins 378 (FIG. 43). At this point, the surgeon can make a note of the indicia 444 relative to the mark or notch 446 on the femoral coin housing 420*c*. This will correspond to the femoral offset position. Again, in some instances, it can be appreciated that no offset may be necessary (i.e., optimal coverage can be confirmed with the femoral offset coin assembly 374*a*).

Turning now to FIG. 43, once the femoral template 372 has been secured to the distal femur F with the pins 378, the femoral offset coin assembly 374*c* can be removed from the stem adapter 26, such as with the removal tool 220. Similarly, with the tibial offset positioning assembly 122 described above, the first diameter portion 222*a* of the fork portion 222 can be advanced into the first diameter portion 440*a* of the apertures 440. The removal tool 220 can then rotated around its longitudinal axis, such that the second diameter portions 222*b* of the fork portions 222 locate into the second diameter portions 440*b* of the apertures 440. In this position, the first diameter portions 222*a* of the fork portions 222 can locate under an edge of the second diameter portions 440*b* a ledge 530 of the positioning coin 422*c* to transfer a pulling force onto the positioning coin 422*c*. The stem adapter 26 and the locating stem 24 can also be removed at this point.

Figure 44:
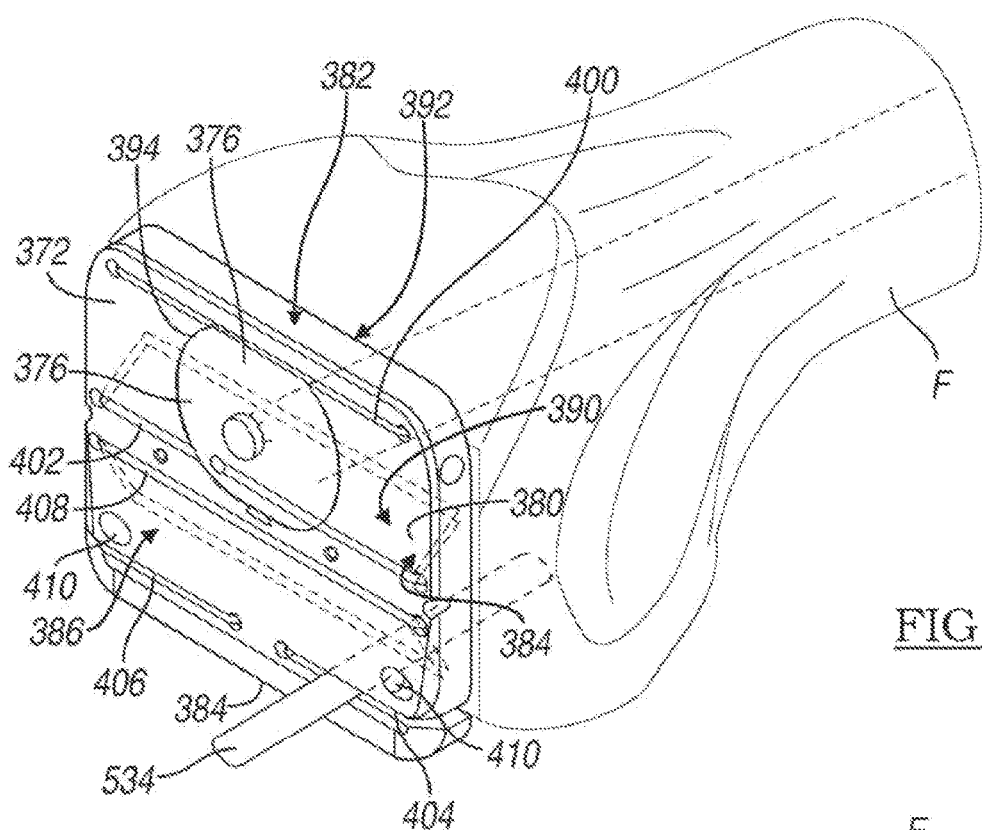
FIG. 44 is an anterior perspective view of the femoral cut block shown with a femoral cut block insert located into the locating bore of the femoral cut block and with a saw preparing the distal cuts in the femur.

Turning now to FIG. 44, once the femoral template 372 has been securely pinned to the distal femur and the femoral offset coin assembly 374*c* is removed from the locating bore 394, the femoral cut block insert 376 can be inserted into the locating bore 394. At this point, the surgeon can make the respective cuts on the distal femur using a cutting instrument 534. More specifically, the surgeon can use the anterior cut slot 400, the anterior chamfer cut slot 402, the first posterior cut slot 404, the second posterior cut slot 406 and the posterior chamfer cut slot 408 as guides for the cutting instrument 534. In this regard, the femoral template 372 can be utilized to not only assist in determining an optimal femoral offset to achieve a desired coverage on a distal femur, but also be used as a cutting block to guide the cutting instrument 534 when making the distal cuts on the femur F. Furthermore, the femoral template 372 can be used as a spacer when verifying a joint line. In one example, the femoral template 372 can have a thickness of 10 mm.

Once the anterior cut, posterior cut and anterior and posterior chamfer cuts have been made on the distal femur, the femoral template 372 and femoral cut block insert 376 can be removed from the distal femur. At this point, a femoral cut-through-trial 570 can be positioned on the prepared distal femur F (FIG. 45). The femoral cut-through-trial 570 can be used for both femoral trialing and as a guide for cutting portions of the femur F for receipt of femoral augments as will be described. According to one advantage of the present teachings, the femoral cut-through-trial 570 can remain fixed to the distal femur F once the desired coverage and offset (if necessary) has been determined. The femoral cut-through-trial 570 can be used as a trial and includes a representative articulating surface 572 and a bone engaging surface 574.

The bone engaging surface 574 can be collectively formed by an anterior bone engaging surface 576, an anterior chamfer bone engaging surface 578, a distal bone engaging surface 580, a posterior chamfer bone engaging surface 582 and a posterior bone engaging surface 584. A series of bores 586 can be formed through the femoral cut-through-trial 570 for receiving pins (588, FIG. 46) to fix the femoral cut-though-trial 570 once the desired position has been attained on the distal femur. A pair of recessed flare portions 590 can be formed into the articulating surface 572. A threaded bore 592 can be provided at each of the recessed flare portions 590, respectively. A first and second series of medial cut slots 600 and 602 can be formed through the femoral cut-through-trial 570. A first and second series of lateral cut slots 604 and 606 can be formed through the femoral cut-through-trial 570. The first series of medial cut slots 600 can be used to guide the cutting instrument 534 for preparing medial cuts on the distal femur at a location generally parallel to the distal bone engaging surface 580.

The first series of lateral cut slots 604 can be used to guide the cutting instrument 534 for preparing lateral cuts on the distal femur at a location generally parallel to the distal bone engaging surface 580. As can be appreciated, the first series of medial and lateral cut slots 600 and 604 may be used if it is desired to remove portions of distal, medial and/or lateral femoral bone and replace the removed bone with distal femoral augments. Similarly, the second series of medial and lateral cut slots 602 and 606 can be used to guide a cutting instrument for cutting posterior portions of the distal femur in a location that is generally parallel to the posterior bone engaging surface 584 of the femoral cut-through-trial 570. In this regard, it may be desirable to remove portions of the medial and/or lateral posterior femur and replace that area with posterior augments that attach to a femoral component.

Figure 46:
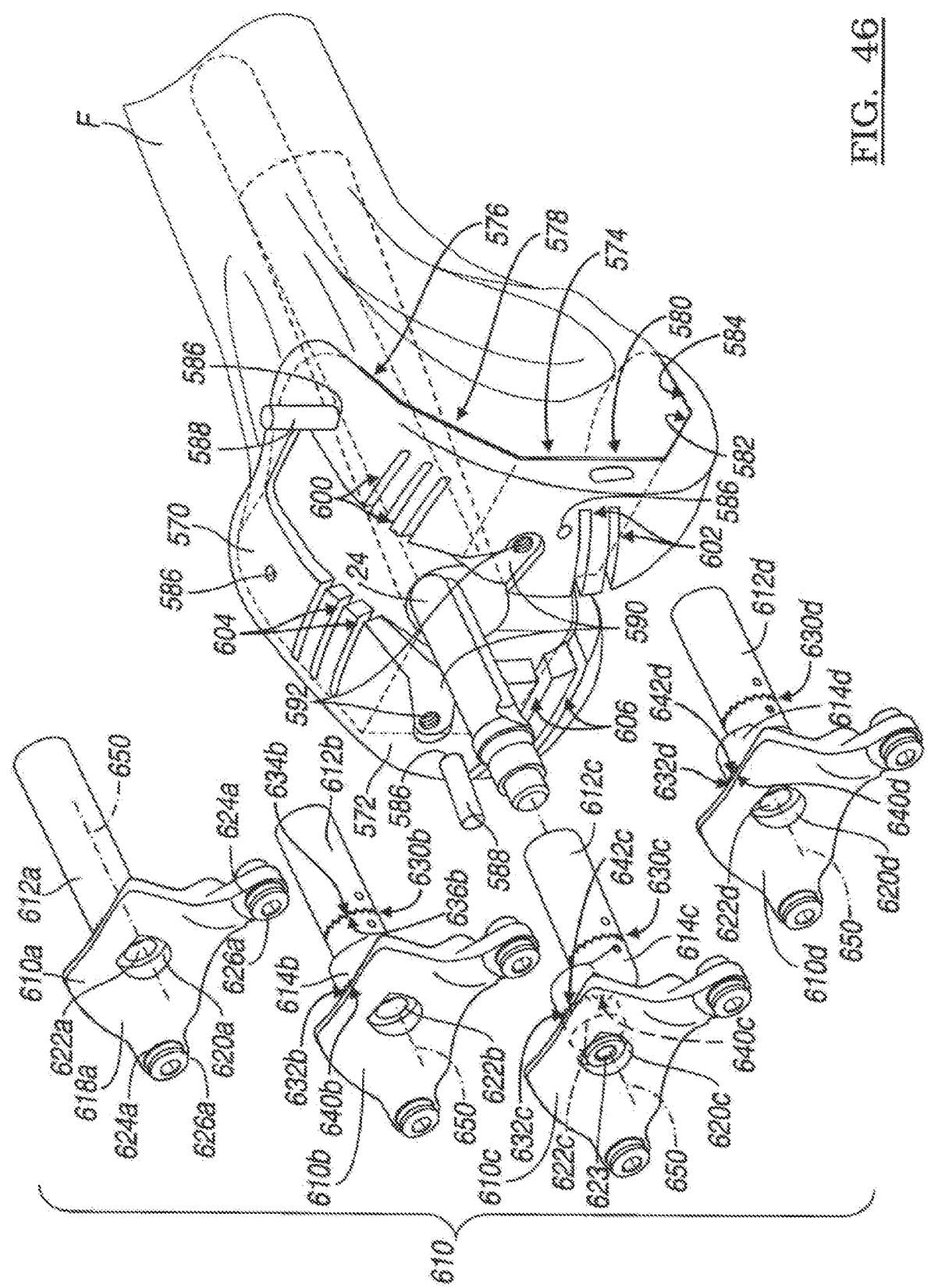
FIG. 46 is an anterior perspective view of the femoral cut-through trial shown with the locating stem extending from the IM canal and with a series of modular boss assemblies having various offsets that can selectively and alternatively connect to the locating stem.

With reference now to FIG. 46, a series of modular boss assemblies 610 are shown for selectively and alternatively cooperating with the locating stem 24 and the femoral cut-through-trial 570. In general, the series of modular boss assemblies are identified individually at reference numerals 610*a*, 610*b*, 610*c* and 610*d*. The series of modular boss assemblies 610 can correspond with the femoral offset coin assemblies 374. In this regard, the modular boss assembly 610*a* can have a boss stem 612*a* that corresponds to a zero offset. The modular boss assembly 610*b* can have a stem 612*b* that corresponds to a 2.5 mm offset. The modular boss assembly 610*c* has a boss stem 612*c* that corresponds to a 5 mm offset. The modular boss assembly 610*d* has a boss stem 612*d* that corresponds to a 7.5 mm offset.

The modular boss assembly 610b can have an intermediate offset body 614b. The modular boss assembly 610c can have an intermediate offset body 614c. The modular boss assembly 610d can have an intermediate offset body 614d. The modular boss assemblies 610a, 610b, 610c and 610d can each comprise a distal connection plate 618a, 618b, 618c and 618d defining a central aperture 620a, 620b, 620c and 620d for receiving a connector, such as a connector 623 shown on the modular boss assembly 610c. The distal connection plates 618a, 618b, 618c and 618d can each include a pair of passages 624a, 624b, 624c and 624d that are configured to receive fasteners 626a, 626b, 626c and 626d, respectively. The intermediate offset body 614b of the modular boss assembly 610b can interconnect the stem 612b with the connector 622b. The intermediate offset body 614c of the modular boss assembly 610c can interconnect the stem 612c with the connector 622c. The intermediate offset body 614d of the modular boss assembly 610d can interconnect the stem 612d with the connector 622d. The intermediate offset bodies 614b, 614c and 614d can have a proximal connecting end 630b, 630c and 630d, respectively. The intermediate offset bodies 614b, 614c and 614d can also include a distal connecting end 632b, 632c and 632d, respectively. Each of the proximal connecting ends 630b, 630c and 630d include a first plurality of interconnecting teeth 634b that selectively interlock with a second plurality of teeth 636b on the stem 612b. The first plurality of interconnecting teeth 634b, 634c and 634d of the intermediate offset bodies 614b, 614c and 614d can each be rotated around the second plurality of interconnecting teeth 634b, 634c and 634d in the respective stems.

The distal connecting ends 632b, 632c and 632d all include a third plurality of interconnecting teeth 640b, 640c and 640d that selectively engage a fourth plurality of interlocking teeth 642b, 642c and 642d provided on the connectors 622b, 622c and 622d, respectively. The third plurality of interconnecting teeth 640b, 640c and 640d of the intermediate offset bodies 614b, 614c can each be rotated around the fourth plurality of interconnecting teeth 640b, 640c and 640d on the connectors 622b, 622c and 622d. As can be appreciated, the intermediate offset bodies 614b, 614c and 614d can each rotate around a longitudinal axis 650 collectively defined through each of the distal connection plates 618a, 618b, 618c and 618d in order to position the respective stems 612b, 612c or 612d in a rotational orientation (or at the selected rotation angle or degree) that will align with the IM canal of the femur. Once the desired position on the distal femur F has been attained, the femoral cut-through-trial 570 can be fixed to the distal femur F with the pins 588. While only two pins 588 are shown, additional pins and/or pins located through other bores 586 may be used.

Figure 47:
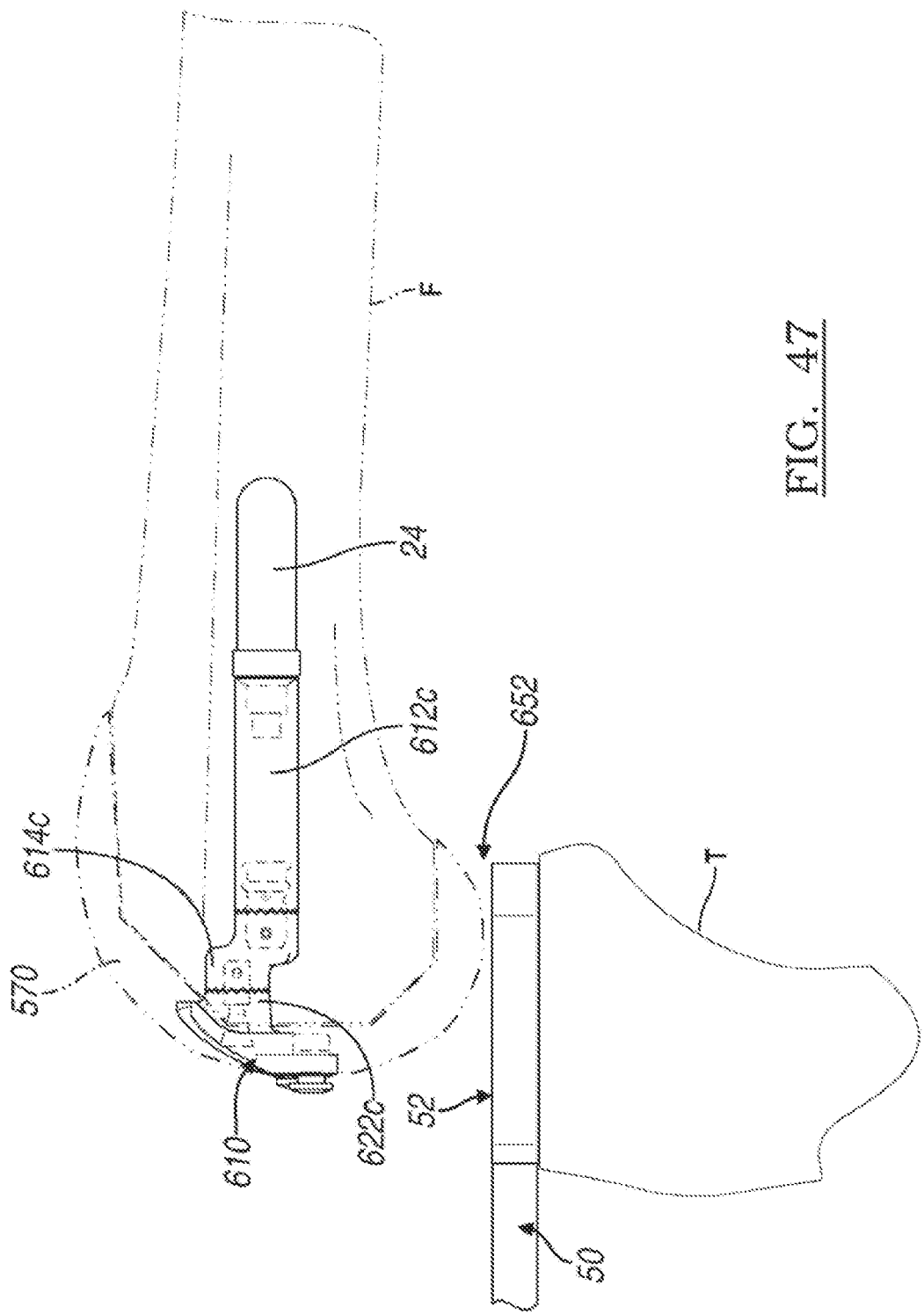
FIG. 47 is a medial view of the tibia and femur shown with a modular boss assembly connected to the femoral cut-through trial and with a spacer positioned atop the tibial plateau to verify a desired joint line.
Figure 48:
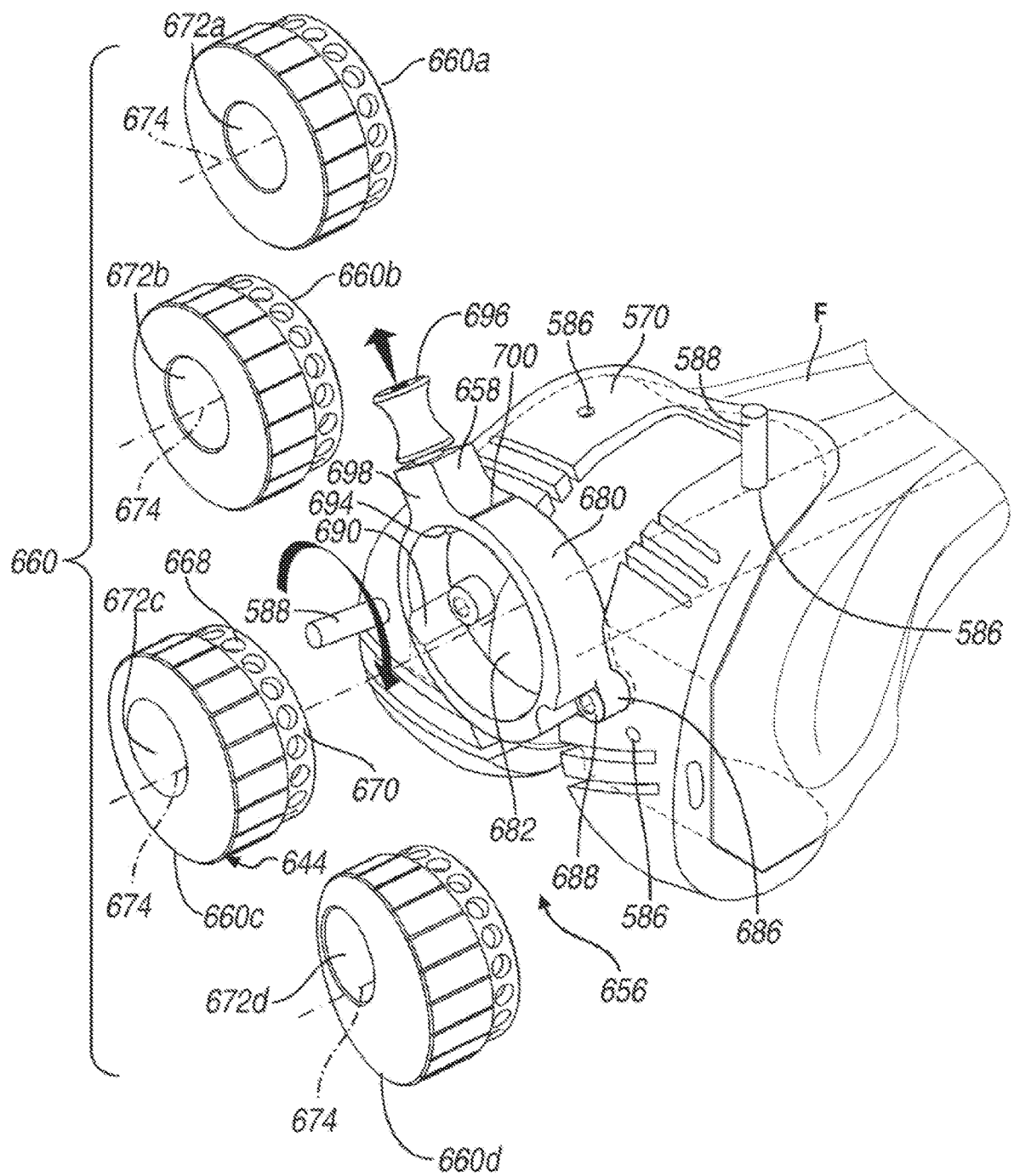
FIG. 48 is an anterior perspective view of the femur and shown with a positioning ring coupled to the femoral cut-through trial for receipt of a corresponding femoral reamer bushing.
Figure 49:
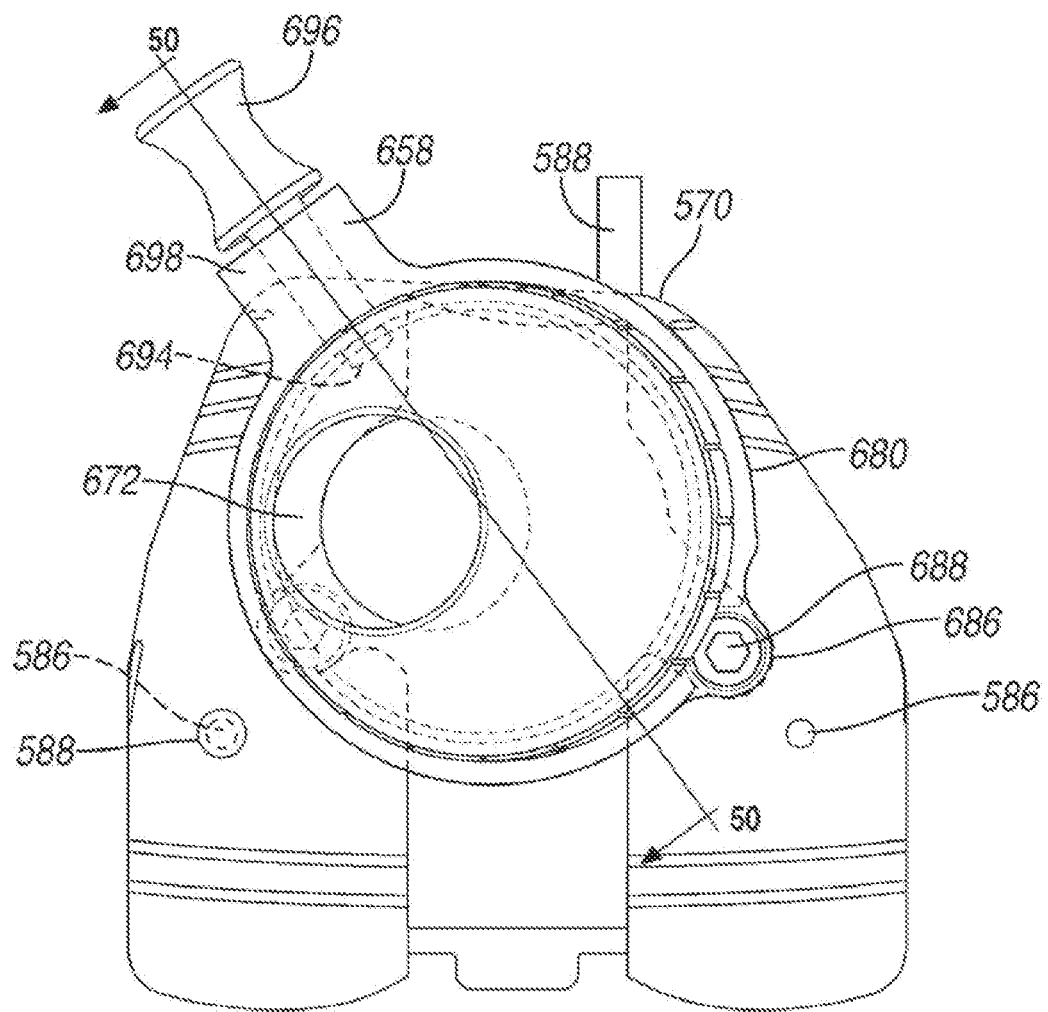
FIG. 49 is an inferior view of the femoral cut-through trial, positioning ring and selected femoral reamer bushings of FIG. 48.
Figure 50:
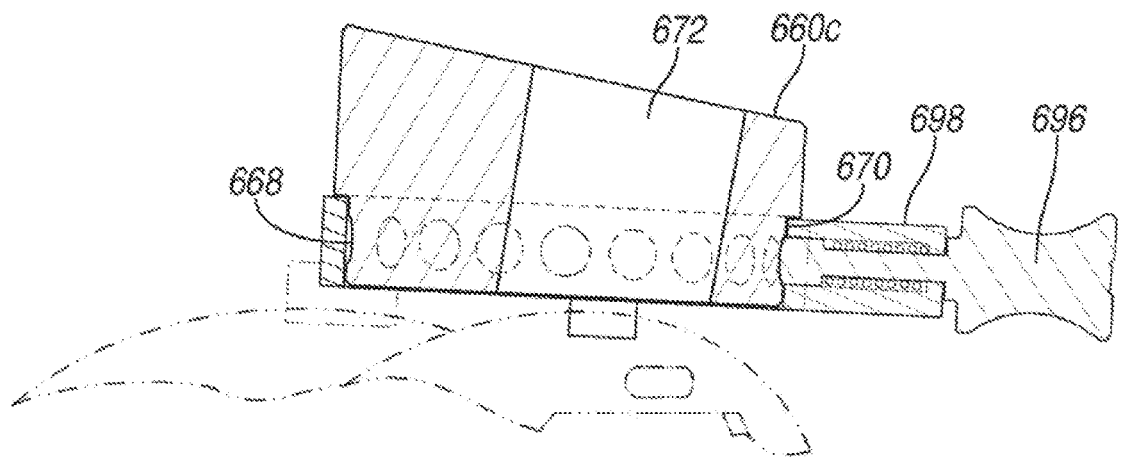
FIG. 50 is a cross-sectional view of the positioning ring and reamer bushing taken along lines 50-50 of FIG. 49.
Figure 51:
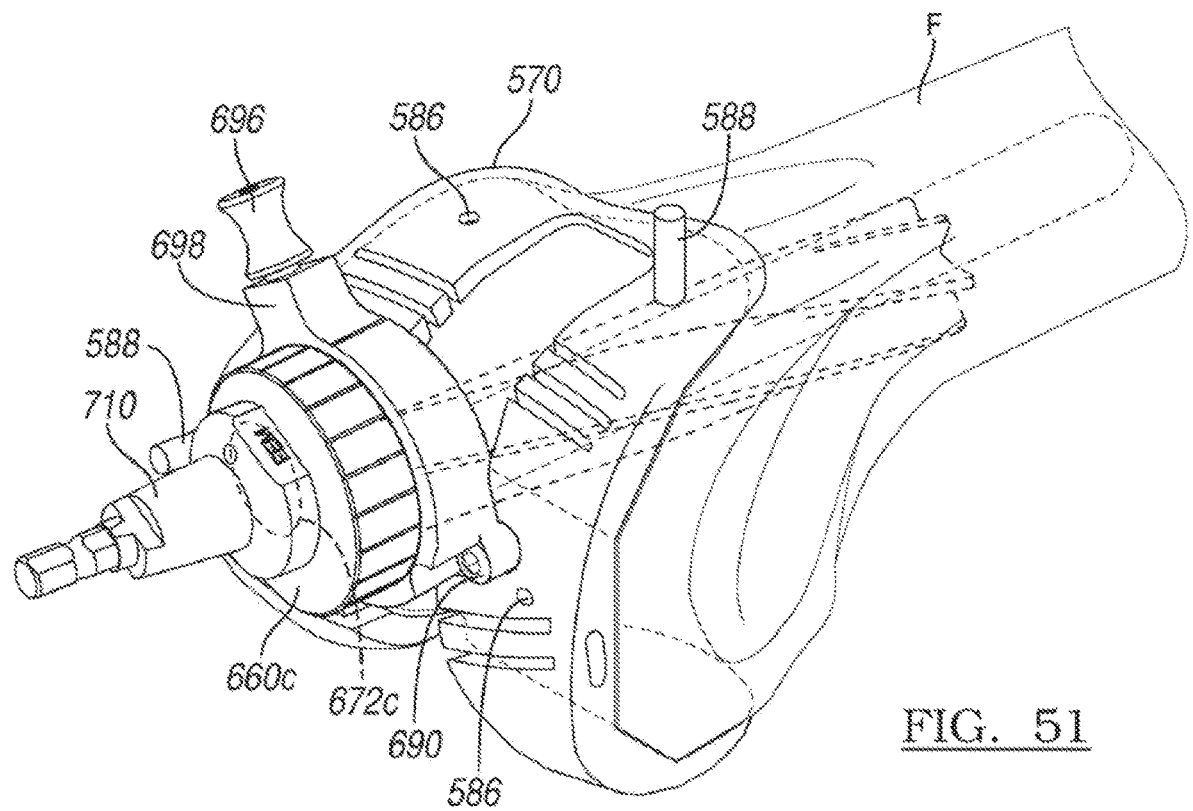
FIG. 51 is an anterior perspective view of the distal femur and shown with a femoral offset reamer located through the femoral reamer bushing and preparing a cavity in the femur for receipt of a femoral offset adapter.

Turning now to FIG. 47, additional features of the present teachings will be further described. With the femoral cut-through-trial 570 secured to the distal femur and with the modular boss assembly 610c attached at the recessed flare portion 590, the joint line 652 with respect to the tibia T can be visualized using one of the tibial spacers, such as the tibial spacer 50a. In this regard, the joint line is represented by the tibial plateau portion 52 of the tibial spacer 50a, which is determined based on anatomical landmarks. At this time, the distal augmentation needs for the tibia T and femur F can be determined.

Moreover, a thickness of a tibial bearing can be verified.

With reference now to FIGS. 48-52, reaming of the femur to accommodate a femoral offset adapter (such as the offset adapter 452, FIG. 54) will be described. A femoral offset reaming assembly 656 can include a positioning ring 658 and a series of reamer bushings, collectively referred to at reference numeral 660. The reamer bushings 660 can include a neutral reamer bushing 660a (0 mm offset or "neutral offset"), an offset reamer bushing 660b (2.5 mm offset), an offset reamer bushing 660c (5 mm offset) and an offset reamer bushing 660d (7.5 mm offset). Indicia marks 664 are collectively formed around all of the reamer bushings 660. Similarly, a plurality of locating bores 668 can be formed around a reduced diameter portion 670 of each of the reamer bushings 660. Offset bores 672a, 672b, 672c and 672d can be formed through each of the reamer bushings 660, respectively. The offset bores 672a, 672b, 672c and 672d can be all formed through the respective reamer bushings 660 at an offset location relative to a longitudinal axis collectively identified at reference numeral 674 of the reamer bushings 660. It can be appreciated that the offset bore 672a of the reamer bushing 660a can have a zero offset relative to the longitudinal or center axis 674.

The positioning ring 658 will now be described in greater detail. The positioning ring 658 can generally provide a ring-shaped body 680 that defines an opening 682 therein. A pair of locating portions 686 can have apertures 688 for receiving fasteners 690 that can selectively threadably locate into the threaded bores 592 on the femoral cut-through-trial 570. A locating peg 694 can extend from a pole handle 696 that extends out of a neck 698 of the ring-like body 680. As will be described, the peg 694 can selectively locate into one of the locating bores 668 once the desired indicia 664 aligns with a mark 700 on the positioning ring 658 to correspond with the noted indicia 444 that align with the notch 446 of the selected offset coin assembly 374 above.

Once the corresponding reamer bushing 660 has been selected that has an offset that matches an offset identified from the selected offset coin assembly 374, the reamer bushing (such as the reamer bushing 672c identified in FIG. 48) can be located into the opening 682 of the positioning ring 658. Next, the pole handle 696 can be pulled away from the ring-like body 680 and the reamer bushing 660c can be rotated around the central axis to align the corresponding indicia 664 with the mark 700 on the positioning ring 658 that corresponds with the noted indicia 440 and notch 446 determined above. At this point, the pole handle 696 can be pushed inwardly toward the ring-like body 680, such that the peg 694 securely locates into one of the locating bores 668 to preclude further rotation of the reamer bushing 660c around the central axis 674.

Figure 52:
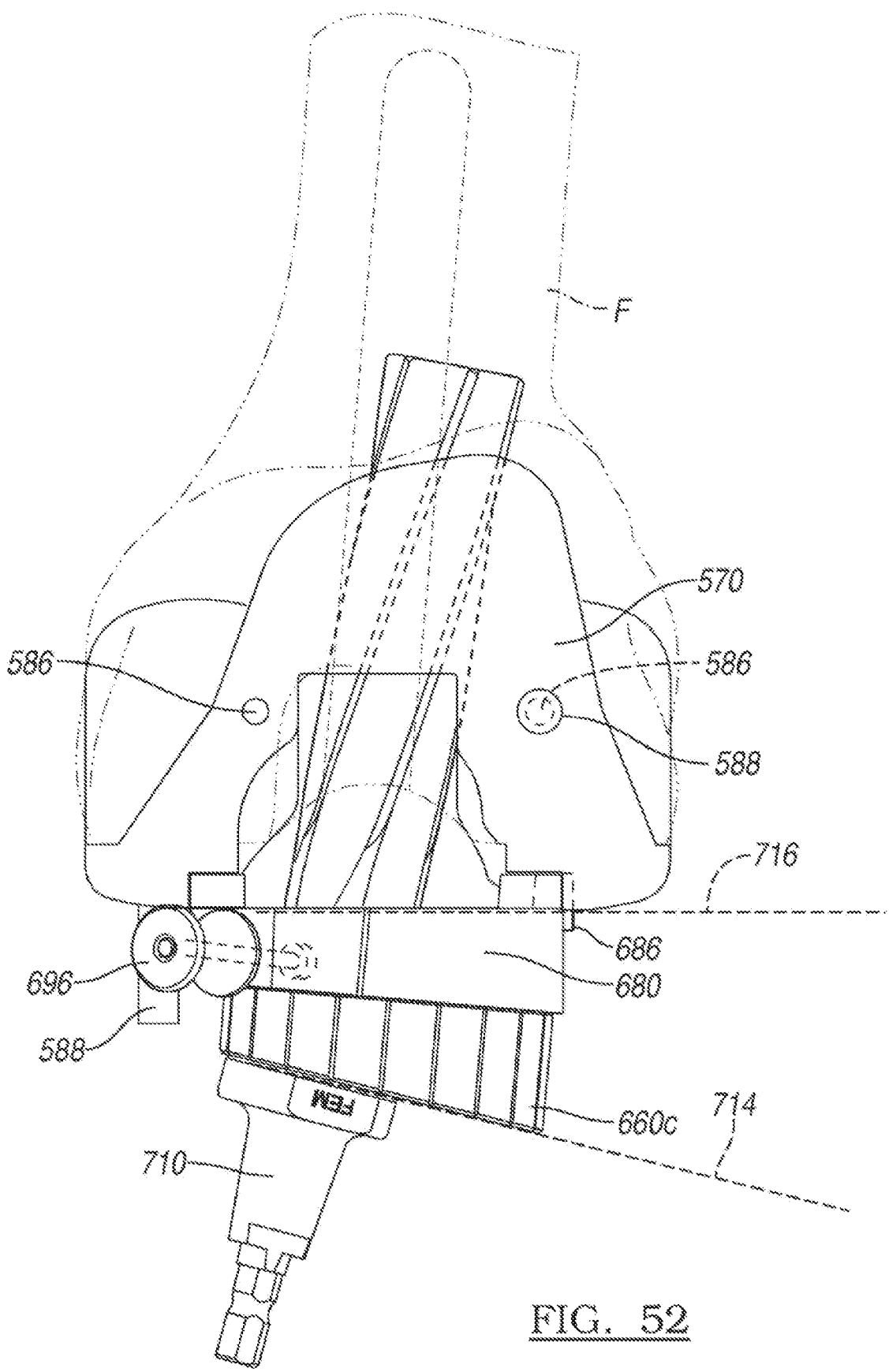
FIG. 52 is an anterior view of the distal femur shown with the femoral cut-through trial, positioning ring, femoral reamer bushing and femoral offset reamer of FIG. 51.

At this point, a femoral offset reamer 710 can be located into the offset bore 672c and the offset cavity can be reamed. As shown in FIG. 52, the offset reamer bushing 660c has a first plane 714 and a second plane 716 that are non-parallel. As can be appreciated, the series of reamer bushings 660 can be provided having various first and second planes that diverge at various distinct angles relative to the longitudinal axis of the femur F. As can be appreciated, each reamer bushing 660 can correspond to an angle of reaming that will accommodate the profile of any given offset adapter (such as the adapter 452, FIG. 54). In some examples, the neutral reamer bushing 660a can be used in instances where an offset adapter is unnecessary. It can be appreciated that the femoral offset reamer 710 can also ream an opening in the distal femur that will accommodate a femoral implant boss 720 (FIG. 54).

Figure 53:
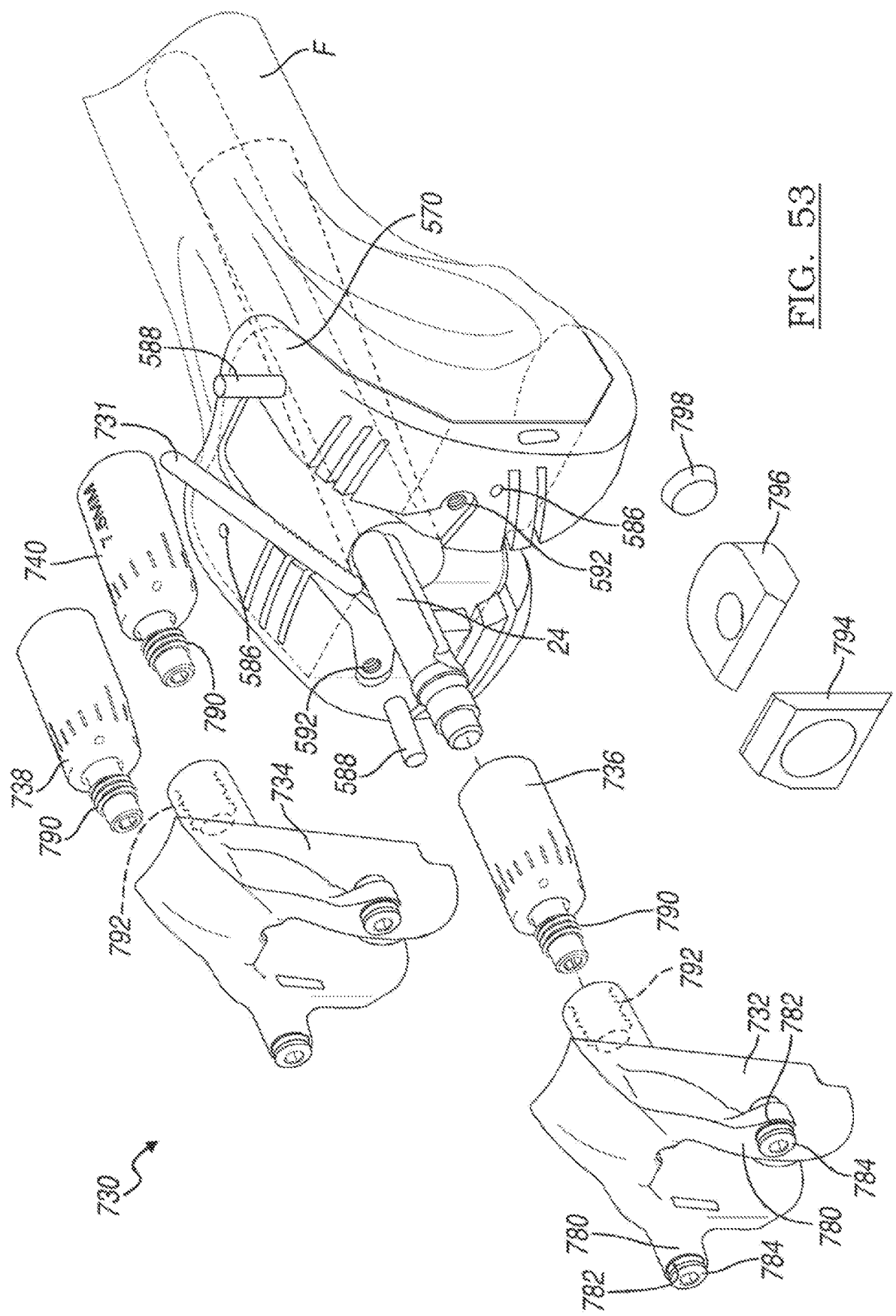
FIG. 53 is an anterior perspective view of the distal femur shown with the femoral cut-through trial with various trial offset adapters and modular boxes.

With reference now to FIG. 53, femoral trial components 730 can be used to cooperate with the femoral cut-through-trial 570 to trial the prepared distal femur. Again, the femoral cut-through-trial 570 remains fixed to the distal femur F. Prior to using the femoral trial components 730, a surgeon can cut a box opening into the distal femur with a cutting instrument 731 using the femoral cut-through-trial 570 as a reference.

The femoral trial component 730 can generally include a first modular box 732, a second modular box 734, a first trial offset adapter 736, a second trial offset adapter 738 and a third trial offset adapter 740. The first modular box 732 can be specific to a right femur while the second modular box 734 can be specific to a left femur. Each of the modular boxes 732 and 734 can include wing portions 780 that have passages 782 that receive fasteners 784. The fasteners 784 can be configured to threadably mate with the threaded bores 592 in the femoral cut-through-trial 570. The first trial offset adapter 736 can have a 2.5 mm offset, the second trial offset adapter 738 can have a 5 mm offset, and the third trial offset adapter 740 can have a 7.5 mm offset. As can be appreciated, each of the offsets can correspond with the positioning coins 422 and offset reamer bushings 660. Each of the trial offset adapters 736, 738 and 740 can have a threaded boss portion 790 that can threadably mate with a corresponding threaded bore 792 provided in each of the modular boxes 732 and 734, respectively. A distal augment spacer 794, and/or a posterior augment spacer 796 can be also used during the trial sequence. In one example, the augment spacers 794 and/or 796 can be magnetically coupled to the femoral cut-through-trial 570, such as with a magnet 798. The femur F can then be trialed.

Figure 30:
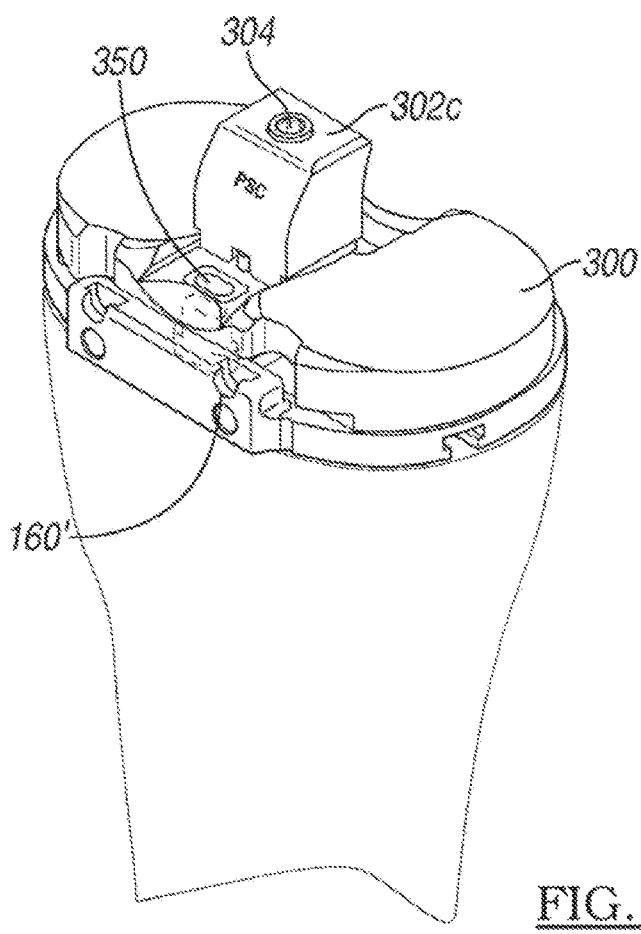
FIG. 30 is an anterior perspective view of the trial tibial tray shown with an alternate tibial bearing according to additional features.

In one example, the femoral trial component 730 can be articulated through flexion and extension such that the articulating surface 572 rotates against the trial tibial bearing 300 (FIG. 30). Once the femoral trialing sequence has identified a suitable femoral component, offset adapter and femoral stem, a surgeon can input and implant a femoral component 800, the offset adapter 452 and a femoral stem 450 as shown in FIG. 54.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system comprising:
a trial tibial bearing;
a trial tibial tray, wherein the trial tibial tray includes a posterior lip and an anterior engagement portion that includes a lock, wherein the trial tibial bearing can be selectively coupled to the trial tibial tray by locating a posterior catch of the trial tibial bearing under the posterior lip of the trial tibial tray and advancing an anterior end of the trial tibial bearing toward the trial tibial tray such that the lock captures the trial tibial bearing; and
a bearing removal tool for selectively removing the trial tibial bearing from the trial tibial tray, wherein the bearing removal tool includes a distal end and a proximal end, and an actuator that is slidably mounted on a central body of the bearing removal tool, wherein the bearing removal tool includes a distal tip on the distal end of the bearing removal tool, wherein the distal tip extends at an orthogonal angle relative to a longitudinal axis of the central body of the bearing removal tool, and wherein the distal tip is configured to depress the lock to disengage the anterior end of the trial tibial bearing from the trial tibial tray.

2. The system of claim 1, wherein the bearing removal tool is configured such that when the lock has been sufficiently depressed, a user can slidably advance the actuator to provide a gripping force onto the trial tibial bearing at a passage in the trial tibial bearing.

3. The system of claim 1, further including a plurality of different trial tibial bearings having various sizes and thicknesses, wherein the trial tibial bearing is selected from the plurality of different trial tibial bearings having various sins and thicknesses.

4. The system of claim 3, wherein the trial tibial bearing includes a superiorly extending member coupled to an upper surface of the trial tibial bearing.

5. The system of claim 4, further including a plurality of different superiorly extending members configured to be selectively coupled to the trial tibial bearing, wherein the superiorly extending member is selected from the plurality of different superiorly extending members configured to be selectively coupled to the trial tibial bearing.

* * * * *

UNITED STATES PATENT AND TRADEMARK OFFICE
CERTIFICATE OF CORRECTION

| | |
|---|---|
| PATENT NO. | : 11,660,212 B2 |
| APPLICATION NO. | : 16/927434 |
| DATED | : May 30, 2023 |
| INVENTOR(S) | : Belcher et al. |

It is certified that error appears in the above-identified patent and that said Letters Patent is hereby corrected as shown below:

In the Claims

In Column 24, Line 24, in Claim 1, delete "hearing" and insert --bearing-- therefor In Column 24, Line 34, in Claim 3, delete "sins" and insert --sizes-- therefor Signed and Sealed this
Eighth Day of August, 2023

*Katherine Kelly Vidal*

Katherine Kelly Vidal
*Director of the United States Patent and Trademark Office*